US010539488B2

(12) United States Patent
Goldsborough et al.

(10) Patent No.: US 10,539,488 B2
(45) Date of Patent: *Jan. 21, 2020

(54) SAMPLE FIXATION AND STABILISATION

(71) Applicant: RNASSIST LTD., Cambridge (GB)

(72) Inventors: Andrew Simon Goldsborough, Talence (FR); Malcolm Robert Bates, Cambridge (GB)

(73) Assignee: RNASSIST LTD., Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/676,365

(22) Filed: Aug. 14, 2017

(65) Prior Publication Data

US 2018/0058988 A1 Mar. 1, 2018

Related U.S. Application Data

(62) Division of application No. 15/608,300, filed on May 30, 2017, which is a division of application No. 14/193,680, filed on Feb. 28, 2014, now Pat. No. 9,696,247.

(30) Foreign Application Priority Data

Mar. 1, 2013 (GB) .................................. 1303666.0

(51) Int. Cl.
*A01N 1/02* (2006.01)
*G01N 1/30* (2006.01)

(52) U.S. Cl.
CPC ............. *G01N 1/30* (2013.01); *A01N 1/0231* (2013.01); *G01N 2001/307* (2013.01)

(58) Field of Classification Search
None
See application file for complete search history.

(56) References Cited

U.S. PATENT DOCUMENTS

| | | | |
|---|---|---|---|
| 3,667,928 A | 6/1972 | Backlund | |
| 4,579,580 A | 4/1986 | Moore | |
| 5,010,183 A | 4/1991 | MacFarlane | |
| 5,300,635 A | 4/1994 | MacFarlane | |
| 6,602,718 B1 | 8/2003 | Augello et al. | |
| 6,617,170 B2 | 9/2003 | Augello et al. | |
| 6,777,210 B1 | 8/2004 | Pasloske et al. | |
| 7,270,953 B2 | 9/2007 | Hollander et al. | |
| 7,682,790 B2 | 3/2010 | Hollander et al. | |
| 7,763,715 B2 | 7/2010 | Hecht et al. | |
| 8,022,014 B2 | 9/2011 | Miller | |
| 8,247,198 B2 | 8/2012 | Gorke et al. | |
| 8,372,637 B2 | 2/2013 | Hollander | |
| 9,696,247 B2 * | 7/2017 | Goldsborough | G01N 1/30 |
| 2004/0077519 A1 | 4/2004 | Price et al. | |
| 2004/0156920 A1 | 8/2004 | Kane | |
| 2006/0094616 A1 | 5/2006 | Hecht et al. | |
| 2009/0117628 A1 | 5/2009 | Gorke et al. | |
| 2009/0247432 A1 | 10/2009 | Miller | |
| 2009/0286304 A1 | 11/2009 | Latham et al. | |
| 2012/0021383 A1 | 1/2012 | Skarla et al. | |
| 2012/0213838 A1 | 8/2012 | Egashira et al. | |
| 2013/0149322 A1 | 6/2013 | van Spronsen et al. | |
| 2015/0267245 A1 | 9/2015 | Hogan | |

FOREIGN PATENT DOCUMENTS

| | | |
|---|---|---|
| CN | 1503910 | 6/2004 |
| CN | 102711674 | 10/2012 |
| EP | 2516017 | 10/2012 |
| EP | 2575993 | 10/2013 |
| WO | WO 02/056030 | 7/2002 |
| WO | WO 2006/116126 | 11/2006 |
| WO | 2011/155829 | 12/2011 |
| WO | WO 2011/155829 | 12/2011 |
| WO | WO 2012/145522 | 10/2012 |
| WO | WO 2014/055936 | 4/2014 |
| WO | WO 2014/197090 | 12/2014 |

OTHER PUBLICATIONS

Abbott et al., Design of Improved Deep Eutectic Solvents Using Hole Theory; ChemPhysChem, vol. 7, pp. 803-806, 2006 (Year: 2006).*
Lu et al., Study of Deep Eutectic Solvents Based Betaine Hydrochloride and Urea; J. Kunming U of Science and Technology, vol. 35, No. 6, pp. 10-14, 2010 (Year: 2010).*
Machine translation of Lu et al., Study of Deep Eutectic Solvents Based Betaine Hydrochloride and Urea; J. Kunming U of Science and Technology, vol. 35, No. 6, pp. 10-14, 2010 (Google translate accessed Apr. 11, 2019) (Year: 2019).*
Francisco et al, New natural and renewabie low transition temperature mixturas (LTTMs): screening as solvents for lignocellulosic biomass processing; Grew Chem, vol. 14, pp. 2153-2157, 2012.
Shahbaz et al., Using deep eutectic solvents for the removal of glycerol from palm oil-based biodiesel (J Applied Sciences, vol. 10, No. 24, pp. 3349-3354, 2010.
Zhang et al., Deep eutectic solvents: syntheses, properties and applications; Chem Soc Rev, vol. 41, pp. 7108-7146, 2012.
Abbott, A. et al., "Deep Eutectic Solvents Formed between Choline Chloride and Carboxylic Acids: Versatile Alternatives to Ionic Liquids", J. Am. Chem. Soc. 2004; 126: 9142-9147.

(Continued)

*Primary Examiner* — Addison D Ault

(74) *Attorney, Agent, or Firm* — Robin L. Teskin; Baker, Donelson, Bearman, Caldwell & Berkowitz PC

(57) ABSTRACT

It has surprisingly been discovered that it is possible to stabilize biomolecules such as RNA, DNA and proteins in biological samples such as cells, tissues, biopsies and blood using deep eutectic solvents (DES). It has also been discovered that DES mixtures can be used to fix and preserve cell morphology in biological samples such as tissue blocks, cancer biopsies and whole blood. This invention describes methods to stabilize and preserve biomolecules, whole cells, tissues, blood and biological samples using DES mixtures.

18 Claims, 10 Drawing Sheets

(56) References Cited

OTHER PUBLICATIONS

Abbott, A. et al., "Novel solvent properties of choline chloride/urea mixtures", Chem. Commun. 2003; 70-71.
Abbott, A. et al., "Processing of Electric Arc Furnace Dust using Deep Eutectic Solvents", Aust. J. Chem. 2009; 62: 341-347.
Abbott, A. et al., "Eutectic-Based Ionic Liquids with Metal-Containing Anions and Cations", Chem. Eur. J. 2007; 13: 6495-6501.
Azizi, N. et al., "Eutectic Salt Catalyzed Environmentally Benign and Highly Efficient Bigineili Reaction", The Scientific World Journal 2012; Id No. 908702, 6 Pages.
Chirgwin, J. et al., "Isolation of Biologically Active Ribonucleic Acid from Sources Enriched in Ribonuclease", Biochemistry 1979; 18(24): 5294-5299.
Chomczynski, P. and Sacchi, N. "Single-Step Method of RNA Isolation by Add Guanidinium Thiocyanate-Phenal-Chloroform Extraction", Analytical Biochemistry 1987; 162: 156-159.
Choy, E. et al., "Pharmacokinetic, pharacodynarnic and clinical effects of a humanized IgG1 anti-CD4 monoclonal antibody in the peripheral blood and synovial fluid of rheumatoid arthritis patients", Rheumatology 2000; 39: 1139-1146.
Freudenmann, D. et al, "Ionic Liquids: New Perspectives for Inorganic Synthesis?", Angew. Chem. Int. Ed. 2011; 50: 11050-11060.
Dai, Y. et al., "Natural deep eutectic solvents as new potential media for green technology", Analytica Chimica Acta 2013; 766: 61-68.
De Vreese, P. et al, "Speciation of Copper(II) Complexes in an Ionic Liquid Based on Choline Chloride and in Choline Chloride/Water Mixtures", Inorg. Chem. 2012; 51: 4972-4981.
Durand, E. et al, "Deep eutectic solvents: Synthesis, application, and focus on lipase-catalyzed reactions", Eur. J. Lipid Sci, Technol. 2013; 115: 379-385.
Gomez, E. et al, "Electrodeposition of Co, Sm and SmCo from a Deep Eutectic Solvent", Journal of Electoanalytical Chemistry, 2011; 658: 18-24.
Figueiredo, M. et al., "Differential capacity of a deep eutectic solvent based on choline chloride and glycerol on solid electrodes", Electrochimica Acta 2009; 54: 2630-2634.
Imperato, G. et al., "Low-melting sugar-urea-salt mixtures as solvents for Diels-Alder reactions", Chem. Commun. 2005; 1170-1172.
Gora, R. et al., "Resonance-assisted hydrogen bonds revisited. Resonance stabilization vs. charge delocalization", Phys. Chem. Chem. Phys. 2013; 15: 2514-2522.
Gutierrez, M. et al., "Freeze-Drying of Aqueous Solutions of Deep Eutectic Solvents: A Suitable Approach to Deep Eutectic Suspensions of Self-Assembled Structures", Langmuir 2009; 25(10): 5509-5515.
Gutierrez, M. et al., "Bacteria Incorporation in Deep-eutectic Solvents through Freeze-Drying", Angew. Chem. Int. Ed. 2010; 49: 2158-2162.
Morrison, H. et al, "Characterization of thermal behavior of deep eutectic solvents and their poteintial as drug solubilization vehicles", International Journal of Pharmaceutics 2009; 378: 136-139.
Jhong, H. et al, "A novel deep eutectic solvent-based ionic liquid used as electrolyte for dye-sensitized solar cells", Electrochemistry Communications 2009; 11: 209-211.
Hayden, P. et al., "Detection of Cysteine Conjugate Metabolite Adduct Formation with Specific Mitochondrial Proteins Using Antibodies Raised against Halothane Metabolite Adducts", J. Biol. Chem. 1991; 266(28): 18415-18418.
Hayyan, M. et al., "Are deep eutectic solvents benign or toxic?", Chemosphere 2013; 90; 2193-2195.
Honda, K. et al, "Ribosomal RNA in Alzheimer Disease is Oxidized by Bound Redox-active Iron", J. Biol. Chem. 2005; 280(22): 20978-20986.
Gorke, J. et al., "Hydrolase-catalyzed biotransformations in deep eutectic solvents", Chem. Commun. 2008; 1235-4237.
Shahbaz, K. et al., "Using Deep Eutectic Solvents Based on Methyl Triphenyl Phosphunium Bromide for the Removal of Glycerol from Palm-Oil-Based Biodiesel", Energy Fuels 2011; 25: 2671-2678.
Kawai, K. et al., "Simple pretreatment of non-conductive small hydrous bio-samples with choline-type ionic liquid and membrane filter for microsample mounting", Colloids and Surfaces B: Biointerfaces 2013; 102: 942.
Kawal, K. et al., "Hydrophilic Quaternary Ammonium Type Ionic Liquids. Systematic Study of the Relationship among Molecular Structures, Osmotic Pressures, and Water-Solubility", Langmuir 2011; 27: 7353-7356.
Kawai, K. et al "Bioinspired Choline-like ionic Liquids: Their Penetration Ability through Cell Membranes and Application to SEM Visualization of Hydrous Samples", Langmuir, 2011; 27: 9671-9675.
Kelley, S. et al., "Understanding the Effects of Ionicity in Salts, Solvates, Co-Crystals, Ionic Co-Crystals, and Ionic Liquids, Rather than Nomenclature, Is Critical to Understanding Their Behavior", Cryst. Growth Des. 2013; 13: 965-975.
Lannan, F. et al., "Human Telomere Sequence DNA in Water-Free and High-Viscosity Solvents: G-Quadruplex Folding Governed by Kramers Rate Theory", J. Am. Chem. Soc. 2012; 134: 15324-15330.
Mota-Morales, J. et al., "Frontal polymerizations carried out in deep-eutectic mixtures providing both the monomers and the polymerization medium", Chem. Commun, 2011; 47: 5328-5330.
Muyal, J. et al., "Systematic comparison of RNA extraction techniques from frozen and fresh lung tissues: checkpoint towards gene expression studies", Diagnostic Pathology 2009; 4:9.
Nardecchia, S. et al., "Phase Behavior of Elastin-Like Synthetic Recombinamers in Deep Eutectic Solvents", Biomacromolecules 2012; 13: 2029-2036.
Niedermeyer, H. et al., "Mixtures of ionic liquids", Chem. Soc. Rev. 2012; 41: 7780-7802.
Nkuku, C. et al., "Electrochemistry in Deep Eutectic Solvents", J. Phys. Chem. B 2007; 111: 13271,-13277.
Prashad, M. et a., "A new, cenvenient and selective 4-dimethylaminopyridine-catalized trifluroacetylation of anilines with theyl trifluoroacetate", Tetrahedron Letters 2000; 41: 9957-9961.
Raines, R., "Ribonuclease A", Chem. Rev. 1998; 98: 1045-1065.
Roosen, C. et al,, "Ionic liquids in biotechnology: applications and perspectives biotransformations", Appl. Microbiol. Biotechnol. 2008; 81:607-614.
Gore, S. et al., "Efficient synthesis of 3,4-dihydropyrimidin-2-ones in low melting tartaric acid-urea mixtures", Green Chem. 2011; 13: 1009-1013.
Spencer, C. et al., "Practical cleavage of trifluoroacetamides with p-toluensulfonic acid", Tetrahedron Letters 2009; 50: 1010-1012.
Summersgill, B. et al., "Fluorescence and chromogenic in situ hybridization to detect genetic aberrations in formalin-fixed paraffin embedded material, including tissue microarrays", Nature Protocols. 2008; 3(2): 220-234.
Thompson, J. and Gillespie, D., "Molecular Hybridization with RNA Probes in Concentrated Solutions of Guanidine Tiocyanate", Analytical Biochemistry, 1987; 163: 281-291.
Li, X. et al., "Solubility of $CO_2$ in a Choline Chloride + Urea Eutectic Mixture", J. Chem. Eng, 2008; 53: 548-550.
Xu, D. et al., "Ethyl Trifluoroacetate: A Powerful Reagent for Differentiating Amino Groups", Tetrahedron Letters. 1995. 36(41): 7357-7360.
Choi, Y.H. et al., "Are Natural Deep Eutectic Solvents the Missing Link in Understanding Cellular Metabolism and Physiology?", Plant Physiology. 2011; 156: 17014.705.
Yarus, M., "How many catalytic RNAs? Ions and the Cheshire cat conjecture", FASEB J. 1993; 7: 31-39.
Zhang, Q. et al., "Deep eutectic solvents: synthesis, properties and applications", Chem. Soc. Rev. 2012; 41: 7108-7146.
Zhao, H. et al., "Protease activation in glycerol-based deep eutectic solvents", Journal of Molecular Catalysis B: Enzymatic. 2011; 72: 163-167.
Zhao, C. et al., "G-Quadruplexes Form Ultrastable Parallel Structures in Deep Eutectic Solvent", Langmuir. 2013; 29: 1183-1191.

(56) References Cited

OTHER PUBLICATIONS

Anicai, L. et al., "Chapter 13: Studies Regarding the Nickel Electrodeposition from Choline Chloride Based Ionic Liquids." In: Applications of Ionic Liquids in Science and Technology, Handy S (Ed.); Middle Tennessee State U, 2011.

Reich, Hans J. "Bordwell PKa Table (Acidity in DMSO)." Bordwell PKa Table (Acidity in DMSO). University of Washington Department of Chemistry, Oct. 11, 2001. Web. Jan. 20, 2015.

Wikimedia Foundation, "Deep Eutectic Solvent." http://en.wikipdedia.org/wiki/Deep_eutectic_solvent, retrieved Jan. 20, 2015.

University of Leicester, "Leicester Ionic Liquids Group." http://www.leicester-ils.co.uk/research.html, Retrieved Jan. 20, 2015.

LeBlanc, R., "Novel Amino Protecting Group Chemistry", Department of Medicinal Chemistry, School of Pharmacy, VCU. Nov. 2, 2001.

Scionix and C-Tech Innovation. Biocatalysis: Deep Eutectic Solvents Trial Pack.

De la Fuente, M., "Enzyme Catalysis in Deep Eutectic Solvents", Department of Biochemistry & Organic Chemistry, Uppsala University.

Shahbaz, K. et al., "Removal of Residual KOH from Palm Oil Based Biodiesel Using Deep Eutectic Solvents", Paper in: Chemeca 2011, Sep. 18-21, 2011. Hilton Sydney, New South Wales, Australia.

Leron, R.B. et al., "Carbon dioxide solubility in a choline chloride-urea dap eutectic solvent", 2012 Taiwan Symposium on Carbon Dioxide Capture, Storage and Utilization, Nov. 25-27, 2012. NTUH International Convention Center, Taipei, Taiwan.

Goldsborough, A. and Bates, M., "RNA Assist—a novel tissue fixative and RNA stabilization reagent", Poster Abstract Molecular Medicine Tr-Conference, San Francisco, Feb. 2013.

PreAnalytiX. PAXgene Blood RNA Kit Handbook, Version 2. Jun. 2005.

Berger, S. and Birkenmeier, C., "Inhibition of Intractable Nucleases with Ribonucleoside-Vanadyl Complexes: Isolation of Messenger Ribonucleic Acid from Resting Lymphocytes", Biochemistry. 1979; 18(23): 5143-5149.

"Deep Eutectic Solvents (DESs) in Biology" Group of Bioinspired Materials, Instituto de Ciencia de Materiales de Madrid, CSIC n.d. Web. Jan. 20, 2015.

Grolz, D. "Human Tissue Research Conference", PreAnalytiX. The PAXgene Tissue System. Apr. 14-15, 2010.

Mamajanov, et al. "DNA and RNA in anhydrous media: duplex, triplex, and G-quadruplex secondary structures in a deep eutectic solvent," Angew Chem 2010 122, 6451-6458.

De Maria and Maugeri, "Ionic liquids in biotransfomiations: from proof-of-concept to emerging deep-eutectic-solvents," Curr Opin Chem Biol. 2011, 15, 220-225.

\* cited by examiner

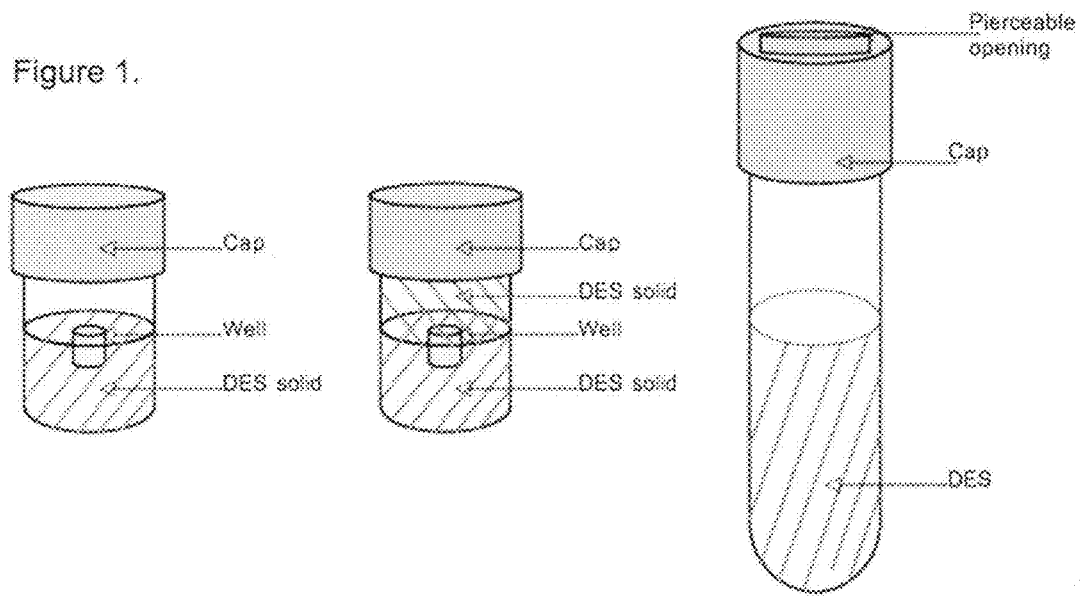
Figure 1.
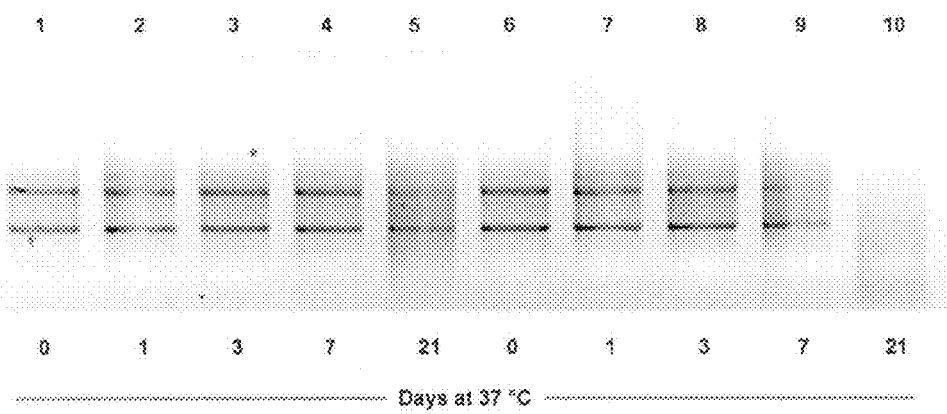
Figure 2. Long term stabilisation of RNA in rat liver.

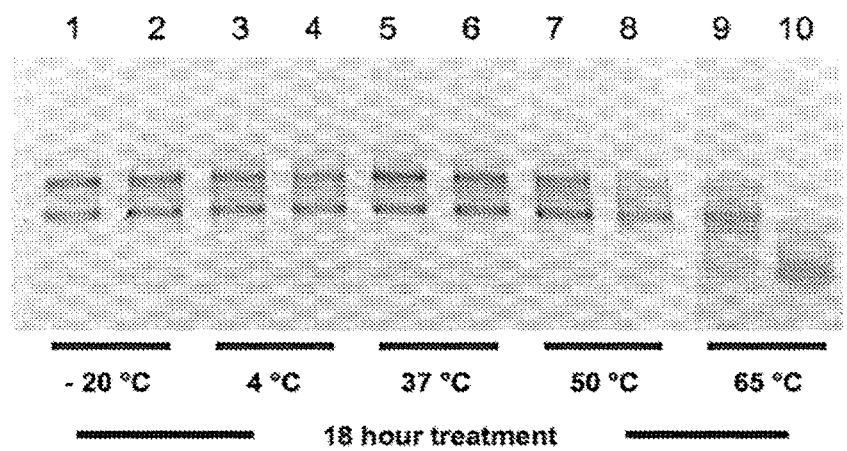
Figure 3. RNA stabilisation in Choline chloride:Urea at a range of temperatures.
Figure 4. Long term preservation of RNA in tissue using Choline chloride:Urea (1:2)
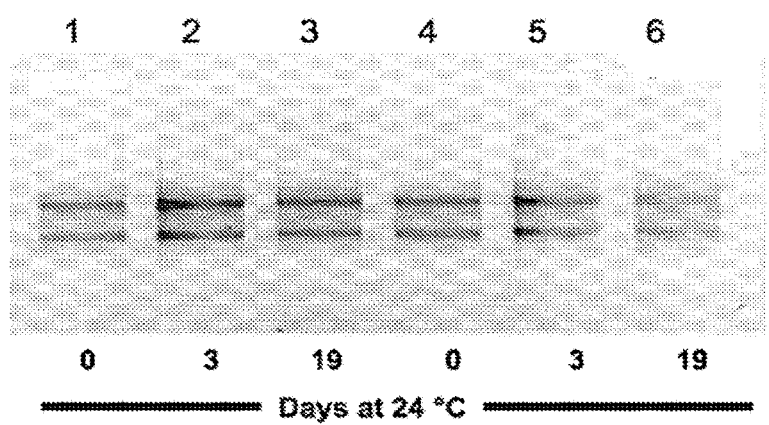

Figure 5A. RNA stabilisation in mouse kidney and brain samples at 37°C.
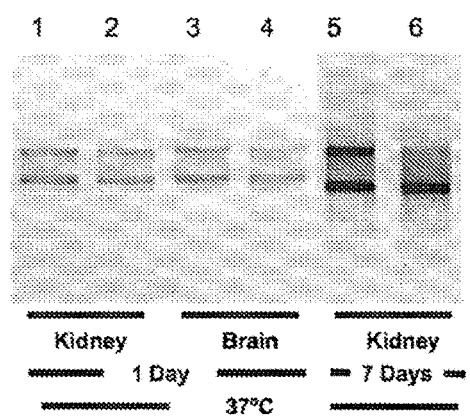
Figure 5B. RNA stabilisation in mouse tissue samples.
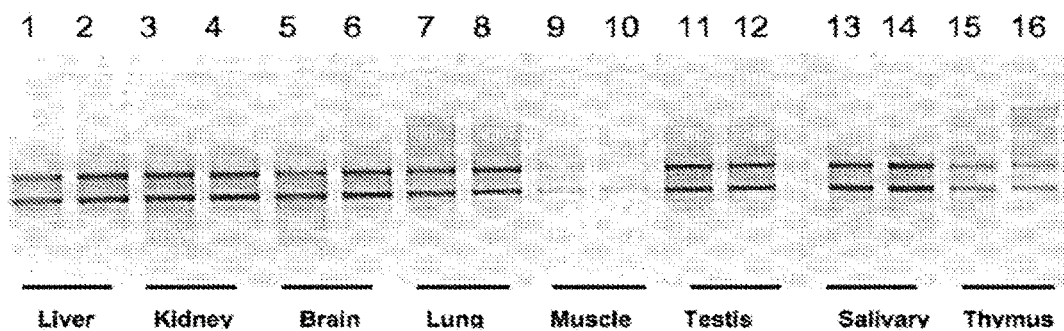

Figure 6. Preservation of RNA in varying amounts of tissue
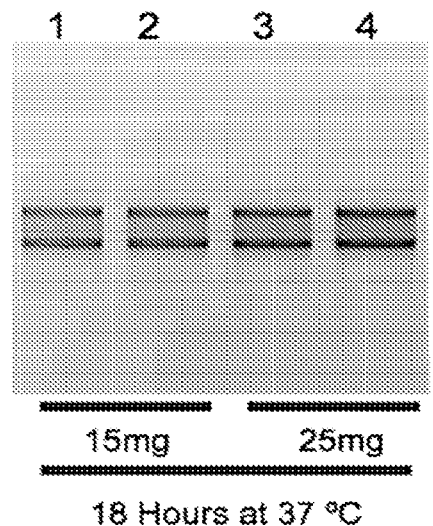
Figure 7. RNA purification from whole blood samples.
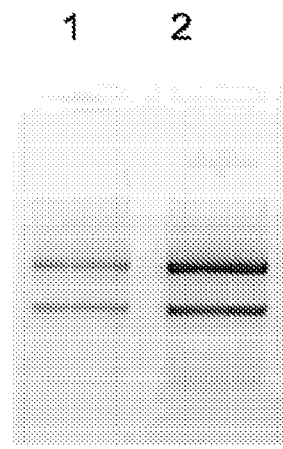

Figure 8. Gel showing RNA quality of stabilised RNA samples
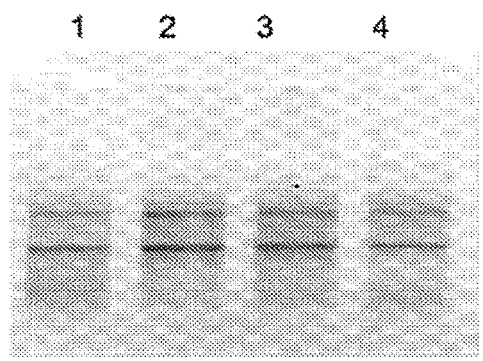
Figure 9. Stabilisation of RNA in whole blood with either Guanidine or Choline chloride:Trifluoroacetamide
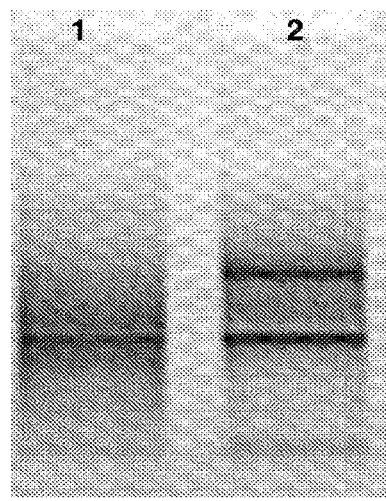

Figure 10. Light microscope images HeLa cells fixed with Choline chloride:Trifluoroacetamide.
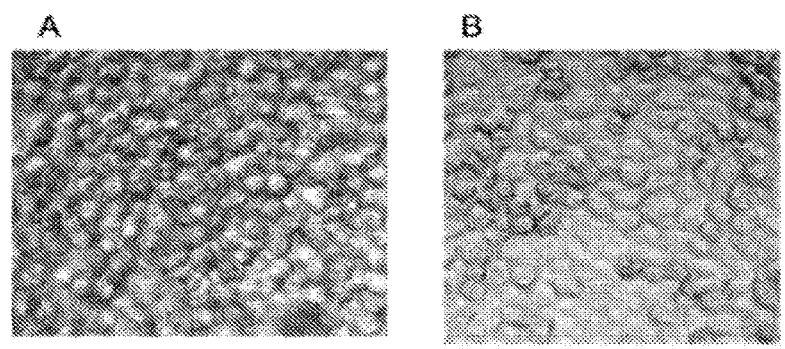

Figure 11. RNA degradation in tissues in the absence of stabiliser.
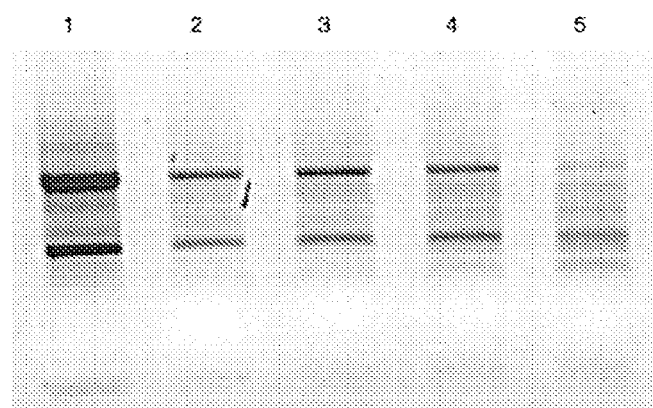
Figure 12. Genomic DNA Stabilisation.
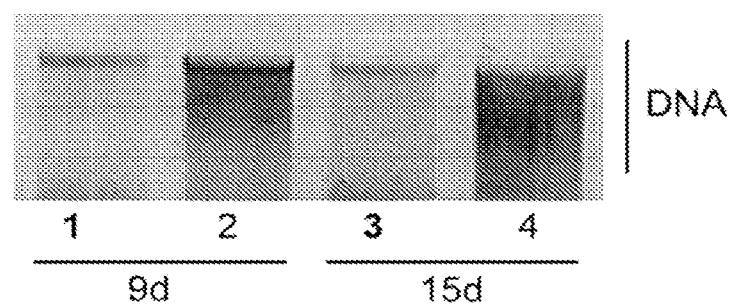

Figure 13. Protein stabilisation.
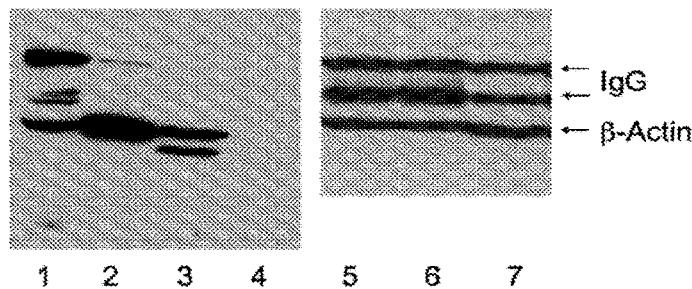
Figure 14. HeLa cell RNA and DNA integrity after fixation and paraffin embedding. A plus (+) sign indicates that the processing step was carried out prior to nucleic acid purification.
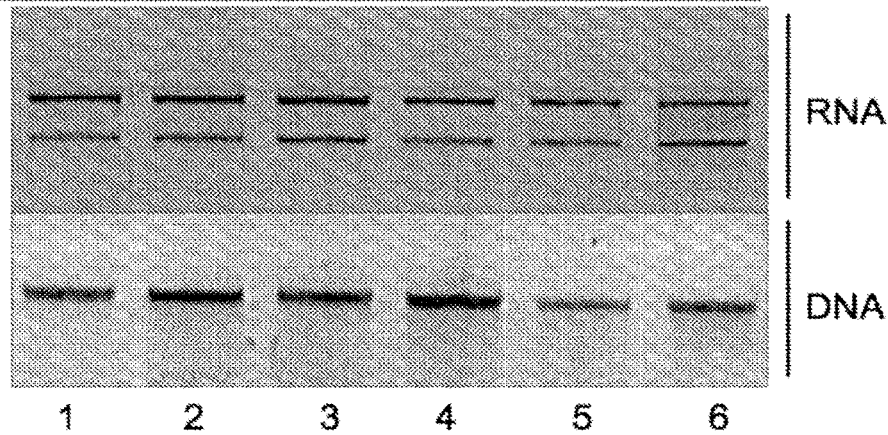

Figure 15. Mouse tissue RNA and DNA integrity after fixation in Choline chloride:Trifluoroacetamide or PBS incubation followed by paraffin embedding then nucleic acid extraction.
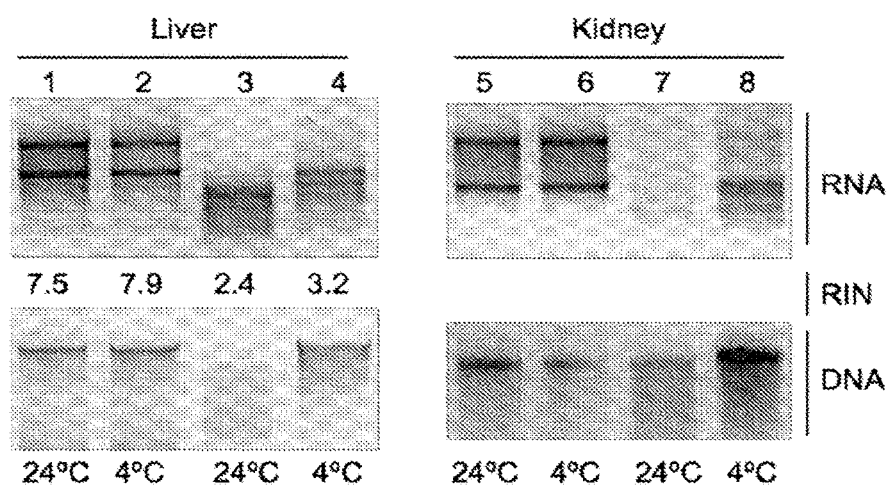
Figure 16 RNA stabilisation in Drosophila embryos.
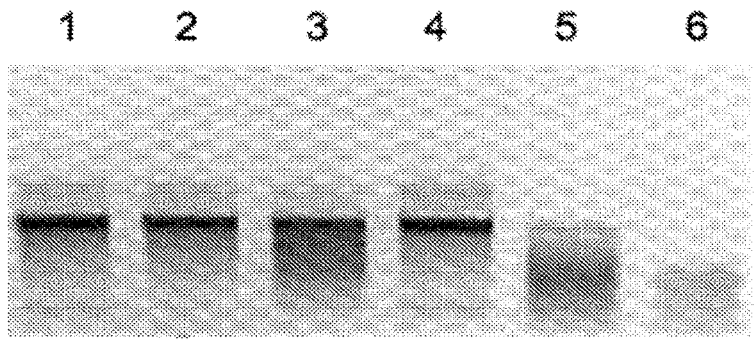

Figure 17. RNA stabilisation in A. cepa leaf shoots.
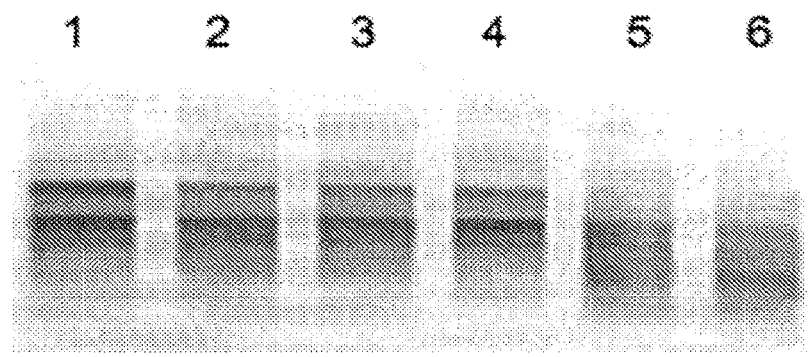

SAMPLE FIXATION AND STABILISATION

PRIORITY APPLICATION INFORMATION

This application is a divisional application of U.S. application Ser. No. 15/608,300 filed May 30, 2017, which is a divisional application of U.S. application Ser. No. 14/193,680, filed Feb. 28, 2014, which claims priority to United Kingdom Patent Application GB 1303666.0 filed Mar. 1, 2013, all of which are incorporated by reference in their entirety herein.

FIELD OF THE INVENTION

The present invention relates to the stabilisation of biomolecules, in particular RNA, including methods for stabilising RNA, compositions and kits for stabilising RNA, and stabilised RNA-containing compositions. It also relates to the fixation and stabilisation of cells, tissues, blood, exosomes and other biological samples.

BACKGROUND OF THE INVENTION

The extraction of intact biomolecules from a biological sample is an essential part of many laboratory and clinical diagnostic procedures. The instability of biomolecules such as nucleic acids, proteins, carbohydrates and lipids is well known and their integrity depends on a large number of parameters such as the physiological condition of the sample prior to removal from its original environment, how quickly the sample was removed from its source, the rate of sample cooling, sample storage temperature and the biomolecule purification method. It is well known that the treatment of the biological sample before and during biomolecule purification can lead to very important changes in the intactness and integrity of the sample analyte. For example it is well known that RNA in particular is an extremely labile molecule that becomes completely and irreversibly damaged within minutes if it is not handled correctly. Although RNA is perhaps one of the more labile biomolecules, proteins including post-translational modifications, lipids, small molecules of less than 2000 daltons that are essential to metabolic analysis and DNA can also be subject to substantial degradative processes.

Although endogenous cellular enzymes are responsible for the majority of degradative processes, the analyte will always tend to hydrolyse spontaneously during storage or processing and this process is largely dependent on the storage conditions such as temperature, water content, pH, light and stability and molecular weight of the analyte molecule but may also be dependent on the quality of the reagents used.

One of the most common and simple approaches for successful storage is to reduce the temperature of the biological sample. Generally samples are stored at temperatures below room temperature (20-24° C.); protein solutions at 4° C. or −20° C., nucleic acids in freezers at −20° C. or −80° C., in dry-ice or in liquid nitrogen. Anti-microbial agents such as sodium azide may be added to control microbial growth.

It is well known that RNA is particularly sensitive to degradation by enzymes, spontaneous hydrolysis, divalent metal cation catalysed hydrolysis, alkali sensitivity and cross-linking in FFPE (formalin-fixed paraffin-embedded) samples. Many metal solutions such as lead, magnesium and manganese are very destructive to RNA and are indeed essential for not only ribozyme but also nuclease activity such as DNase I, mung bean nuclease and S1 nuclease. Iron (2+) has been implicated in the oxidation of nucleobases as part of the Fenton reaction leading to translationally impaired rRNA and mRNA (Honda et al., (2005) J. Biol. Chem. 280, 20978-20986), for example the conversion of guanine to 8-oxo-guanine. Other possible catalytic roles of metal ions in enzymatic and nonenzymatic cleavages of phosphodiester bonds have been reviewed (Yarus, M. (1993) FASEB J. 7, 31-39). Indeed chelators such as EDTA and EGTA are frequently added to RNA or RNA lysis solutions for the purpose of reducing RNA degradation by removing metal ions. Ribonucleases ("RNases") are a large group of ubiquitous enzymes associated with many sources including microbes, human skin, dust and the content of cells and tissues. They are also readily released from intra-cellular vesicles during freeze-thawing. Certain tissues including the pancreas are known to be particularly rich in RNase A. RNase A is one of the most stable enzymes known, readily regaining its enzymatic activity following, for example, chaotropic salt denaturation making it extremely difficult to destroy. A high concentration of chaotrope such as guanidine (4-6M) is required to destroy RNase activity (Thompson. J. and Gillespie. D. Anal Biochem. (1987) 163:281-91).

There are several methods for inhibiting the activity of RNases such as using; (i) ribonuclease peptide inhibitors ("RNasin") an expensive reagent only available in small amounts and specific for RNase A, B and C, (ii) reducing agents such as dithiothreitol and β-mercaptoethanol which disrupt disulphide bonds in the RNase enzyme, but the effect is limited and temporary as well as being toxic and volatile, (iii) proteases such as proteinase K to digest the RNases, but the transport of proteinases in kits and their generally slow action allows the analyte biomolecules to degrade, (iv) reducing the temperature to below the enzyme's active temperature; commonly tissue and cellular samples are stored at −80° C. or in liquid nitrogen, (v) anti-RNase antibodies, (vi) precipitation of the cellular proteins including RNases, DNA and RNA using solvents such as acetone or kosmotropic salts such as ammonium sulphate, a commercialised preparation of ammonium sulphate is known as RNAlater™ (Sigma-Aldrich, USA; LifeTechnologies, USA; Qiagen, Germany), (vii) detergents to stabilise nucleic acids in whole blood such as that found in the PAXgene™ DNA and RNA extraction kit (PreAnalytix, Germany), (viii) chaotropic salts, (ix) alcohols such as those found in the PAXgene™ Tissue stabilisation reagent (PreAnalytix, Germany). A range of such chaotropic mixtures are set out in RNA Isolation and Analysis, Editor. Jones (1994) Chapter 2.

The primary goal of sample storage is to minimise any changes to the analyte biomolecule that may be introduced as a result of the pre-analytical procedure and sample purification so that the analytical result resembles as closely as possible the original in vivo complexity and diversity of the biomolecules, thereby improving assay accuracy, sensitivity and specificity. Whilst there are various methods and products that are available to reduce pre-analytical variation, all suffer from various drawbacks making their use problematic or sub-optimal. Procedures that are effective at stabilising one class of biomolecules are often ineffective at stabilising others so that the technician is obliged to choose a specialised reagent and procedure for each biomolecule analyte. For example the PAXgene™ system (PreAnalytix) (U.S. Pat. Nos. 6,602,718 and 6,617,170) can be used for nucleic acids but not proteins and requires lengthy purification steps with multiple wash buffers, whilst cocktails of protease inhibitors help to protect proteins from degradation but not nucleic acids. The PAXgene™ tissue stabilisation kit requires two separate treatments of the tissue and involves toxic and flammable chemicals. RNAlater™ treatment of tissues reduces their utility for immunohistochemistry, histology and increases tissue hardness without fully protecting the RNA, nevertheless it has been adopted as the gold standard for RNA preservation.

It is not always possible to purify RNA at the time or site where the sample is extracted, for example a biopsy from a hospital operating theatre or a blood sample from a doctor's office. In these cases, the sample must be very carefully stored prior to RNA extraction, which might be carried out within as little as 30 minutes but would more commonly occur only after several hours or days following processing by the hospital pathology laboratory. Often the time and temperature of the pre-analytical step is poorly recorded leading to ambiguous knowledge of the quality of the sample. As a consequence, it has been necessary to develop separate sample storage conditions for each type of tissue and final use of the RNA. As already stated this generally involves using either a dedicated stabilisation solution such as RNAlater or PAXgene or immediately freezing the sample in liquid nitrogen. At least in the case of the PAXgene stabilisation reagent, incomplete removal of the stabiliser will negatively impact RNA yields during purification (PAXgene Blood RNA Kit Handbook, June 2005).

Tissue storage may be effected by tissue fixation using a fixative. 'Fixation' refers to increasing the mechanical strength, hardening, preserving and increasing stability of the treated biological sample such as fresh cells, biopsy or tissue, and maintains the sample in a state as similar as possible to that of the original fresh sample in situ, in its natural state. Fixation is commonly used in pathology, histology, histochemistry, cytochemistry, anatomical studies and studying cells, and generally precedes additional steps such as storage, embedding, staining, immunohistochemistry and/or immunocytochemistry. The process of fixation ideally inhibits enzymes such as nucleases and proteases, stops microbial growth on the sample and maintains both gross tissue morphology as well as cellular ultrastructure such as golgi, nucleus, endoplasmic reticulum, mitochondria, lysosomes and cytoplasmic membranes. As one example, the preservation of the correct cell morphology is important for a pathologist to diagnose the presence, type and grade of cancer in a patient, but in order to do this correctly the sample must also be capable of becoming correctly stained or labelled with antibodies for immunohistochemistry. Commonly the sample is treated with a 1-5% aqueous buffered solution of formalin (formaldehyde) paraformaldehyde or glutaldehyde for 1-24 hours at room temperature in order to allow cross linking of proteins and other cellular components and then, following tissue sectioning, stained with Haematoxylin and Eosin stain (H&E). Although glutaraldehyde can also be used its rate of penetration into the tissue is slower than with formaldehyde (which penetrates at approximately 1 mm per hour when 18-20 volumes are added relative to the tissue volume). Whilst RNA can also be preserved in this manner, in general it becomes highly degraded during or after formalin fixation making gene expression analysis highly problematic and artifactual. One specific problem is that the RNA analyte becomes cross-linked with other biomolecules such as proteins so that they subsequently need to be released prior to analysis, this process is generally very harsh requiring extended periods at elevated temperatures which leads to significant RNA degradation. Another problem of fixation is maintaining soluble analytes such as RNA and proteins in the cell so they can be integrated by for example, in situ hybridization or immunohistochemistry. Yet another problem with formalin fixation in particular is that the covalent modification of the cellular proteins results in the loss of antigenic immunorecognition which can render immunohistochemistry techniques difficult or impossible depending on the antibody. As one further example, formalin fixed tissues are routinely embedded in paraffin wax to allow the tissue block to be thinly sliced and examined microscopically (FFPE). Other common tissue fixation methods involve using methanol, ethanol or acetone that result in protein precipitation rather than cross-linking. Methods to fix tissues, maintain good RNA quality whilst allowing immunohistochemical staining are particularly needed. It is well known that commonly used fixatives such as formaldehyde, paraformaldehyde, gluataldehyde and methanol are highly toxic potential carcinogens, whilst ethanol and acetone are highly flammable. The ideal fixative should work on a wide variety of tissues including neural, lymphoid and fatty, preserve large pieces of tissues, and be compatible with immunohistochemical, histochemical and in situ hybridisation and other specialised techniques. It should also be compatible with automated tissue fixation procedures. A review with detailed protocols has been published by Bancroft (2008) 'Theory and Practice of Histological Techniques' and by Stanta (2011) 'Guidelines for Molecular Analysis in Archive Tissues' whilst representative examples of fixed and stained tissues can be found in Ross and Pawlina (2011) 'Histology A Text and Atlas'.

SUMMARY OF THE INVENTION

In one aspect, the present invention provides the use of a deep eutectic solvent to inhibit the degradation of a biomolecule.

It has surprisingly been discovered that it is possible to stabilise biomolecules such as RNA, DNA and proteins in biological samples with deep eutectic solvents (DES). It has also been discovered that DES mixtures can be used to fix and preserve cell morphology in biological samples such as tissue blocks, cancer biopsies and whole blood. This invention describes methods to stabilise and preserve biomolecules, whole cells, tissues and biological samples using DES mixtures. The sample or tissue may comprise a solid tissue or non-solid tissue.

We have surprisingly found that many DES mixtures are capable of stabilising and preserving RNA, other biomolecules such as protein and DNA, cells and tissue structures. Using individual DES components alone in aqueous solution such as Choline chloride (6M) or Urea (5M) does not provide for either RNA stabilisation or cell fixation, only when the components are combined in a DES such as Choline chloride:Urea do they preserve and stabilise. (Table 1). We have found for example only, that the mixture of Choline chloride with Trifluoroacetamide is particularly effective at stabilising RNA in cells whilst maintaining cell morphology. We have also found that the mixture of Choline chloride with sorbitol is particularly effective at stabilising RNA in whole tissues. However an extremely large number of other combinations and ratios of DES components are useful to practice this invention.

The separation of components of mixtures by natural ionic liquids and natural DES's has been reported (WO 2011/155829) but the effect of DES on the stabilisation of biomolecules or cells has not been reported. Indeed in US 2009/0117628A1 it has been shown that enzymatic reactions may be carried out in a DES, and that «a variety of enzymes reactions are active in a variety of DES's», indicating that nucleases and proteases and other catabolic enzymes would be equally active. Surprisingly we have found that RNA and other biomolecules are stabilised in DES mixtures and cell morphology is fixed demonstrating that the cytoskeleton is also stabilised.

DES's are mixtures of two or more components that when combined together have a eutectic point, which is the temperature of solidification or freezing (Fp). The eutectic point of the combined components is generally much lower than either of the components individually or at any other ratio of mixing and occurs at a single temperature without separation of the individual components on solidification. The properties of DES's have been described in A. P. Abbott, G. Capper, D. L. Davies, R. K. Rasheed, V. Tambyrajah, Chem. Commun. 7 (2003) 70-71, A. P. Abbott, D. Boothby, G. Capper, D. L. Davies, R. K. Rasheed, J. Am. Chem. Soc. 126 (2004) 9142-9147, [7] G. Imperato, E. Eibler, J. Niedermaier, B. Konig, Chem. Commun. 9 (2005) 1170-1172, S. Gore, S. Baskaran, B. Koenig, Green Chem. 13 (2011) 1009-1013, J. T. Gorke, F. Srienc, R. J. Kazlauskas, Chem. Commun. 10 (2008) 1235-1237, A. P. Abbott, J. Collins, I. Dalrymple, R. C. Harris, R. Mistry, F. Qiu, J. Scheirer, W. R. Wise, Aust. J. Chem. 62 (2009) 341-347, Y. H. Choi, J. van Spronsen, Y. Dai, M. Verberne, F. Hollmann, I. W. C. E. Arends, G. J. Witkamp, R. Verpoorte, Plant Physiol. 156 (2011) 1701-1705, and reviewed by Zhang Q, De Oliveira Vigier K, Royer S, Jerome F. Chem Soc Rev. 2012 Nov. 7; 41(21):7108-46.

Industrially DES's have been used for electrochemical plating, mining applications and drill lubricants (US2009/0247432), industrial enzyme applications (US2009/0117628A1), preparation of inorganic compounds (D. Freudenmann, S. Wolf, M. Wolff and C. Feldmann, Angew. Chem., Int. Ed., (2011), 50, 11050-11060) or organic compounds (S. Gore, S. Baskaran and B. Koenig, Green Chem., (2011), 13, 1009-1013), biological extractions (WO 2011/155829), in electrochemistry as electrolytes for dye-sensitized solar cells and metal electropolishing (H.-R. Jhong, D. Shan-Hill, C.-C. Wan, Y.-Y. Wang and T.-C. Wei, Electrochem. Commun., (2009), 11, 209-211), electrodeposition (E. Gomez, P. Cojocaru, L. Magagnin and E. Valles, J. Electroanalytical Chem., (2011), 658, 18-24), purification of biodiesel (K. Shahbaz, F. S. Mjalli, M. A. Hashim and I. M. AlNashef, Energy Fuels, (2011), 25, 2671-2678), solubilisation of drugs (H. G. Morrison, C. C. Sun and S. Neervannan, Int. J. Pharm., (2009), 378, 136-139), solubilisation of metal oxides (A. P. Abbott, D. Boothby, G. Capper, D. L. Davies and R. K. Rasheed, J. Am. Chem. Soc., (2004), 126, 9142-9147) and solubilisation of $CO_2$ (X. Li, M. Hou, B. Han, X. Wang and L. Zou, J. Chem. Eng. Data, (2008), 53, 548-550). Van Spronsen et al. sets out the use of DES's of natural origin such as various combinations of amino-acids, sugars and carboxylic acids for extraction in WO2011/155829 but does not mention their use for stabilisation or cell and tissue fixation. The DES's described are for extraction purposes rather than stabilisation and fixation.

DES's are not considered to be ionic liquids because (i) they are not entirely composed of ionic species and (ii) they can also be obtained from non-ionic species, (iii) they are mixtures and not compounds. As compared to the traditional ionic liquids, DES's derived from, for example, Choline chloride have several advantages such as (1) low cost, (2) chemically inert to water, (3) easy to prepare by simply mixing two or more components, (4) most are biodegradable and non-toxic, (5) low volatility even when heated and (6) non-flammable. All DES's are liquids below 150° C. and many are liquid between room-temperature and 70° C., with a few notable examples that are liquid below 0° C.

Frequently a DES is obtained by mixing a quaternary ammonium halide salt with a metal salt such as $ZnCl2$ or a hydrogen bond donor such as Urea, that has the ability to form a complex with the halide anion of the quaternary ammonium salt. However it has been found that there are also exceptions such as when there is no halide anion present in the DES as in Betaine:Trifluoroacetamide. As used herein, the term "betaine" refers to N,N,N-trimethylglycine, unless otherwise specified.

The deep eutectic solvents discussed herein may include a component having a quaternary ammonium group.

The component having a quaternary ammonium group may be a zwitterionic component further comprising a carboxylate group. A preferred zwitterionic component is betaine (N,N,N-trimethylglycine).

Alternatively, the component including a quaternary ammonium group may be in the form of a salt with an appropriate counterion. The counterion is suitably a halide, and is preferably chloride, bromide or iodide, most preferably chloride. Other suitable counterions include nitrate, tetrafluoroborate, and the like. When the component is in the form of a salt, the counterion preferably does not comprise a carboxylate group.

In a further aspect, the present invention provides a method for stabilising RNA in an RNA-containing sample, which method comprises contacting the sample with a DES containing mixture to form a stabilised RNA-containing composition.

In a further aspect, the present invention provides a method for stabilising DNA in a DNA-containing sample, which method comprises contacting the sample with a DES containing mixture to form a stabilised DNA-containing composition.

In a further aspect, the present invention provides a method for stabilising proteins including phosphoproteins in a peptide-containing sample, which method comprises contacting the sample with a DES containing mixture to form a stabilised protein-containing composition.

In a further aspect, the present invention provides a method for fixing a cell's native morphology, and stabilising RNA, DNA and/or proteins, in a bacterial, fungal, animal or plant sample, such as E. coli, Yeast, Nematode, *Drosophila*, Zebra fish, Mouse, Rat, *Arabidopsis thaliana*, Rice, Wheat, Maize, Tobacco and/or Potato.

In a further aspect, the present invention provides a method for fixing and stabilising a cell's native morphology, in a cell containing sample, such as an organ, tissue, biopsy, circulating tumour cell (CTC), blood sample, plasma sample, serum sample, tissue culture cells, saliva, urine, cerebral spinal fluid, medical sample, egg, embryo, or adult tissue, or FFPE sample, which method comprises contacting the cell containing sample with a DES containing mixture to form a fixative and stabiliser of cell structure and morphology compatible with cell counting, CTC detection, immunohistochemistry, histochemistry, staining and colouration, flow cytometry, mass spectrometry, in situ hybridisation, laser capture microdissection and molecular analyses of for example RNA, DNA and/or proteins.

In a further aspect, the present invention provides a method for fixing and stabilising a cell's native morphology, in a cell containing sample, whereby the protein content and protein cellular localisation can be determined by use of a colourant, an antibody or an aptamer, which method comprises contacting the cell containing sample with a DES containing mixture to form a fixative and stabiliser of cell structure and morphology and at the same time or subsequently the sample is contacted with a colourant, an antibody or an aptamer.

In a further aspect, the present invention provides a method for fixing and stabilising a cell's native morphology in a cell containing sample, whereby the RNA content and its cellular localisation can be determined by use of a labelled or unlabelled probe such as an oligonucleotide, a primer, a PNA, a LNA, a DNA, a bDNA or RNA sequence, a natural or synthetic complementary nucleic acid sequence, which method comprises contacting the cell containing sample with a DES containing mixture to form a fixative and stabiliser of cell structure and morphology and at the same time or subsequently contacting the sample with a natural or synthetic hybridising sequence for molecular analysis.

In a further aspect, the present invention provides a kit for stabilising RNA, DNA and/or protein in a biological sample, which kit comprises at least one container containing a DES mixture. The kit further comprising instructions for contacting the sample with a DES mixture whereby the RNA, DNA and/or protein in the biological sample is stabilised against degradation.

In a further aspect, the present invention provides a kit for stabilising cell structure in a biological sample, which kit comprises at least one container containing a DES mixture. The kit further comprising instructions for contacting the sample with a DES mixture, whereby the DES mixture serves as a fixative and/or stabiliser of the cell structure for microscope and/or histological studies such as staining and colouration, ISH and/or IHC.

In a further aspect, the present invention provides a kit for fixing cell and tissue structures and morphology in a biological sample, which kit comprises at least one container containing a DES fixative and/or stabilising mixture and optionally wherein the container is permeable and of maximum height of 10 mm into which the sample is immersed and fixed and/or stabilised. The walls of the permeable container can be a sieve or grating or provided with slits allowing initial passage and access of the DES mixture to the cell or tissue sample, and/or subsequent contact with liquid paraffin.

In a further aspect, the present invention provides use of a combination of a DES mixture with an additive to function as a fixative and stabiliser of biomolecules including RNA, DNA and/or proteins.

In a further aspect, the present invention provides a stabilised RNA-containing composition, which comprises RNA and a DES mixture.

In a further aspect, the present invention provides a stabilised DNA-containing composition, which comprises DNA and a DES mixture.

In a further aspect, the present invention provides a stabilised protein-containing composition, which comprises protein and a DES mixture.

In a further aspect, the present invention provides use of a DES mixture as a stabiliser of cell structure and/or tissue histology and/or morphology, and a stabiliser of RNA, DNA and/or proteins.

In a further aspect, the present invention provides use of a DES mixture as a stabiliser of cell structure and/or tissue histology and/or morphology, for subsequent embedding in paraffin and microtome sectioning, and optionally staining, in situ hybridisation and/or immunohistochemistry.

In a further aspect, the present invention provides use of a DES mixture as a stabiliser of cell structure and/or tissue histology and/or morphology, for subsequent frozen cryostat sectioning, and optionally staining, in situ hybridisation and/or immunohistochemistry.

In a further aspect, the present invention provides use of a DES mixture as a stabiliser of cell structure and/or tissue histology and morphology, for subsequent laser capture microdissection (LCM) and optionally recovery of protein, DNA and RNA.

In a further aspect, the present invention provides use of a DES mixture as a stabiliser of biomolecules and/or cells in plasma, serum and blood for subsequent diagnostic analysis including circulating tumour cells and/or white blood cells and/or whole blood including cell capture, counting and/or typing, staining and/or colouration, mass spectrometry, in situ hybridisation and/or immunohistochemistry. Optionally recovery of protein, DNA and RNA can be carried out.

In a further aspect the present invention provides use of a DES mixture as a stabiliser of exosomes, other types of vesicles, microvesicles, sub-cellular bodies and particles such as micelles, liposomes, endosomes, cell debris, cell membranes, cell nuclei, cytoplasmic components such as an endocytic compartment, golgi, endoplasmic reticulum and/or mitochondria. It further relates to stabilising RNA, DNA and/or proteins contained within exosomes derived from blood, serum, plasma, urine, cerebral spinal fluid and other bodily fluids for storage, transport and handling for a diagnostic test such as extraction, analysis and/or identification of miRNA or mRNA contained within an exosome or other extracellular microvesicle.

In a further aspect the present invention provides use of a DES mixture as a stabiliser of pre-purified particles and molecules such as viral particles, bacteriophages, RNA, DNA, proteins such as enzymes and antibodies, lipids and fats and/or carbohydrates. Pre-purified is defined here as a sample consisting of greater than 80% of the particle or molecule of interest.

In a further aspect, the present invention provides use of a DES mixture as a stabiliser of biomolecules, bacteria, fungal and/or other pathogens such as *Leishmania, Trypanosoma* and/or *Plasmodium* in plasma, serum, buffy coat and/or blood for subsequent pathogen diagnostic analysis including bacterial and/or viral diagnostics.

In a further aspect, the present invention provides use of a DES mixture as a stabiliser of viruses, viral particles, viral nucleic acids and/or proteins such as Influenza, HPV, HIV, HBV, HCV, Foot and Mouth Disease Virus, Influenza, SARS and/or West Nile Virus, in biological samples such as sputum, a swab, plasma, serum, buffy coat and/or blood for subsequent viral diagnostic analysis.

In a further aspect, the present invention provides an apparatus suitable for cell or tissue fixation and/or for inhibiting the degradation of a biomolecule, which apparatus comprises: a first deep eutectic solvent layer formed of a first deep eutectic solvent; and a recess in the first deep eutectic solvent layer for receiving a sample comprising the biomolecule wherein the first deep eutectic solvent is a solid or a gel. The apparatus may further comprise a second deep eutectic solvent layer formed of a second deep eutectic solvent, wherein the second deep eutectic solvent layer encloses the recess; and wherein the second deep eutectic solvent is a solid or a gel.

The first and/or second deep eutectic solvent may be a deep eutectic solvent as defined herein and preferably comprises a component selected from 3,3,3-trifluoropropanamide, 2,2-difluoro-2-phenylacetamide, urea and thiourea.

The first and/or second deep eutectic solvent may also comprise a component selected from choline chloride, butyrylcholine iodide, and N,N,N-trimethylglycine.

The apparatus suitable for cell or tissue fixation and/or for inhibiting the degradation of a biomolecule according to the invention comprises a first deep eutectic solvent layer formed of a first deep eutectic solvent. The first deep eutectic solvent is a solid or a gel. Suitably, the components of the deep eutectic solvent are selected such that the deep eutectic solvent is solid under the desired conditions of use, for example, at a temperature of about 25° C. and a pressure of about 1 atm. Alternatively or additionally, the deep eutectic solvent may be blended with a matrix material which is a solid or a gel under the desired usage conditions.

Particularly preferred deep eutectic solvents for use as the first deep eutectic solvent include choline chloride:3,3,3-trifluoropropanamide, optionally in a molar ratio of about 1:2; choline chloride:2,2-difluoro-2-phenylacetamide, optionally in a molar ratio of about 1:1; choline chloride:trehalose, optionally in a molar ratio of about 1:1 and butyrylcholine iodide:urea, optionally in a molar ratio of about 1:2.

If the apparatus comprises a second deep eutectic solvent, the first and second deep eutectic solvents may be the same or different. Preferably, the second deep eutectic solvent is selected from choline chloride:3,3,3-trifluoropropanamide, optionally in a molar ratio of about 1:2; choline chloride:2, 2-difluoro-2-phenylacetamide, optionally in a molar ratio of about 1:1; choline chloride:trehalose, optionally in a molar ratio of about 1:1; and butyrylcholine iodide:urea, optionally in a molar ratio of about 1:2.

In a further aspect, the present invention provides a kit wherein the deep eutectic solvent is a deep eutectic solvent as defined herein.

The invention is not limited particularly to the stabilisation of any one type of biomolecule, but the improvement of the quality and integrity of RNA is often notable as it is one of the most fragile molecules in the cell due to its length and chemical sensitivity to environmental aggression. Generally as a rule of thumb it can be considered that if the rRNA molecules of the cell are intact then the mRNA, DNA, proteins, lipids, carbohydrates and small metabolites will also be intact, however if the rRNA is degraded the other biomolecules may or may not also be degraded depending on the particular chemical sensitivity of each biomolecule. There are some exceptions such as if the tissue or cell is particularly rich in certain enzymes such as RNases, DNases, lipases, esterases, proteases or phosphatases which will lead to specific degradation or modification of one particular class of biomolecules.

The RNA referred to can be found, derived or associated with a sample such as a virus, cell, circulating tumour cell, cerebrospinal fluid, bronchoalveolar lavage, serum, plasma, blood, exosomes, other microvesicles preserved samples such as FFPE blocks or sections, biopsies, solid or liquid tissues or other biological samples. It can also be a nucleoside or nucleotide containing molecule such as a cAMP, ATP, GTP, monomers, dimers and oligomers of deoxy- and ribonucleotides, deoxy- or ribo-oligonucleotides, plasmid DNA, genomic DNA, mitochondrial DNA, RNA such as microRNA (miRNA), piRNA, siRNA, tRNA, viriods, circulating RNA, circular ss or ds non-coding RNA, hnRNA, mRNA, rRNA such as the 5S, 5.8S, 16S, 18S, 23S and 28S rRNA species, and viral RNA derived from for example HCV, West Nile Disease Virus, Foot and Mouth Disease Virus, Influenza, SARS, or HIV RNA, and/or extracellular RNA (exRNA).

It can also be a molecule derived from a synthetic organic procedure such as an oligo-synthesizer, a mixture of RNA and DNA, a chimera of RNA and DNA, the product of an enzymatic reaction such as an in vitro RNA transcription, amplified RNA (aRNA), ribozymes, aptamers, a PCR amplification, rolling circle amplification (RCA) or ligase chain reaction (LCR) an internal control standard or control RNA.

RNA analysis methods that would benefit from this invention include in vitro or in vivo protein translation of mRNA templates, RNA dependent RNA polymerisation, DNA dependent RNA polymerisation, RNA splice analysis, RNA folding analysis, aptamer and ribozyme production, optical density (OD) measurements, RNA:protein interaction studies, RNA electrophoresis and sedimentation including molecular weight standards, RNA bioconjugates, RNA ligation, RNA folding studies, RNA footprinting, RNA NMR structural studies, RNA oligonucleotide synthesis, RNA in situ, in situ hybridization (ISH), fluorescence in situ hybridization (FISH), RNA sequencing, reverse transcription (RT), RT-PCR, RT-qPCR, nuclease protection assays, hybridisation techniques such as northern blotting, bDNA, and microarrays including the preparation of probes, fluorescent nucleic acid labelling, NASBA, RNAi, miRNA techniques such as extraction and quantification and those methods requiring quality control and/or quantitative or qualitative measurements of RNA.

Instability refers to an alteration in the molecular weight or an alteration of the chemical structure of the RNA molecule, such instability is associated with handling, storage, transport and/or the actual analysis of the analyte molecule. Biomolecule instability is often dependent on the activity of naturally occurring catabolic enzymes and in particular RNases which can substantially alter the molecular weight of the RNA or involve much smaller molecular weight alterations of the original analyte molecule. Such RNases can have an origin either in the biological sample itself, for example they can be released progressively following sample handling or released massively as a result of poor handling of the tissue when for example it has been freeze thawed, a process that generally leads to the rupture of intra-cellular vesicles containing proteases and nucleases that consequently flood into the cytoplasm leading to very high rates of analyte degradation. Alternatively, the degradative enzyme can come from external contamination of the sample environment such as microbial contamination or spoilage of the sample. Analyte instability is generally associated with a reduction in the sensitivity or performance of the analytical procedure, whether the analyte is a protein, nucleic acid, carbohydrate, lipid or metabolite.

'Degradation' refers to the physical or chemical changes that occur as a consequence of biomolecule and/or analyte instability. As some examples of degradation related to nucleic acids, degradation can refer to the deamination of nucleobases such as the conversion of cytosine to uracil, oxidation of nucleobases such as guanine, the loss of methyl groups from methyl-cytosine, the loss of one or more nucleobases such as occurs during depurination, the cleavage of phosphodiester bonds leading to chain cleavage and the loss of one or more nucleotides from the bulk of the nucleic acid molecule. It does not refer only to changes of the secondary or tertiary structure of the molecule.

'Integrity' refers to the intactness of a molecule and therefore is the opposite of degradation.

'Substantial degradation' refers to a sample that contains at least half of the analyte molecules that have been cleaved or reduced in molecular weight by 5% or more. Methods to determine degradation are well known and depend on the analyte molecule (see Sambrook et al., (1989) Molecular Cloning: A Laboratory Manual (2nd Ed.) Cold Spring Harbor University Press, NY). The determination of the molecular weight and therefore the extent of degradation of nucleic acids is commonly carried out using denaturing or native gel electrophoresis and may include Southern or Northern blotting with a labelled hybridisation probe. RNA quantification can include analysis using an RNA Chip and the Agilent Bioanalyser 2100™ system and calculating the 'RNA Integrity Number' (RIN). Nucleic acid degradation can also be conveniently quantified by Q-PCR for DNA, and RT-qPCR for RNA using for example a Lightcycler™ (Roche) and suitable amplification probes. Calculating the RT-qPCR amplification ratios of 3'/5' ends of an mRNA, frequently β-actin, following reverse transcription using an oligo dT primer is also commonly used to assess RNA degradation. Other methods include RNAseq of the entire mRNA content of a cell or tissue, or comparing the relative hybridisation signals of oligonucleotides representing 3' to 5' sites of mRNA following analysis using Affymetrix® GeneChips®. Smaller single or double stranded nucleic acids of less than 100 nucleotides in length such as oligonucleotides and miRNA are most accurately quantified by mass spectrometry such as MALDI-TOF MS, this technique having the added advantage of being able to also determine degradation events that do not significantly alter the molecular weight of the analyte such as depurination or deamination of nucleobases. Most miRNA analyses are carried out by dedicated RT-qPCR. Despite the sophistication of the methods for determining the extent of RNA degradation, it is evident that certain mRNA sequences are far more sensitive to degradation that others and because the 18 and 28S rRNA are relatively stable to degradation, they are only a poor surrogate marker for the extent of mRNA degradation. Accurately analysing mRNA degradation is currently best carried out using RT-qPCR as explained above. For a detailed description of methods to evaluate RNA degradation as a result of RNA purification methods see Muyal et al., (2009) Diag. Path. 4:9.

A 'pure sample' of RNA or DNA refers to a nucleic acid solution in water where the OD260/280 ratio is 1.7 or above.

Although generally instability and degradation are associated with a reduction in the overall molecular weight of the molecule under study ("the analyte"), it can, conversely, be related to an increase in the molecular weight of a complex that progressively aggregates during, for example, storage. One example of the latter would be the complexation or aggregation of proteins onto nucleic acids during storage of a whole tissue or the chemical cross-linking of molecules during the processing of a sample such as with formalin fixed paraffin embedded tissue ("FFPE").

'Stabilisation' refers to conditions that lead to an overall reduction in the amount of degradation of an analyte molecule compared with the control. Such a control can be the conditions used without the use of the invention, for example storage without any stabilizer (FIG. 11), but the rate of RNA degradation is generally too high to be a useful comparison, therefore a better control is the commercially available RNAlater used according to the manufacturer's instructions (Cat. No. 76106, Qiagen, Germany). The control may be an excised piece of tissue such as a biopsy, a blood or serum sample or a piece of tissue stored in RNAlater at for example 4, 20 or 37° C. for 1-16 Hrs, or 1-45 days.

Tissue disruption refers to the process of breaking a large tissue sample up into particles that are small enough to be consequently lysed by the addition of a chaotrope solution. The disruption breaks the sample up into pieces small enough to allow efficient release of the analyte for consequent RNA extraction and purification.

An 'RNase inactivation' step can be carried out to sufficiently inactivate RNase and allow subsequent stabilisation with a DES mixture without a significant degradation of the RNA. Numerous methods are known in the art for inactivating RNases such as enzymatic degradation with proteases such as trypsin, chymotrypsin, papain or proteinase K, reduction of the disulphide bond with β-mercaptoethanol (Chirgwin, et al., "Isolation of Biologically Active Ribonucleic Acid from Sources Enriched in Ribonuclease," Biochemistry, 18:5294-5299, 1979), dithiothreitol, dithioerythritol, glutathione or TCEP, addition of RNasin protein (Life Technologies, USA), RNAsecure™ (Life Technologies, USA), treatment with a chaotrope such as guanidine HCl, guanidine thiocyanate (Chomczynski and Sacchi, "Single Step Method of RNA Isolation by Acid Guanidine Isothiocyanate-Phenol-Chloroform Extraction," Anal. Biochem., 162:156-159, 1987; Sambrook, et al., "Molecular Cloning, A Laboratory Manual," pp. 7.16-7.52, 1989), urea, formamide, formaldehyde or sodium iodoacetate, treatment with a detergent such as Tween-20, Triton X-100, NP-40, SLS, or SDS, EDTA, EGTA, sodium citrate, heat or acid denaturation, inhibition with vanadyl ribonucleoside complexes (Berger and Birkenmeier, 1979) or cross-linking with glutaraldehyde. The tissue sample is initially treated such that RNase activity is reduced to at least 50, 75 or more preferably 100% of its untreated activity prior to DES mixture treatment as set out in one of the Examples here. Residual RNase activity prior to treatment can be monitored using an RNaseAlert™ kit (Life Technologies, USA). Methods for inactivating RNases in tissues are set out in U.S. Pat. No. 6,777,210 and US Patent Application Publication Number. 2009/0286304.

By way of example, but without limitation, the DES is made by mixing, or mixing and heating, one or more component(s) which may be chosen from the group: Choline nitrate, Choline tetrafluoroborate, Choline hydroxide, Choline bitartrate, Choline dihydrogen citrate, Choline p-toluenesulfonate, Choline bicarbonate, Choline chloride, Choline bromide, Choline iodide, Choline fluoride, Chlorocholine chloride, Bromocholine bromide, Iodocholine iodide, Acetylcholine hydroxide, Acetylcholine bitartrate, Acetylcholine dihydrogen citrate, Acetylcholine p-toluenesulfonate, Acetylcholine bicarbonate, Acetylcholine chloride, Acetylcholine bromide, Acetylcholine iodide, Acetylcholine fluoride, Chloroacetylcholine chloride, Bromoacetylcholine bromide, Iodoacetylcholine iodide, Butyrylcholine hydroxide, Butyrylcholine bitartrate, Butyrylcholine dihydrogen citrate, Butyrylcholine p-toluenesulfonate, Butyrylcholine bicarbonate, Butyrylcholine chloride, Butyrylcholine bromide, Butyrylcholine iodide, Butyrylcholine fluoride, ChloroButyrylcholine chloride, BromoButyrylcholine bromide, IodoButyrylcholine iodide, Acetylthiocholine chloride, L-Carnitine, D-Carnitine, Betaine, Sarcosine, Trimethylamine N-oxide, Betaine HCl, Cetyl betaine, Cetyltrimethylammonium fluoride, Cetyltrimethylammonium chloride, Cetyltrimethylammonium bromide, Lauryl betaine, N,N-Dimethylenethanolammonium chloride, N,N-diethyl ethanol ammonium chloride, Beta-methylcholine chloride, Phosphocholine chloride, Choline citrate, Benzoylcholine chloride, Lauryl sulphobetaine, Benzyltrimethylammonium chloride, Methyltriphenylphosphonium chloride, Methyltriphenylphosphonium bromide, Methyltriphenylphosphonium iodide, Methyltriphenylphosphonium fluoride, N,N-diethylenethanol ammonium chloride, ethylammonium chloride, Tetramethylammonium chloride, Tetramethylammonium bromide, Tetramethylammonium iodide, Tetramethylammonium fluoride, Tetraethylammonium chloride, Tetraethylammonium bromide, Tetraethylammonium iodide, Tetraethylammonium fluoride, Tetrabutylammonium chloride, Tetrabutylammonium bromide, Tetrabutylammonium iodide, Tetrabutylammonium fluoride, (2-chloroethyl) trimethylammonium chloride, Terbium (III) chloride, Zinc (II) chloride, Zinc (II) bromide, Zirconium (III) chloride, Iron (III) chloride, Tin (II) chloride, Copper (II) chloride, Magnesium (II) chloride; with, one or more other component(s) that can also form a DES, including for example, but without limitation, one or more of the following chemicals chosen from the group: Urea, Formamide, Thiourea, 1-Methylurea, 1,1-Dimethylurea, 1,3-Dimethylurea, Carbohydrazide, Tetramethylurea, 1,3-bis(hydroxymethyl)urea, Benzamide, Girards Reagent T, Lactamide, Acetamide, Fluoroacetamide, Difluoroacetamide, Trifluoroacetamide, Chlorofluoroacetamide, Chlorodifluoroacetamide, Chloroacetamide, Dichloroacetamide, Dichlorofluoroacetamide, Trichloroacetamide, Bromoacetamide, Dibromoacetamide, Tribromoacetamide, Bromofluoroacetamide, Bromodifluoroacetamide, Bromochlorofluoroacetamide, Iodoacetamide, Diiodoacetamide, Triiodoacetamide, 2-Methyl-2,2-difluoroacetamide, 2-Methyl-2-fluoroacetamide, 2,2-Dimethyl-2-fluoroacetamide, 2-Ethyl-2,2-difluoroacetamide, 2-Ethyl-2-fluoroacetamide, 2,2-Diethyl-2-fluoroacetamide, 2-Propyl-2,2-difluoroacetamide, 2-Propyl-2-fluoroacetamide, 2,2-Propyl-2-fluoroacetamide, 2-Fluoropropionamide, 3-Fluoropropionamide, 2,2-Difluoropropionamide, 2,3-Difluoropropionamide, 3,3-Difluoropropionamide, 3,3,3-Trifluoropropionamide, 2-Fluoro-3,3,3-trifluoropropionamide, 2-Chloro-3,3,3-trifluoropropionamide, 2,2-Chloro-3,3,3-trifluoropropionamide, 2-bromo-3,3,3-trifluoropropionamide, 2,2-Bromo-3,3,3-trifluoropropionamide, Pentafluoropropionamide, Heptafluorobutyramide, Trimethylacetamide, 1-(Trifluoroacetyl)imidazole, N,O-Bis(trifluoroacetyl)hydroxylamine, Bistrifluoroacetamide, N-Methyl-fluoroacetamide, N-Methyl-difluoroacetamide, N-Methyl-trifluoroacetamide, N-Methyl-chlorofluoroacetamide, N-Methyl-chlorodifluoroacetamide, N-Methyl-chloroacetamide, N-Methyl-dichloroacetamide, D N-Methyl-dichlorofluoroacetamide, N-Methyl-trichloroacetamide, N-Methyl-bromoacetamide, N-Methyl-dibromoacetamide, N-Methyl-tribromoacetamide, N-Methyl-bromofluoroacetamide, N-Methyl-bromodifluoroacetamide, N-Methyl-bromochlorofluoroacetamide, N-Methyl-iodoacetamide, N-Methyl-diiodoacetamide, N-Methyl-triiodoacetamide, N-Methyl-2-methyl-2,2-difluoroacetamide, N-Methyl-2-methyl-2-fluoroacetamide, N-Methyl-2,2-dimethyl-2-fluoroacetamide, N-Methyl-2-ethyl-2,2-difluoroacetamide, N-Methyl-2-ethyl-2-fluoroacetamide, N-Methyl-2,2-diethyl-2-fluoroacetamide, N-Methyl-2-propyl-2,2-difluoroacetamide, N-Methyl-2-propyl-2-fluoroacetamide, N-Methyl-2,2-propyl-2-fluoroacetamide, N-Methyl-2-fluoropropionamide, N-Methyl-3-fluoropropionamide, N-Methyl-2,2-difluoropropionamide, N-Methyl-2,3-difluoropropionamide, N-Methyl-3,3-difluoropropionamide, N-Methyl-3,3,3-trifluoropropionamide, N-Methyl-2-fluoro-3,3,3-trifluoropropionamide, N-Methyl-2-chloro-3,3,3-trifluoropropionamide, N-Methyl-2,2-chloro-3,3,3-trifluoropropionamide, N-Methyl-2-bromo-3,3,3-trifluoropropionamide, N-Methyl-2,2-bromo-3,3,3-trifluoropropionamide, N-Methyl-pentafluoropropionamide, N-Methyl-heptafluorobutyramide, N,N-Dimethyl-2,2,2-trifluoroacetamide, N-Ethyl-2,2,2-trifluoroacetamide, N,N-Diethyl-2,2,2-trifluoroacetamide, N-(Hydroxymethyl)Trifluoroacetamide, Ethyltrifluoroacetate, Dithiothreitol, Dithioerythritol, Beta-mercaptoethanol, Penicillamine, Tiopronin, Acrylamide, Methanol, Ethanol, Propanol, Butanol, Formaldehyde, Glutaraldehyde, Taurine, Aconitic acid, Adipic acid, Benzoic acid, Citric acid, Malonic acid, Malic acid, DL-Maleic acid, Oxalic acid, Phenylacetic acid, Phenylpropionic acid, Succinic acid, Levulinic acid, Tartaric acid, Gallic acid, p-Toluenesulphonic acid, Glycine, Alanine, Valine, Leucine, Isoleucine, Serine, Threonine, Tyrosine, Cysteine, Methionine, Aspartic acid, Asparagine, Glutamic acid, Glutamine, Arginine, Lysine, Histidine, Phenylalanine, Tryptophan, Proline, Ethylene glycol, Triethyleneglycol, Glycerol, Resorcinol, Phenol, 1,2-propanediol, 1,3-propanediol, 1,4-Butanediol, 1,5-Pentanediol, 1,6-Hexanediol, 1,8-Octanediol, 1,12-Dodecanediol, m-Cresol, Imidazole, 1-Methylimidazole, 4-Methylimidazole, N-Methylpyrrolidone, N-Ethylpyrrolidone, N-Benzylpyrrolidone, 2-imidazolindone, tetrahydro-2-pyrimidione, Guanidine, Guanidine HCl, Guanidine isothiocyanate, Guanidine sulphate, Ammonium acetate, Ammonium bicarbonate, Ammonium chloride, Ammonium citrate dibasic, Ammonium formate, Ammonium iodide, Ammonium nitrate, Ammonium phosphate monobasic, Ammonium phosphate dibasic, Ammonium sulfamate, Ammonium sulfate, Ammonium tartrate dibasic, Ammonium isothiocyanate, Ammonium benzoate, Ammonium bromide, Ammonium fluoride, Ammonium hydrogensulphate, Ammonium trifluoroacetate, Ammonium thiosulphate, Adonitol, Ribitol, Rhamnose, Trehalose, D-Sorbitol, L-Sorbitol, Sorbose, Xylitol, Glucose, Sucrose, Lactose, Fructose, Maltose, Mannose, Mannitol, Arabinose, Galactose, Raffinose, Inositol, Erythritol or Xylose.

It will be appreciated that some compounds disclosed herein may be ionisable, i.e. some compounds may be weak acids, weak bases, or ampholytes. Representations of the free forms of ionisable compounds are intended to encompass the corresponding ionised forms. For example, representations of carboxylic acid groups encompass the corresponding carboxylate groups.

It should be noted that certain components such as Zinc chloride can form a DES with not only Choline Chloride but also Urea; both Choline chloride and Zinc chloride appear in the same component group above, therefore certain DES mixtures can be prepared from chemicals within the same group.

It should also be noted that the list above is non-exhaustive, and that the DES components are not particularly limited to any type of molecule or property except hydrogen-bonding between DES components is frequent but not an absolute requirement.

The deep eutectic solvents used in accordance with the present invention are preferably substantially free of organic acids. In particular, the deep eutectic solvents used in accordance with the present invention are preferably substantially free of organic acids selected from malic acid, maleic acid, citric acid, lactic acid, pyruvic acid, fumaric acid, succinic acid, lactic acid, acetic acid, aconitic acid, tartaric acid, ascorbic acid, malonic acid, oxalic acid, glucuronic acid, neuramic acid and sialic acid.

Alternatively or additionally, $R_6$, $R_7$ and $R_8$ as shown in Formulae II and III are selected such that the resulting compound does not comprise a carboxylic acid group. In a preferred arrangement, when $R_6$ is OH, $R_7$ is not carbonyl. In another preferred arrangement, when $R_7$ is —Z—C(O)$R_8$, $R_8$ is not OH.

The deep eutectic solvents used in accordance with the present invention are preferably substantially free of metal salts. In one arrangement, the deep eutectic solvents are substantially free of metal salts other than salts of zinc or zirconium. The deep eutectic solvents are preferably substantially free of $NaH_2PO_4$, $Na_2HPO_4$, $NaHSO_3$, $Na_2SO_4$, $MgCl_2$, $CaCl_2$, KCl, NaCl and Kl. If the deep eutectic solvent comprises a sugar or sugar alcohol, the deep eutectic solvent particularly preferably does not comprise a metal salt.

The deep eutectic solvents used in accordance with the present invention are preferably substantially free of sugars or sugar alcohols selected from sucrose, glucose, fructose, lactose, maltose, cellobiose, arabinose, ribose, ribulose, galactose, rhamnose, raffinose, xylose, sucrose, mannose, trehalose, mannitol, sorbitol, inositol, xylitol, ribitol, galactitol, erythritol, and adonitol. If the deep eutectic solvent comprises a metal salt, the deep eutectic solvent particularly preferably does not comprise a sugar or sugar alcohol.

It should also be noted that there is no particular maximum number of DES components in the DES mixture, for example 2, 3, 4, 5, 6, 7, 8, 9, 10 or more components can be mixed to produce a DES mixture, usually but necessarily, in integer molar ratios for example in a two component DES mixture, component 1 and component 2 can be mixed in the following ratios: 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10 (mol:mol) or for example in a three component DES mixture, component 1, component 2 and component 3 can be mixed in these ratios: 10:1:1, 9:1:1, 8:1:2, 7:1:3, 6:1:4, 5:1:5, 4:1:6, 3:1:7, 2:1:8, 1:1:9, 1:2:8, 1:3:7, 1:4:6, 1:5:5, 1:6:4, 1:7:3, 1:8:2, 1:9:1, 1:10:1 (mol:mol:mol).

The skilled artisan will understand that other ratios of mixing the components are also possible, for example 20:1 or 1:30 (mol:mol) and that the particular molar ratio leading to the eutectic point is not necessarily the optimum or desired molar ratio for the particular purpose of, for example, stabilising RNA and/or fixing cell morphology. The stabilisation activity of the DES may be related to the hydrogen bonding properties of the DES mixture. There is no particular restriction or limitation to the number of components or the ratio of mixing to make a useful DES mixture for a particular application. Additional physical properties of the DES for example viscosity or density can be modified by either adding a further component, or alternatively, by adding an 'additive' as set-out below. Some DES mixtures can be prepared using a fractional molar ratio, for example ZnCl2:urea has been prepared at 1:3.5 (mol:mol) ratio and there are again no particular restrictions to the molar ratios of component 1 and component 2, or component 1, component 2 and component 3 etc. that are used, and the optimum ratio of the components comprising the DES mixture to be used for the application, such as cell fixation, is most accurately determined empirically. By way of example only, Choline chloride/Trifluoroacetamide can be mixed in a 2:1, 1.75:1, 1.5:1, 1.25:1, 1:1, 1:1.25, 1:1.5, 1:1.75 or a 1:2 mol:mol ratio, or further fractional amounts thereof, and subsequently individually tested to determine which has the optimum RNA stabilization and/or cell fixation property.

Other factors such as the cost or toxicity may also lead the artisan to reduce the proportion of a particular component and to partially replace it with a cheaper alternative. For example only, an Acetylcholine chloride:urea (1:2 mol:mol) DES mixture can, for certain applications be partially replaced with the cheaper Choline chloride as in Acetylcholine chloride:Choline chloride:urea (1:1:4 mol:mol:mol).

It will also be apparent to the artisan that due to, for example, the presence of contaminants in the components used to make the DES, such as water, oxidation, absorption of CO2, contaminating by-products during synthesis or break-down products of one of the components, and that the desired exact ratio, for example only, of a 1:1 (mol:mol) mixture may practically mean+/−10%, but more preferably 5% and even more preferably 1% difference in the exact amount of either component 1 or component 2. As way of illustration, a 5% error could potentially give the following final molar ratios: 0.95:1, 1:0.95, 1.05:0.95 or 0.95:1.05 (mol:mol) and the effect of this error can generally only be determined empirically, for example its effect on RNA quality as set-out in Example 1. Generally in order to remove contaminants including water, the well-known procedure of recrystallisation in ethanol can be carried out followed by extensive vacuum and/or chemical drying. Methods are set-out in 'Purification of Laboratory Chemicals' Butterworth-Heinemann (2012).

Typically, but certainly not exclusively, a DES is prepared by mixing a hydrogen bond acceptor from one of the following classes of chemicals; (i) a nitrogen salt with a positively charged cation such as primary, secondary, tertiary or quaternary nitrogen, one example of a nitrogen salt is one with a halide, such as Choline chloride, (ii) a metal salt such as a transition metal salt halide, with, a hydrogen bond donor which may include (iii) an amine, (iv) a hydroxyl, (v) an aldehyde, (vi) an amide, or (vii) carboxylic acid, hydrogen bond donors such as sugars, carboxylic acids, ureas such as Trifluoroacetamide, and alcohols would thus be included.

In one arrangement, the deep eutectic solvent is a type III or a type IV deep eutectic solvent, wherein the RNA extracted from 10 mg of a rat liver sample incubated at 24° C. for 20 days with 400 mg of the deep eutectic solvent has an RNA integrity number (RIN) of at least 4.0 as measured using an Agilent Bioanalyser 2100.

RNA integrity number may be measured using an RNA 6000 Nano total RNA Kit (Cat. No. 5067-1511, Agilent Technologies, USA) and a Bioanalyser 2100 instrument (Cat. No. G2939AA, Agilent Technologies, USA)

As used herein, the term "type III deep eutectic solvent" refers to a deep eutectic solvent having at least a first component and a second component, wherein the first component is a quaternary ammonium or phosphonium compound such as choline chloride or N,N,N-trimethylglycine (betaine), and wherein the second component is a hydrogen bond donor, such as urea or trifluoroacetamide. A type IV deep eutectic solvent is a deep eutectic solvent comprising at least a first component and a second component, wherein the first component is a metal salt such as zinc chloride and wherein the second component is a hydrogen bond donor, such as urea.

A skilled artisan will be familiar with methods for extracting RNA from tissue samples. Suitably, the RNA may be extracted using an RNeasy Mini kit (Cat. No. 74106, Qiagen, Germany) in accordance with the manufacturer's instructions, although other methods may be used.

The present invention provides the use of a deep eutectic solvent as a virus, cell or tissue fixative to produce a fixed virus, cell or tissue. Preferably, at least 75% of HeLa cells grown on a substrate and incubated at 24° C. for 1 hour with the deep eutectic solvent remain attached following replacement of the deep eutectic solvent with water and incubation at 24° C. for 1 hour.

A skilled artisan will be familiar with methods for determining the number of cells which remain attached to a substrate. For example, approximately 2,000 HeLa cells could be grown on a suitable substrate, such as a coverslip. One example of suitable coverslip is a Cellattice™: Micro-Ruled Cell Culture Surface with a diameter of 25 mm (Micro-ruled cell culture coverslip surface, Cat. No. CLSS- 25D-050 Nexcelom Bioscience, USA). The substrate could be placed in a tissue culture plate and grown overnight in an appropriate buffer, such as 2 ml of DMEM/10% FBS. The number of attached cells in a defined area of the substrate may be counted manually using a 10× objective microscope lens. The tissue culture medium may be removed using, for example, an aspirating pipette and replaced with 400 mg of a deep eutectic solvent. The tissue culture may be incubated for 1 hour at room temperature to allow cell fixation and then the deep eutectic solvent removed replaced with 2 ml of distilled water, incubated for 1 hour at room temperature and the number of cells in a defined area of the grid counted manually. The percentage of attached cells remaining in the defined area compared with the original number may then be calculated.

In particularly preferred arrangements, the RNA extracted from 10 mg of a rat liver sample incubated at 24° C. for 20 days with 400 mg of the deep eutectic solvent has an RNA integrity number (RIN) of at least 4.0 as measured using an Agilent Bioanalyser 2100 and at least 75% of HeLa cells grown on a substrate and incubated at 24° C. for 1 hour with the deep eutectic solvent remain attached to the substrate following replacement of the deep eutectic solvent with water and incubation at 24° C. for 1 hour.

Optionally, the deep eutectic solvent used in accordance with the present invention is a type III deep eutectic solvent, wherein the deep eutectic solvent comprises a compound comprising a trifluoromethyl group. The compound comprising the trifluoromethyl group may be present in the deep eutectic solvent in an amount of at least 5% by weight of the deep eutectic solvent.

In one arrangement, the deep eutectic solvent comprises a first component and a second component, wherein first component is a compound of Formula I:

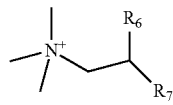

wherein:
$R_6$ is H or OH;
$R_7$ is selected from H, $CH_3$, Cl, Br, a carbonyl oxygen, and

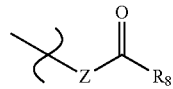

Z is selected from $—CH_2—$, O and S;
$R_8$ is $R_{11}$ or OH; and
wherein the second component comprises a compound of Formula II or a salt thereof:

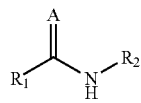

wherein:
A is selected from O, S, and NH;
$R_1$ is selected from H, an alkene group having 1 to 6 carbon atoms, $R_9$, $—NH_2$, $—NH—(CH_2)_aCH_3$, and $—C(R_3)(R_4)(R_5)$;
wherein a is 0 or an integer from 1 to 5;

$R_2$ is selected from H and linear alkyl group having 1 to 3 carbon atoms;
$R_3$ is an optionally substituted 5- or 6-membered aliphatic or aromatic ring, wherein the substituent is $R_{10}$;
$R_4$ and $R_5$ are each independently H or F; and
wherein $R_9$, $R_{10}$, and $R_{11}$ are each independently selected from alkyl groups having one to three carbon atoms, monochloroalkyl groups having one to three carbon atoms, and mono-, di- or tri-fluoroalkyl groups having one to three carbon atoms.

Preferably, in this arrangement, A is selected from O, S, and NH; R1 is selected from H, $—CH=CH2$, R9, $—NH_2$, $—NHCH3$, and $—C(R3)(R4)(R5)$; R2 is selected from H and $—CH3$; R3 is an optionally substituted 5- or 6-membered aliphatic or aromatic ring, wherein the substituent is R10; R4 and R5 are each independently H or F; and R9, R10, and R11 are each independently selected from alkyl groups having one to three carbon atoms, monochloroalkyl groups having one to three carbon atoms, and mono-, di- or tri-fluoroalkyl groups having one to three carbon atoms. Optionally, R7 is selected from H, Br, a carbonyl oxygen, and

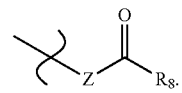

A may be O or S.
$R_2$ may be H.
$R_1$ may be selected from H, $R_9$, $—CH=CH_2$, and $C(R_3)(R_4)(R_5)$. In this arrangement, it is preferred that $R_1$ is $R_9$, wherein $R_9$ preferably has one carbon atom.

Preferably, the second component is acetamide, or 2-chloroacetamide.

In another arrangement, $R_9$ is a mono-, di- or tri-fluoromethyl group.

The second component is preferably trifluoroacetamide, trifluorothioacetamide or N-methyltrifluoroacetamide.

In another arrangement, $R_9$ has two carbon atoms, preferably wherein $R_9$ is a mono-, di- or tri-fluoroethyl group.

It is preferred that the second component is 2,2-difluoropropanamide or 3,3,3-trifluoropropanamide. In another arrangement, the second component is formamide or acrylamide.

In a further arrangement, $R_1$ is $C(R_3)(R_4)(R_5)$, wherein $R_4$ and $R_5$ are preferably F.

$R_3$ may be an optionally substituted 6-membered aromatic ring, such as an optionally substituted phenyl group. Preferably, the first component is 2,2-difluoro-2-phenylacetamide. Alternatively, $R_3$ comprises a substituent, preferably at the 2-position of the phenyl group.

The substituent is preferably a mono-, di- or tri-fluoromethyl group. Thus, in one arrangement the second component is 2-(trifluoromethyl)phenyl acetamide.

In a further arrangement $R_1$ is selected from $—NH_2$ and $—NHCH_3$. Preferably, the second component is urea, thiourea or 1,3-dimethylurea.

In a further arrangement, A is NH. In this arrangement the second component may be guanidine, optionally wherein the guanidine is present in the form of a hydroisothiocyanate salt.

In a further arrangement, $R_7$ is H. In this arrangement the first component preferably comprises choline.

In another arrangement, the first component comprises bromocholine.

In another arrangement, the first component is N,N,N-trimethylglycine, optionally wherein the second component is selected from trifluoroacetamide and urea.

In another arrangement R$_7$ is

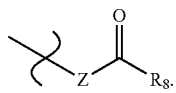

In this arrangement Z may be O or S and R$_8$ may be R$_{11}$, wherein R$_{11}$ preferably has one carbon atom.

In this arrangement the first component preferably comprises acetylcholine or acetylthiocholine.

Alternatively R$_{11}$ may have three carbon atoms, wherein the first component preferably comprises butyrylcholine.

In a further arrangement Z may be CH$_2$. In this arrangement, R$_8$ may be OH. In this arrangement, the second component is preferably carnitine.

The first component may comprise a counterion, which counterion is typically a halide anion but can be another anion such as nitrate (NO3-) or tetrafluoroborate (BF4-). The halide anion may be selected from fluoride, chloride, bromide, and iodide, preferably chloride. In this arrangement it is preferred that the first component is choline chloride, optionally wherein the second component is selected from trifluoroacetamide, trifluorothioacetamide; 3,3,3-trifluoropropanamide; 2,2-difluoro-2-phenylacetamide; thiourea and urea, preferably trifluoroacetamide.

The molar ratio of the first component to the second component is in the range 1:3 to 2:1, preferably in the range 1:1.5 to 1:2.5, more preferably 1:2.

In a further arrangement, the deep eutectic solvent comprises a first component and a second component, wherein the first component is a halide salt of choline; and wherein the second component is an optionally-substituted imidazole, wherein the or each substituent is an alkyl group having 1 to 3 carbon atoms. In this arrangement, the molar ratio of the first component to the second component is preferably in the range 2.8:1 to 2:1.

The halide salt of choline is preferably choline chloride and the substituted imidazole is preferably a methyl imidazole, such as N-methylimidazole or 4-methylimidazole. The use of benzyl-substituted imidazoles such as 1-benzylimidazole is also contemplated. Alternatively, the imidazole is unsubstituted.

In a further arrangement, the deep eutectic solvent comprises a first component and a second component, wherein the first component comprises a compound of Formula III:

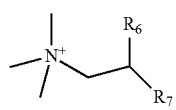

wherein:

R$_6$ is H or OH;

R$_7$ is selected from H, CH$_3$, Cl, Br, a carbonyl oxygen, and

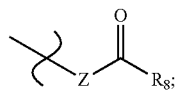

Z is selected from —CH$_2$—, O and S;

wherein R$_8$ is selected from OH, an alkyl group having one to three carbon atoms, a monochloroalkyl group having one to three carbon atoms, and a mono-, di- or tri-fluoroalkyl group having one to three carbon atoms; and wherein the second component is a sugar or a sugar alcohol having at least 3 carbon atoms.

R7 is optionally selected from H, Br, a carbonyl oxygen, and

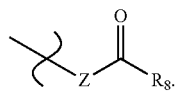

The sugar alcohol may be selected from glycerol, thrietol, xylitol, sorbitol and volemitol, preferably from glycerol, xylitol and sorbitol, and is most preferably sorbitol. Alternatively, the sugar may be trehalose.

In this arrangement, the second component may comprise choline, such as choline chloride. The molar ratio of the first component to the second component may be in the range 1:2 to 2:1, preferably in the range 1:0.8 to 1:1.2.

In a further arrangement, the deep eutectic solvent comprises a first component and a second component, wherein the first component is a zinc (II) halide or zirconium (IV) halide, and wherein the second component is a compound of Formula IV:

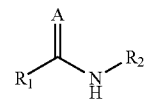

wherein:

A is selected from O, S, and NH;

R$_1$ is selected from H, an alkene group having 1 to 6 carbon atoms, R$_9$, —NH$_2$, —NH—(CH$_2$)$_n$CH$_3$, and —C(R$_3$)(R$_4$)(R$_5$);

wherein n is 0 or an integer from 1 to 5;

R$_2$ is selected from H and linear alkyl group having 1 to 3 carbon atoms;

R$_3$ is an optionally substituted 5- or 6-membered aliphatic or aromatic ring, wherein the substituent is R$_{10}$;

R$_4$ and R$_5$ are each independently H or F; and wherein R$_9$ is selected from alkyl groups having one to three carbon atoms, monochloroalkyl groups having one to three carbon atoms, and mono-, di- or tri-fluoroalkyl groups having one to three carbon atoms.

The preferred zinc (II) halide is ZnCl$_2$. The preferred zirconium (IV) halide is ZrCl$_4$. The second component is preferably urea. The molar ratio of the first component to the second component may be in the range 1:3 to 1:4.

The second component is preferably urea.

In a further arrangement, the deep eutectic solvent comprises a first component and a second component, wherein the first component is a compound of Formula V:

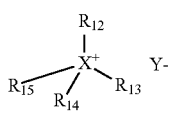

wherein:
 Y⁻ is Cl⁻ or Br⁻;
 X is N or P;
 $R_{12}$, $R_{13}$, $R_{14}$ and $R_{15}$ are each independently a linear alkyl group having 1 to 16 carbon atoms, a linear alcohol group having 1 to 16 carbon atoms, a benzyl group, or a phenyl group;
 wherein the second component is a compound of Formula I or a salt thereof:

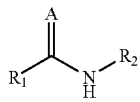

wherein:
 A is selected from O, S, and NH;
 $R_1$ is selected from H, —CH=CH$_2$, $R_9$, —NH$_2$, —NHCH$_3$, and —C($R_3$)($R_4$)($R_5$);
 $R_2$ is selected from H and —CH$_3$;
 $R_3$ is an optionally substituted 5- or 6-membered aliphatic or aromatic ring, wherein the substituent is $R_{10}$; and
 $R_4$ and $R_5$ are each independently H or F;
 wherein $R_9$ and $R_{10}$ are each independently selected from alkyl groups having one to three carbon atoms, monochloroalkyl groups having one to three carbon atoms, and mono-, di- or tri-fluoroalkyl groups having one to three carbon atoms.

Y⁻ may be Cl⁻. In alternative arrangements, Y⁻ may be any suitable counterion, such as a halide, nitrate, or tetrafluoroborate.

X may be N; in this arrangement, the compound of Formula V is a quaternary ammonium salt.

Optionally, $R_{12}$, $R_{13}$, $R_{14}$ and $R_{15}$ are each independently a linear alkyl group having 1 to 16 carbon atoms, a benzyl group, or a phenyl group $R_{12}$, $R_{13}$, $R_{14}$, and $R_{15}$ may be each independently selected from linear alkyl groups having 1 to 4 carbon atoms, and are preferably each methyl groups. In this arrangement the first component is preferably tetramethylammonium chloride.

Alternatively, $R_{12}$, $R_{13}$, $R_{14}$, and $R_{15}$ are each ethyl groups. In this arrangement the first component is preferably tetraethylammonium chloride.

Alternatively $R_{12}$, $R_{13}$, $R_{14}$, and $R_{15}$ are each butyl groups. In this arrangement the second component is tetrabutylammonium chloride or tetrabutylammonium bromide.

Alternatively, the first component comprises:

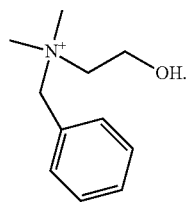

Alternatively, the first component comprises:

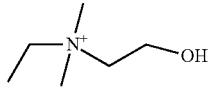

In another arrangement X may be P.

At least one of $R_{12}$, $R_{13}$, $R_{14}$, and $R_{15}$ may be a phenyl group. In this arrangement the first component preferably comprises methyltriphenylphosphonium and may be methyltriphenylphosphonium bromide.

In another arrangement A may be O or S.

$R_1$ may be selected from —NH$_2$ and —NHCH$_3$ and the second component is preferably urea. Alternatively the second component may be trifluorothioacetamide. Alternatively the second component may be trifluoroacetamide.

The molar ratio of the first component to the second component may be 1:1.5 to 1:2.5, preferably 1:1.8 to 1:2.2.

In a further arrangement the deep eutectic solvent comprises a first component and a second component, wherein the first component comprises choline and wherein the second component is an alkanediol having 5 to 7 carbon atoms. The alkanediol is preferably hexanediol.

In a still further arrangement the deep eutectic solvent comprises a first component and a second component, wherein the first component comprises choline and wherein the second component comprises an N-alkyl pyrrolidone, wherein the N-alkyl group has 1 to 5 carbon atoms. Preferably, the N-alkyl pyrrolidone is N-methylpyrrolidone. Preferably, the choline is choline chloride. In this arrangement, the molar ratio of the first component to the second component may be 1:2.

In another arrangement, the deep eutectic solvent comprises a first component and a second component, wherein the first component comprises choline, and wherein the second component comprises beta-mercaptoethanol. In this arrangement, the choline may be choline chloride and/or the molar ratio of the first component to the second component may be about 1:2.

In another arrangement, the deep eutectic solvent comprises a first component and a second component, wherein the first component comprises choline, and wherein the second component comprises dithiothreitol. The choline may be choline chloride. The ratio of the first component to the second component may be about 1:2.

DES mixtures are most simply prepared from commercialised chemical stocks available from chemical reagent companies such as Acros Organics (France), TCI (Belgium), Fluka (France) and the like. Typically the correct amounts of each component are added together in a polypropylene tube, briefly vortexed, heated to 100° C. by standard means and, if necessary for difficult to dissolve components or additives, sonicated which can be an extremely effective method of mixing. Care should be taken with components such as Choline chloride which are hygroscopic, additional drying of the stock under vacuum or by recrystallisation may be necessary. Stocks of DES mixtures can be kept dry under vacuum or by way of desiccants such as silica gel. Storage is generally at room temperature in a sealed tube.

It has also been found that treatment of plant and animal tissues with a DES mixture such as Choline chloride: Trifluoroacetamide (1:2 mol:mol) preserves the colour of leaves, flowers, blood and tissue, possibly by reducing oxidation compared with untreated samples or those treated with RNAlater, Formol or freezing. Colour preservation can be useful for the correct identification of specimens and/or components of specimens.

It has been found that the preparation of a DES mixture between Choline chloride and volatile/odorous chemicals such as Dithiothreitol, Dithioerythritol, Beta-mercaptoethanol or Phenol notably reduces the volatility and therefore the unpleasant or dangerous effects of breathing such chemicals. This effect is probably a result of hydrogen bonding between the volatile chemical and Choline chloride. There is no particular limitation as to the combination of the volatile component in the DES mixture, other than the necessity of hydrogen bonding between the components. This is also a means to reduce the loss of other volatile components such as low molecular weight alcohols, other organic chemicals such as solvents including DMSO and Formamide. The invention therefore also includes a means to reduce evaporation and/or volatility of components for storage or use in an open environment. The advantages include better health and safety, reduced loss of valuable reagents from evaporation, reduced flammability and simpler disposal.

The eutectic point of a two or more component DES mixture is the point where the proportion of component 1 relative to the other component(s) leads to the lowest melting temperature. For example the eutectic point of a Choline chloride:Urea DES mixture is (1:2 mol:mol) with a reported freezing point (Fp) of 12° C. From a practical stand-point this means that the DES can be handled as a liquid at room-temperature but will slowly solidify in the fridge. Other DES mixtures, particularly those containing Choline chloride mixed with Glycerol, Ethylene glycol and Trifluoroacetamide or Phenylacetic acid have much lower Fp, remaining liquid below 0° C. or even −20° C. Although handling liquids provides certain advantages such as ease of measuring exact volumes and mixing, it is important to note that this invention is not in any way limited to DES mixtures that are liquid at room-temperature of any other particular temperature. Heating and mixing the components of a DES provides a means for individual atoms and molecules to establish hydrogen bonds or other interactions with other atoms and molecules and therefore produce the particular property of the DES mixture. Once this has occurred, whether the DES mixture is a liquid, gel or solid does not necessarily change its capacity to, for example, stabilise RNA in a tissue sample. Simple contact between the tissue sample and the DES mixture will occur even when the DES is a solid at room temperature and rapid stabilisation can occur. Although traditionally RNA stabilisation reagents are liquids such as RNAlater, AllProtect, PAXgene Tissue or formalin, the invention described here can make use of the liquid, gel or solid DES RNA stabilisation and/or cell fixation properties. Indeed the use of a solid form of a DES can be advantageous when handling tissue samples; a solid block of DES can be formed by heating the DES solid above its eutectic point so that it melts and then pouring it into a suitable receptacle to cool and solidify or, molded or cut to fit a specific container and the tissue sample placed on the solid DES surface to bring about stabilisation. Conveniently wells, depressions or grooves can be made in the solid DES surface to serve as specific storage locations for each sample, one well receiving one sample etc, advantageously with the use of a well, the surface area in contact between the solid DES and the sample is increased (FIG. 1, left), whilst an additional layer of a DES solid or liquid above the sample located in the well will further increase the total amount of DES available and surface area of contact with the sample (FIG. 1, center). A blood collection tube is shown in (FIG. 1, right) containing a DES liquid, and with a pierceable cap for the entry of the blood by syringe needle or blood collection kit (PreAnalytix). By way of example, DES mixtures that are solid or liquid at room-temperature are set out in Table 1.

The invention also includes the use of an additive in combination with a DES mixture. The purpose of the additive is to improve the properties of the DES mixture, for example, RNA, DNA and/or protein stabilisation and/or cell and tissue fixation or another application. The effects of various additives on cell morphology for example are set out in Table 6. The purpose of the additive is to enhance the property of the DES mixture for the particular application, for example RNA stabilisation, storage, transport, and/or cell or tissue fixation. By way of example only, the additive could be a (i) colourant or dye to aid in handling or staining or processing the tissue such as H&E stain, Coomasie Blue, Methylene Blue, Xylene cyanol, Crystal violet, fuchsin, Acridine orange, DAPI, Carmine, Eosin, Ethidium bromide, Bismarck brown, Hoechst, Malachite green, Methyl green, Neutral blue, Nile blue, Osmium tetroxide, Rhodamine or Safranin, (ii) detergent, quaternary ammonium salt or saponin to improve penetration of the cell plasma membrane with the DES mixture, such as SDS, sodium lauryl sulphate (SLS), cetyltetrabutylammonium bromide (CTAB), tetrabutylammonium bromide (TBAB), sodium deoxycholate, Brij-35, Brij-58, NP-40, Triton X-100, Triton X-114, Tween-20, Tween-80, Octyl beta glucoside, CHAPS, Solanine, (iii) anti-microbial such as an antibiotic or antiseptic, such as kanomycin, streptomycin or penicillin, sodium nitrate, sodium nitrite or sodium benzoate, (iv) protein precipitant such as Trichloroacetic acid, Ammonium sulphate, Sulphosalicyclic acid, Zinc salt such as $ZnCl_2$ or $ZnSO_4$, (v) desiccant to remove excess water from the DES mixture such as Molecular sieves 4A, silica gel, $CaCl_2$ or LiCl, (vi) a probe, a hybridising complementary nucleic acid, a peptide, protein, nucleic acid or labelled molecule, an internal control, a blocking sequence or a carrier nucleic acid such as (a) ss or ds RNA or DNA sequences, (b) a peptide, enzyme or other protein such as an antibody, (c) molecules for detecting an analyte such as a biotin, horseradish peroxidase, avidin, streptavidin, fluorescent labelled molecule such as fluorescein, Texas Red, Alexa Fluor™ labelled LNA, (d) a Molecular Beacon™, a Scorpion Probe™, (vii) anti-oxidant to remove oxygen from the sample and reduce damaging oxidative effects during storage on for example the RNA or DNA nucleobases, such as Vitamin C or glutathionine, (viii) ribonuclease inhibitor such as RNasin, SUPERase•IN™, RNaseOUT™, or a protease inhibitor such as phenylmethylsulfonyl fluoride (PMSF), diisopropyl fluorophosphate (DFP), aprotinin or Pefabloc SC™, (ix) buffer to stabilise the pH between 5-8 or more preferably between 6 and 7, used in the range 0.5-20 mM such as Tris-HCl, PIPES, MES, HEPES, MOPS, MOPSO, CAPS, CAPSO, BIPES, phosphate, imidazole, (x) chelator to remove divalent metal cations, used in the range 0.5-20 mM such as BAPTA, EDTA, EGTA, citric acid, D-Penicillamine, (xi) dissolved oxygen (in the final concentration range of 2-20%), and/or $CO_2$ (in the final concentration range of 0.01-5%, a non-reactive gas such as Argon (in the final concentration range of 1-20%) and or a buffer, nutrients (such as glucose and amino-acids) to enhance cell, tissue and organism viability, and/or (xii) an alcohol in the range of 1-20% (wt:wt) to reduce DES viscosity such as a tert-butanol.

An 'additive' is defined here as any substance that can be dissolved in a particular DES mixture, and can be present in amounts greater than, equal to or less than the total amount of the DES mixture (weight:weight). By way of example only, Choline chloride:Urea:Zinc chloride (1:2:0.5 mol:mol:mol), the ZnCl2 is an additive, or Choline chloride: Trifluoracetamide:Urea (1:2:0.1 mol:mol:mol), the Urea is an additive. It should also be noted that the additive does not necessarily have any particular effect on the freezing point of the DES mixture or form hydrogen bonds with any of the DES components but endows the DES mixture with a unique property.

A non-exhaustive list of possible additives to a DES mixture are: Ammonium p-toluenesulphonic acid, Sodium p-toluenesulphonic acid, Ammonium sulphate, Ammonium chloride, Ammonium thiosulphate, Sodium dodecyl sulphate, Sodium lauryl sulphate, Sodium Benzoate, Dodecyldimethyl(3-sulphopropyl)ammonium hydroxide, Dimethylbenzene sulphonic acid, Congo Red, Giemsa, DAPI, Ethidium bromide, Mallory's stain, Orcein, Aldehyde fuchin, Osmium tetroxide, Chromium trioxide, Chromic acid, Feulgen, Dichromate, Mercuric chloride, Haematoxylin and Eosin stain (H&E), Formaldehyde, Glutaraldehyde, Acetone, Ethanol, Methanol, Methyltriphenylphosphonium bromide, Cetyltetrabutylammonium bromide (CTAB), tetrabutylammonium bromide (TBAB), sodium deoxycholate, Brij-35, Brij-58, NP-40, Triton X-100, Triton X-114, Tween-20, Tween-80, Octyl beta glucoside, CHAPS, Solanine, kanomycin, streptomycin or penicillin, sodium nitrate, sodium nitrite or sodium benzoate, ss or ds RNA or DNA sequences, ss or ds RNA or DNA labelled sequences, an aptamer, a peptide, enzyme, antibody, biotin, biotin labelled molecule, horseradish peroxidase, avidin, streptavidin, GFP or variant thereof, Luciferase, Fluorescein, Rhodamine, Texas Red, Alexa Fluor™ LNA, labelled LNA, a Molecular Beacon™, a Scorpion Probe™, FISH probe, bDNA, PCR primer, oligo (dT), PNA, anti-oxidant, RNasin, SUPERase•IN™, RNaseOUT™, phenylmethylsulfonyl fluoride (PMSF), diisopropyl fluorophosphate (DFP), aprotinin or Pefabloc SC™, Tris-HCl, PIPES, MES, HEPES, MOPS, MOPSO, CAPS, CAPSO, BIPES, phosphate, imidazole BAPTA, EDTA, EGTA, citric acid, D-Penicillamine, O2, CO2, N2, Argon, propanol, tert-butanol, Trichloroacetic acid, sulphosalicyclic acid, Water, Methanol, Ethanol, Propanol, Butanol, Tetramethyl urea, Imidazole, 1-Methylimidazole, 1-Ethylimidazole, 1-Benzylimidazole, 4-Methylimidazole, N-Methylpyrrolidone, N-Ethylpyrrolidone, N-Benzylpyrrolidone, Guanidine, Guanidine HCl, Guanidine isothiocyanate, Ribitol, Rhamnose, Trehalose, D-Sorbitol, L-Sorbitol, Sorbose, Xylitol, Glucose, Sucrose, Lactose, Fructose, Maltose, Mannose, Mannitol, Arabinose, Galactose, Raffinose, Inositol, Erythritol, Xylose, Zinc acetate, Zinc EDTA, Zinc phosphate, Zinc Trifluoroacetate, Zinc citrate, Zinc PISA, Zinc gluconate, Zinc chloride and/or Zinc sulphate. Non-dissolvable additives to DES mixtures include but not limited to: Paraffin, Silica gel, Sodium sulphate or Molecular Sieves™, Polyacrylamide, Aerogel, Polyacrylic acid and/or a Quantum Dot.

It has been found that the addition of ethanol or other alcohols such as methanol and isopropanol to a Choline chloride:Trifluoroacetamide (1:2 mol:mol) has a strong negative influence on the stability of RNA (see Table 2). It is not understood why ethanol in particular has such a negative impact on RNA stability but a change in the Trifluoroacetamide hydrogen bonding with Choline chloride may be a partial explanation. In any case it is preferable to avoid using ethanol at a molar ratio greater than 0.1 compared with Component 1 (Choline chloride). However, if it is desired to process or store tissue samples that have been treated with the DES mixture in ethanol or another alcohol, the excess DES mixture can be removed from the tissue sample using an absorbent paper, washed two times in 100% ethanol before leaving the tissue for longer periods, this abrogates the negative effect on RNA stabilisation. Alternatively the same method can be used to replace the first DES mixture with a second DES mixture, for example, a Choline chloride:Trifluoroacetamide (1:2 mol:mol) mixture can be replaced with a Choline chloride:Urea (1:2 mol:mol) or another DES mixture which may be preferable for certain applications involving RNA stabilisation. Alternatively the biological sample, once removed from the DES mixture can be placed in a desiccating environment such as in a hermetic container containing Molecular sieves, Drierite, a dry sugar (e.g. trehalose, xylitol or sorbitol), RNAstable® (Biomatrica, USA) or Calcium chloride for storage purposes. Yet another alternative is to place the treated biological sample in a liquid storage medium such as alcohol (e.g. methanol, ethanol, propanol or butanol), RNALater (Life Technologies, USA), AllProtect (Qiagen, Germany), PAXgene tissue, PAXgene Blood, (PreAnalytix, Germany), GenTegra RNA (Integenx, USA), Cell-Free RNA BCT® (Streck, USA) or CellSave Preservative (Veridex, USA). As another alternative the sample, following treatment with the DES mixture can be transferred to a solution of a cross-linking fixative such as ten volumes of a 4% solution of formaldehyde or glutaldehyde and allowed to incubate for an appropriate time for example 15 minutes to 24 hours. Although treating the sample with a cross-linking agent will have a negative effect on the quality of RNA, DNA and proteins, the treatment may improve the rigidity of the sample for slide preparation and its performance in certain assays such as immunohistochemistry employing antibodies specific for formalin treated protein epitopes. Another alternative is to pre-treat the sample with ten volumes of a 4% solution of formaldehyde or glutaldehyde and allowed to incubate for an appropriate time for example 15 minutes to 24 hours, prior to removing the sample and adding it to ten volumes of a DES mixture such as Choline chloride:Trifluoroacetamide (1:2 mol:mol) for 15 minutes to 24 hours.

Preferably the use or presence of water is avoided in order to reduce the risk of analyte hydrolysis, in particular RNA, DNA and protein hydrolysis. The DES mixture therefore contains 50% or less, more preferably 40% or less, even more preferably 30% or less, even more preferably 20% or less, even more preferably 10% or less, even more preferably 5% or less and most preferably less than 2% water (weight percentage) for applications requiring RNA, DNA or protein stabilisation. For cell structure and morphology, and tissue fixation the DES mixture may contain 50% or less, more preferably 40% or less, more preferably 30% or less, more preferably 20% or less, more preferably 10% or less but most preferably between 10% and 5% water (weight percentage).

For optimum RNA stabilisation it has been found that the addition of a dessicant to the Choline chloride:Trifluoroacetamide (1:2 mol:mol) mixture is preferable. Suitable desiccants include silica gel, polyacrylamide, Sodium sulphate, Drierite™ and Molecular sieves. A preferred dessicant for RNA stabilisation is Molecular sieve Type 4A (powdered or in pellet form such as 4-12 Mesh) used at 5-50% weight:weight with the DES mixture, preferably a Choline chloride:Trifluoroacetamide (1:2 mol:mol) mixture. An additional advantage is that it has been found that Molecular sieves reduce crystallisation occurring in the Choline chloride:Trifluoroacetamide (1:2 mol:mol) mixture.

It will be apparent that there are many types of DES mixture that can be made and the choice of a particular DES for the purpose of preserving RNA in a sample will be determined by one or more of the following preferable features of the DES: (1) compatibility with RNA, preferably it should have a pH between pH 4.5 and 8.5, more preferably between pH 5 and 8, more preferably between pH 5.5 and 7.5 and most preferably between pH 6 and 7 when mixed with the sample, (2) compatibility with the RNA purification reagents and protocol, for example it should not interfere with the binding between the RNA and silica spin column such as RNeasy (RNeasy Mini Kit, Cat. No. 74106, Qiagen, Germany) or alter the partitioning of RNA in phenol containing reagents such as TRIzol (Cat. No. 15596018 Life Technologies, USA), (3) stabilising RNA in the tissue sample sufficiently quickly as to substantially alter the activity of ribonucleases and/or accessibility of RNA to hydrolysis. Alternatively RNA is stabilised in the tissue sufficiently quickly that the RNA Integrity Number (RIN) is not reduced by more than 2 RIN units, more preferably not more than 1 RIN units, even more preferably not more than 0.5 RIN units and most preferably less than 0.1 RIN units during the initial 18-24 hours storage with the DES mixture at room temperature compared with RNA extracted from a fresh tissue sample, without storage, of the same type, (4) have a capacity to stabilise RNA when the tissue represents at least 10%, more preferably 20% and even more preferably at least 50% of the weight of the DES mixture (weight: weight), (5) not reduce RNA yield by more than 20% compared with fresh tissue, (6) provide stabilisation of DNA, proteins and the phosphate groups of phospho-proteins, (7) be chemically stable, non-flammable, non-toxic to the user and the environment, biodegradable, not react with bleach or reagents used during RNA purification to form toxic compounds, (8) have a shelf-life of at least 6 months at room temperature, (9) fix and stabilise native cell morphology and histology including antibody epitopes and sub-cellular organisation and organelles, whilst stabilising RNA and other biomolecules, (10) fix and stabilise cells in such a way as to subsequently allow histological and immunohistochemistry applications for example with antibodies and stains such as Hoechst or H&E stain, (11) stabilise RNA in FFPE samples to protect and enhance the reversal of formalin cross linking at temperatures greater than 50° C. and to allow the melting and therefore the easy removal of paraffin from the fixed sample, (12) fix and stabilise circulating tumour cells in whole blood to allow their purification, detection and molecular analysis.

The stabilisation of the RNA in the sample can be a result of DES treatment, or a combination of DES treatment with another physical process such as inactivation of ribonucleases, precipitation of cellular proteins and nucleic acid as a result of displacement of water molecules or entry of the dissolved DES into the cell structure of the tissue and leading to RNA stabilisation or a combination of these. The modification or alteration of hydrogen bonding in and around the cell and RNA, by DES's may be an important factor for the observed biomolecule and cell stabilisation as set out in this invention, however the exact mechanism by which DES mixtures can stabilise is not yet known.

The sample or tissue containing the analyte can be a (i) liquid such as blood, plasma, serum, cerebral spinal fluid (CSF), sputum, semen, bronchoalveolar lavage (BAL), amniotic fluid, milk and urine, (ii) solid such as body tissues (liver, spleen, brain, muscle, heart, oesophagus, testis, ovaries, thymus, kidneys, skin, intestine, pancreas, adrenal glands, lungs, bone and bone marrow), (iii) clinical for a medical test such as a prostate, breast or a cancer sample, tumour or biopsy, including a FFPE sample, circulating tumour cells, blood test, clinical swabs, dried blood, exosome, microvesicles, (iv) animal tissues derived from biomedical research or fundamental biology (monkey, rat, mouse, Zebra fish, *Xenopus, Drosophila*, nematode, yeast) and from their various stages of development (egg, embryo, larvae, adult), (v) tissue and tissue culture cells used for drug discovery purposes, (vi) pathogenic and non-pathogenic microbes such as fungi, archaebacteria, gram-positive and gram-negative bacteria, including *E. coli, Staphylococcus, Streptococcus, Mycobacterium, Pseudomonas* and bacteria that cause *Shigella, Diphtheria, Tetanus, Syphilis, Chlamydia, Legionella, Listeria* and leprosy, (vii) pathogenic or non-pathogenic viroids, bacteriophage or viruses that are found in a variety of biological samples such as bacteria, plants, blood, human tissues, animals blood, serum, plasma and tissues, and clinical samples, (viii) plants such as the leaves, flowers, pollen, seeds, stems and roots of rice, maize, sorghum, palm, vines, tomato, wheat, barley, tobacco, sugar cane and *Arabidopsis*, (ix) fixed tissue such as FFPE tissues and biopsies which frequently require specialised protocols for extracting high quality nucleic acids, (x) potentially pathogenic material associated with bioterrorism threats such as anthrax that may or may not need to be transported from the discovery site to the testing facility, (xi) extremely small samples such as those derived from Laser Capture Microdissection samples (LCM), (xii) food samples that may for example contain food borne diseases, (xiii) soil sample. It should be noted that the sample may not be derived solely from biologically derived samples but also chemically or enzymatically synthesised ones such as nucleic acid based copied molecules or amplification products such as in vitro transcribed RNA and PCR products, oligodeoxyribonucleotides and oligoribonucleotides, PNA and LNA. There is no particular limitation to the type of sample that can be used with this invention.

The invention is also useful for the stabilisation of RNA, DNA and protein internal controls (IC) and standards such as those included in HIV or HCV diagnostic kits such as Amplicor™ (Roche Molecular Diagnostics) or for carrier RNA that can be included in such diagnostic kits. For this use, the RNA IC is commonly transported and stored with the rest of the kit components, often at room temperature or 4° C. which may lead to degradation. Stabilisation of the RNA IC or carrier RNA improves kit performance and maintains its integrity during transport and storage.

Usefully the invention can be used to preserve single and/or double stranded RNA viruses including animal RNA viruses such as Norwalk, Rotavirus, Poliovirus, Ebola virus, Marburg virus, Lassa virus, Hantavirus, Rabies, Influenza, Yellow fever virus, Corona Virus, SARS, West Nile virus, Hepatitis A, C (HCV) and E virus, Dengue fever virus, toga (e.g. Rubella), Rhabdo (e.g. Rabies and VSV), Picorna (Polio and Rhinovirus), Myxo (e.g. influenza), retro (e.g. HIV, HTLV), bunya, corona and reoviruses which have profound effects on human health including viroid like viruses such as hepatitis D virus and plant RNA viruses and viroids such as Tobus-, Luteo-, Tobamo-, Potex-, Tobra-, Como-, Nepo-, Almo-, Cucumo-, Bromo-, Ilar-viruses, Coconut cadang-cadang viroid and potato spindle tuber viroid which all have profound effects on agricultural production are all liable to be degraded before, during or after extraction for diagnostic detection purposes. The invention can also be used for stabilising single stranded RNA bacteriophage such as the genus Levivirus including the Enterobacteria phage MS2 and the genus Allolevivirus including the Enterobacteria phage Qβ, or double stranded RNA bacteriophage such as Cystovirus including *Pseudomonas* phage Φ6 or other types of phage such as those used as internal RNA controls for diagnostic applications such as those used in Armored RNA® (Ambion). The invention can also be used for stabilising internal control (IC) RNA or DNA sequences for use in diagnostic kits, by mixing a DES with a pure nucleic acid.

The invention can also be used to stabilise samples for the analysis of miRNA, siRNA and other small naturally occurring RNA molecules such as snRNAs, snoRNA, ncRNA, snoRNA, piRNA and rasiRNA. It can also be used for studies, diagnostics and therapies involving synthetic RNA of the RNAi type.

Usefully the invention can be used to preserve viral RNA such as retroviruses e.g. HIV, rotaviruses, HCV, and West Nile Virus in mixtures of guanidine and blood, serum, plasma cells and/or other medically important sample types such as cells and tissues.

It has been found that certain DES mixtures, notably Choline chloride:Trifluoroacetamide (1:2 mol:mol) have a strong anti-microbial activity (Example 34) thereby making the sample safer to work with and transport. Other applications include stabilising and fixing soil and/or other environmental samples that may have been deliberately contaminated with toxins, viruses, bacteria and/or funghi for subsequent transport and laboratory analysis of RNA, DNA and/or proteins.

This invention therefore relates to methods to improve the storage, preservation, archiving and transport, to protect RNA from degradation, to increase their stability and as a consequence, to improve the analytical sensitivity and assay quality.

It will be evident to one skilled in the art that various DES can be tested for their suitability in this invention by adding them to the sample at a ratio of at least 10:1 (wt:wt) as set out in Example 1. Comparisons of the relative RNA stabilisation can be made using a control solution of RNAlater (10:1 (vol:wt) used according to the manufacturer's instructions (Cat. No. 76106, Qiagen, Germany). Following incubation at, for example 37° C. for one day or more, the RNA is extracted according to a standard protocol such as RNeasy (RNeasy Mini Kit, Cat. No. 74106, Qiagen, Germany) and its intactness analysed by gel electrophoresis or by using a RNA 6000 Nano total RNA Kit (Cat. No. 5067-1511, Agilent Technologies, USA) and Bioanalyser 2100 or other suitable method such as RT-qPCR as described. RNA yields can be determined by OD260 nm uv spectrometry and purity by the well-known OD260/230 and OD260/280 ratios. A Nanodrop ND2000 (ThermoScientific Inc., USA) is one example of a suitable spectrometer for such determination. Once suitable DES mixtures have been identified their optimum amount, purity, amount of contaminating water and use can be determined by further such tests.

Generally the most important single factor for optimisation is the relative molar ratios of the individual components in the DES mixture. In the first instance mixing only two components of the DES mixture is the most straightforward means to identify approximately, and by empirical means as described above, components that result in the desired effect, such as RNA stabilisation, yield, purity and suitability for downstream applications such as RT-PCR or hybridisation. However it will also be apparent to one skilled in the art that a blend of more than two components may be desirable to further enhance or add novel properties to the DES mixture. There are obviously a very large number of potential mixtures of components that can lead to a DES mixture, and although it is easiest to start with the preparation of, in the first instance simple stoichiometric molar ratios of the DES components such as, by way of example only, a 2:1, 1:1 or 1:2 molar ratio (mol:mol) of choline chloride and urea. It is thought that the depression in freezing point of two component DES mixtures is dictated, at least in part, by the hydrogen bonding between the available hydrogen bond donor (e.g. choline chloride) and acceptor (e.g. urea). However it should be noted that the preferred components of the DES mixture and their optimal ratio of mixing for a particular application such as RNA preservation or cell fixation is not necessarily related to the extent of the observed freezing point depression. Identifying the optimum DES mixture for an application must therefore be determined empirically and consequently trial and error testing may be involved. It will be apparent that identifying the best blend for a particular purpose of a greater than two component DES mixture may involve significant effort. Therefore, in the first instance and in the interest of rapidly defining suitable molar ratios of components, stoichiometric ratios may be used as described above. Once approximate molar ratios have been identified, further refinement involving fixing the molar amount of one component whilst varying the other two or more can be made. It should be noted that the molarity of the various DES components is variable and depends on the density, molar ratios and molecular weight of the individual components. By way of example, the Choline chloride concentration in a Choline chloride:Urea (1:2) mixture is approximately 5M and the Urea 10M, compared with a Choline chloride concentration of 3.6M and a Trifluoroacetamide of 7.2M in a Choline chloride:Trifluoroacetamide (1:2) mixture.

The intactness of proteins and phospho-proteins can be determined by preparative or analytical 2-D PAGE, mass spectrometry, suitable anti-phospho antibodies and ELISA as described in Proteome Characterization and Proteomics (2003) edited by Timothy D. Veenstra, Richard D. Smith.

Methods to recover the sample from a viscous DES liquid mixture include fixing or attaching it to a retriever such as a wire, a pin, a brush, a baton, a mesh, an insert, trapping it between two permeable membranes, or between two polymer pads containing sufficient DES to allow efficient DES stabilisation and/or fixation or using a shaped plastic holder capable of gripping the sample during treatment. Preferably any carryover of the DES mixture with the tissue sample is readily soluble in the RNA lysis solution such as RLT (RNeasy Mini Kit, Cat. No. 74106, Qiagen, Germany), and either does not effect the RNA yield or increases it, does not lead the sample to precipitate out of solution and if it carries over with the RNA sample it has no effect on, or otherwise enhances sensitive downstream applications such as RT-qPCR. Methods to determine changes in RNA yield and quality are well known and include spectrophotometric methods, RNA 6000 Nano total RNA Kit (Cat. No. 5067-1511, Agilent Technologies, USA) with Agilent Bioanalyser 2100 quantification and/or RT-qPCR.

The results set out in this invention using DES mixtures are particularly surprising as it is well known that nucleases have very broad requirements for activity, for example Ribonuclease A is a robust nuclease which is active at pH 4-10, variable temperatures such as +4 to 60° C., sodium concentrations of 0-3M, guanidine chaotrope concentrations of up to 400 mM and can survive boiling for several minutes (Raines (1998) Chem. Rev. 98:1045-1065). Despite being very difficult to inactivate such enzymes, the treatment with many different DES mixtures can have a profound effect on nuclease activity with a consequent improvement in RNA quality. One explanation is that the DES components hydrogen bond with enzymes such as nucleases and in particular ribonucleases, displacing native water molecules around the enzyme and leading to denaturation and inactivation, and/or the RNA is protected within denatured DES treated ribonucleoprotein complexes such as ribosomes.

It will be apparent to one skilled in the art that testing the efficiency of a particular DES for biomolecule storage can be carried out in a number of ways. Firstly a known amount of DES can be added to a set amount of pre-weighed tissue for example 20 mg frozen-thawed rat liver and incubated together for varying amounts of time for example 5, 10, 20, 40 and 60 hours at 37° C. and after incubation the tissue recovered and the RNA or other biomolecule recovered by purification and analysed for intactness. The RNA quality can be determined for example, by RT-qPCR or Bioanalyser 2100 (Agilent, USA) RIN analysis.

Preferably the DES mixture has a reasonable shelf-life following preparation meaning that its stabilisation activity does not significantly change during storage for at least six months or more at ambient temperature.

Agitation, mixing and temperature of the DES mixture with the tissue sample are all important factors for optimal RNA stabilisation. Gentle agitation of the DES mixture around the tissue sample can help to increase the rate of stabilisation of the sample. Means of mixing or agitating include using the mixing function of the Thermomixer (Eppendorf, Germany), a rotating wheel or platform such as a LabRoller (LabNet, USA). Although the amount of RNA degradation observed using a DES mixture is limited, inevitably some degradation occurs during the time delay between when the sample is removed from its normal environment in the whole animal and when the DES mixture can start to reduce or completely inhibit the ribonuclease activity. With respect to this invention a key step is the time delay between adding the DES mixture to the sample and ribonuclease inactivation, and it will be evident that ribonucleases are more active at temperatures of 25-37° C. than at 4-16° C. Precooling of the DES and container and maintaining this reduced temperature during the critical DES treatment step is preferred although not essential for tissues with average levels of ribonuclease such as rat liver compared with tissues containing higher levels such as the rat pancreas. RNA quality may be improved in tissues that have high ribonuclease activity by using a reduced temperature, such as 4° C., of the DES mixture, container and environment.

The appropriate choice of a DES mixture for preserving RNA in biological samples depends on multiple overlapping physical and chemical properties. Ideally a DES mixture should be capable of: (1) rapidly and efficiently stabilising biomolecules including RNA, DNA, proteins, post-translationally modified proteins such as phospho-proteins, carbohydrates, lipids and metabolites in a biological sample, (2) functioning optimally to stabilise biomolecules such as RNA, when added in a 20:1 (weight:weight) ratio, more preferably 15:1, even more preferably 10:1, even more preferably 8:1, even more preferably 6:1 even more preferably 4:1, even more preferably 3:1, even more preferably 2:1 and most preferably a 1:1 ratio with the biological sample, (3) being a liquid at below 120° C., even more preferably below 100° C., even more preferably below 80° C., even more preferably below 60° C., and most preferably at room temperature, (4) being not so viscous that working with it and/or removing it from a solid sample is particularly difficult and have a viscosity at 25° C. of less than 100000 cP, even more preferably less than 75000 cP, even more preferably less than 50000 cP, even more preferably less than 25000 cP, even more preferably less than 10000 cP, even more preferably less than 5000 cP, even more preferably less than 2500 cP, even more preferably less than 1 000 cP, even more preferably less than 750 cP, even more preferably less than 500 cP, even more preferably less than 250 cP, even more preferably less than 100 cP, even more preferably less than 75 cP, even more preferably less than 50 cP, even more preferably less than 25 cP, even more preferably less than 10 cP and most preferably less than 5 cP (5) compatibility with RNA and RNA purification reagents such as guanidine HCl, guanidine thiocyanate, Lysis buffer RLT (RNeasy Mini Kit, Cat. No. 74106, Qiagen, Germany) silica spin columns, magnetic silica beads such as MagNA Pure® (Roche Applied Science, UK), TRIzol® (Life Technologies, USA), (6) not reducing RNA binding to a silica column such as RNeasy (Qiagen, Germany) by more than 20% and not decrease the OD260/280 nm spectrophotometric ratio by more than 0.2 compared with a standard purification, and (7) being non-toxic and non-flammable to the user even in combination with the RNA purification reagents, (8) biodegradation, and (9) non-volatility.

As one example of the use of the DES for RNA extraction from FFPE samples, it is well known that formalin fixation leads to multiple cross-linking between the RNA and proteins making subsequent RNA extraction problematic and the quality of the RNA low. The standard protocol for removing cross-links from RNA in a FFPE sample is to heat it, for example at 80° C. for 15-60 minutes, however this causes further RNA degradation (RNeasy FFPE Kit, Cat. No. 73504, Qiagen, Germany). By combining DES with the reagents necessary for the reversal of cross-links, the RNA can be protected during the essential heating step leading to a better quality RNA sample. As one example of a suitable DES, Choline chloride:Trifluoroacetamide (1:2) may be used to treat the FFPE sample at 80° C. to remove paraffin and cross-links from the RNA.

As another example of the use of DES in the medical field is for the treatment of whole blood in order to stabilise circulating tumour cells (CTC's). These cells that are derived from the tumour and then enter the blood stream and are increasingly being used for diagnostic, prognostic and therapeutic purposes and also as end-points for numerous clinical trials of chemotherapeutic drugs. However, stabilising these cells in whole blood is problematic so that shipping of patient blood may lead to loss or difficulty in correctly identifying CTC's and/or carrying out molecular diagnostic analyses. Using a DES mixture to stabilise the CTC's in whole blood in vitro overcomes many of these drawbacks to the current technology of CTC preservation. By way of example only, CTC's in whole blood may be treated with at least six volumes of Choline chloride:Trifluoroacetamide (1:2 mol:mol) in order to fix the cells and preserve the RNA. The CTC's can then be subsequently collected and purified using any one of a number of different methods such as CellSieve™ (MD, USA).

The invention will be described in further detail, by way of example only, with reference to the following Examples and Drawings.

BRIEF DESCRIPTION OF SEVERAL VIEWS OF THE DRAWINGS

FIG. 1 shows apparatus according to the invention in which a DES mixture is disposed in capped vials;

FIG. 2 shows the results of agarose gel electrophoresis on RNA samples extracted according to the invention and the prior art;

FIG. 3 shows the results of agarose gel electrophoresis on RNA stabilised in a DES according to the invention at a range of temperatures;

FIG. 4 shows the results of agarose gel electrophoresis on RNA preserved in tissue according to the invention or the prior art;

FIGS. 5A and 5B show the results of agarose electrophoresis on RNA stabilised in mouse tissue samples using a DES according to the invention and the prior art;

FIG. 6 shows the results of agarose gel electrophoresis on RNA preserved in varying amounts of tissue according to the invention and the prior art;

FIG. 7 shows the results of agarose gel electrophoresis on RNA purified from DES-stabilised whole blood spiked with HeLa cells;

FIG. 8 shows the results of agarose gel electrophoresis on RNA stabilised in whole blood spiked with HeLa cells for 18 hours prior to extraction;

FIG. 9 shows the stabilization of RNA in whole blood with either guanidine or choline chloride:trifluroacetamide;

FIG. 10 shows light microscope images of HeLa cells fixed with choline chloride: trifluoroacetamide according to the invention;

FIG. 11 shows the results of agarose gel electrophoresis on RNA degraded in tissue samples in the absence of any stabiliser;

FIG. 12 shows the results of agarose gel electrophoresis on genomic DNA stabilised in HeLa cells according to the invention or the prior art;

FIG. 13 shows the results of SDS-polyacrylamide gel electrophoresis on protein from mouse liver stabilised according to the invention or prior art;

FIG. 14 shows the results of agarose gel electrophoresis on DNA and RNA from stabilised HeLa cells and optionally subjected to a processing step before purification;

FIG. 15 shows the results of agarose gel electrophoresis on RNA and DNA whose integrity are measured after fixation according to the invention or prior art;

FIG. 16 shows the results of agarose gel electrophoresis on RNA from *Drosophila melanogaster* embryos treated in accordance with the invention or the prior art; and FIG. 17 shows the results of agarose gel electrophoresis on RNA from *Allium cepa* leaf shoots stabilised according to the invention or the prior art.

EXAMPLES

1. RNA Stabilisation in Animal Tissue Samples

To 400 µl of Choline chloride:Urea (1:2 mol:mol) in a standard 1.5 ml polypropylene microcentrifuge tube was added 2-25 mg rat liver sample and pre-incubated for 20 minutes at room temperature to allow stabilisation and/or fixation, the sample can then be incubated in the DES mixture at −80, −20, 4, 20 or 37, 42 or 55° C. for one hour to several weeks prior to recovery of the tissue sample with forceps followed by RNA purification as set out below.

The rate of fixation for some dense, air filled and/or problematic tissues can be improved using a vacuum system such as a Nalgene hand held vacuum pump (Cat. No. 6132-0020, ThermoScientific, UK) during fixation.

The sample is then added to a fresh tube containing 350 µl of Lysis buffer RLT, the tissue homogenised according to manufacturer's instructions (RNeasy Mini Kit, Cat. No. 74106, Qiagen, Germany). 300 µl portions of the lysate were then purified immediately according to manufacturer's instructions and eluted into 20-50 µl of water. The yield and purity of the RNA was then compared by OD 260/280 nm and the integrity of the RNA determined by RT-qPCR using oligo dT cDNA priming and β-actin PCR primers (Quanti-Tect SYBR Green PCR Kit, Cat. No. 204141, Qiagen, Germany) and a LightCycler (Roche Applied Science, France) or by obtaining the RNA Integrity Number (RIN) by using an RNA 6000 Nano total RNA Kit (Cat. No. 5067-1511, Agilent Technologies, USA) and a Bioanalyser 2100 instrument (Cat. No. G2939AA, Agilent Technologies, USA).

Other types of commercialised RNA purification kits can replace the RNeasy kit and there is no particular limitation to the type of kit used.

The liver sample can be replaced with other tissue and cell types such as liver, spleen, brain, muscle, heart, oesophagus, testis, ovaries, thymus, kidneys, skin, intestine, pancreas, adrenal glands, lungs, bone marrow or cells such as COS-7, NIH/3T3, HeLa, 293, and CHO cells or even liquid samples such as serum, plasma or blood.

FIG. 2. A 1% agarose-EtBr gel electrophoresis image of 300 ng RNA samples extracted using an RNeasy kit: Lanes 1-5; Choline chloride:Urea (1:2 mol:mol) stabilised or lanes 6-10 RNAlater (Cat. No. 76106, Qiagen, Germany) stabilised 15 mg rat liver stored for 5 minutes (lanes 1+6), 1 day (lanes 2+7), 3 days (lanes 3+8), 7 days (lanes 4+9) or 21 days (lanes 5+10). It can be observed that after storage at 37° C. that there is improved RNA stability with Choline chloride:Urea stabilised samples compared with RNAlater, by way of comparison after 7 days, the RNA Integrity Number for Choline chloride:Urea sample was RIN=8, whilst that for RNAlater stabilised samples the RIN=5.10.

2. RNA Stabilisation in Animal Tissue Samples Using Other Choline Chloride Based DES Mixtures To 400 µl of Choline chloride:Trifluoroacetamide (1:2 mol:mol) or Choline chloride:Sorbitol (1:1 mol:mol) in a standard 1.5 ml polypropylene microcentrifuge tube was added 2-25 mg rat liver sample and pre-incubated for 20 minutes at room temperature to allow stabilisation and/or fixation, the sample can then be incubated at −80, −20, 4, 20 or 37, 42 or 55° C. for one hour to several weeks prior to recovery of the tissue sample with forceps followed by RNA purification as set out in the following example.

The sample is then added to a fresh tube containing 350 µl of Lysis buffer RLT, the tissue homogenised according to manufacturer's instructions (RNeasy Mini Kit, Cat. No. 74106, Qiagen, Germany). 300 µl portions of the lysate were then purified immediately according to manufacturer's instructions and eluted into 20-50 µl of water. RNA yield and quality was determined as set out in Example 1 and Table 1 and for both DES mixtures RNA integrity was superior compared with RNAlater.

An appropriate source of Choline chloride is Cat. No. 110295000, Acros Organics, France, Sorbitol is Cat. No. S0065, TCI, Belgium and Trifluoroacetamide is Cat. No. T0598, TCI, Belgium.

3. RNA Stabilisation in Animal Tissue Samples Using Other DES Mixtures

To 400 µl of the following DES mixtures in a 2 ml polypropylene tube was added 5-15 mg of rat tissue (frozen tissue stock), following a 20 minute fixation step the sample was incubated at 37° C. for 18 hours prior to RNA extraction/purification using a RNeasy Micro kit (Cat. No. 74004, Qiagen, Germany). Whether the DES mixture was a solid or liquid at room temperature, the RNA yield following extraction and the RNA quality on a scale of 1-10 (with 0 indicating no stabilisation and 10 indicating no degradation, compared with the RNA quality of immediately extracted RNA from a fresh rat liver tissue sample=10). Results are shown in Table 1 below (nd=not determined, 'Saturated' solution is not a DES).

TABLE 1

RNA stabilisation in animal tissue using a two-component DES Mixtures.

|   | Component 1 | Component 2 | Ratio mol:mol | Liquid at 24° C. | RNA Yield ng/μl | RNA Quality 0-10 |
|---|---|---|---|---|---|---|
| 1 | Choline chloride | Urea | 2:1 | No | 120 | 8 |
| 2 | Choline chloride | Urea | 1:1 | No | 185 | 7 |
| 3 | Choline chloride | Urea | 1:2 | Yes | 221 | 7 |
| 4 | Choline chloride | Water | 6M | Saturated | 42 | 3 |
| 5 | Water | Urea | 5M | Saturated | 0 | 0 |
| 6 | Choline chloride | Glycerol | 1:2 | Yes | 62 | 4 |
| 7 | Choline chloride | Ethylene glycol | 1:2 | Yes | 26 | 3 |
| 8 | Choline chloride | Hexanediol | 1:2 | No | 94 | 8 |
| 9 | Acetylcholine chloride | Urea | 1:2 | Yes | 156 | 9 |
| 10 | Acetylcholine chloride | Trifluoroacetamide | 1:2 | Yes | 76 | 5 |
| 11 | Choline chloride | Malonic acid | 1:1 | Yes | 152 | 1 |
| 12 | (2-Chloroethyl) trimethylammonium chloride | Urea | 1:2 | No | 172 | 5 |
| 13 | Choline chloride | Trehalose | 1:1 | No | 285 | 7 |
| 14 | Choline chloride | Xylitol | 1:1 | Yes | 236 | 9 |
| 15 | Choline chloride | Sorbitol | 1:1 | Yes | 395 | 9 |
| 16 | Choline chloride | Guanidine isothiocyanate | 1:2 | No | 75 | 7 |
| 17 | Urea | Guanidine isothiocyanate | 1:2 | No | 10 | 0 |
| 18 | Choline chloride | Phenylacetic acid | 1:1 | Yes | 250 | 3 |
| 19 | Choline chloride | ZnCl2 | 1:2 | No | 173 | 7 |
| 20 | Carnitine | Trifluoroacetamide | 1:2 | Gel | 87 | 5 |
| 21 | Taurine | Trifluoroacetamide | 1:2 | No | 6 | 4 |
| 22 | Tetramethyl ammonium chloride | Urea | 1:2 | No | 80 | 7 |
| 23 | Tetraethyl ammonium chloride | Urea | 1:2 | No | 70 | 7 |
| 24 | Tetrabutyl ammonium bromide | Urea | 1:2 | No | 86 | 5 |
| 25 | Tetrabutyl ammonium iodide | Urea | 1:2 | No | 12 | 1 |
| 26 | Tetramethyl ammonium oxide | Trifluoroacetamide | 1:2 | Yes | 19 | 2 |
| 27 | Choline chloride | Imidazole | 7:3 | No | 82 | 6 |
| 28 | Cetyltrimethylammonium bromide | Urea | 1:2 | No | 65 | 4 |
| 29 | Cetyltrimethylammonium chloride | Trifluoroacetamide | 1:2 | Yes | 15 | 6 |
| 30 | CaCl2 | Urea | 1:3.5 | No | 116 | 2 |
| 31 | ZrCl4 | Urea | 1:3.5 | No | 154 | 8 |
| 32 | TbCl3 | Urea | 1:3.5 | No | 0 | 0 |
| 33 | ZnCl2 | Urea | 1:3.5 | Yes | 162 | 5 |
| 34 | ZnCl2 | Trifluoroacetamide | 1:3.5 | No | 15 | 6 |
| 35 | Choline chloride | N-methylpyrrolidone | 1:2 | Yes | 86 | 6 |
| 36 | Choline chloride | Acetamide | 1:2 | No | 139 | 6 |
| 37 | Choline chloride | Thiourea | 1:2 | No | 229 | 7 |
| 38 | Butyrylcholine iodide | Urea | 1:2 | No | 240 | 7 |
| 39 | Acetylthiocholine chloride | Urea | 1:2 | No | 165 | 6 |
| 40 | Choline bromide | Urea | 1:2 | No | 122 | 7 |
| 41 | Choline bromide | Trifluoroacetamide | 1:2 | Yes | 129 | 7 |
| 42 | Choline chloride | Acrylamide monomer | 1:2 | Gel | 164 | 7 |
| 43 | Choline chloride | 2-Chloroacetamide | 1:2 | Yes | 196 | 5 |
| 44 | Choline chloride | Bistrifluoroacetamide | 1:2 | Yes | 2 | 0 |
| 45 | Choline chloride | 2,2-Difluoropropanamide | 1:2 | Yes | 191 | 6 |
| 46 | Choline chloride | 2,2,2-Trifluorothioacetamide | 1:2 | Yes | 1183 | 7 |
| 47 | Choline chloride | 2-(Trifluoromethyl) phenylacetamide | 1:2 | No | 94 | 4 |
| 48 | Choline chloride | 2,2-Difluoro-2-phenylacetamide | 1:1 | No | 338 | 7 |
| 49 | Choline chloride | 2,2,2-Trifluoro-N-phenylacetamide | 1:2 | No | 91 | 1 |
| 50 | Choline chloride | 3,3,3-Trifluoropropanamide | 1:2 | No | 404 | 8 |
| 51 | Choline chloride | Formamide | 1:2 | Yes | 81 | 5 |
| 52 | Choline chloride | Beta-Mercaptoethanol | 1:2 | Yes | 395 | 7 |
| 53 | Choline chloride | Dithiothreitol | 1:2 | Yes | 202 | 7 |
| 54 | Choline chloride | Dithioerythreitol | 1:2 | Yes | 109 | 2 |
| 55 | Choline chloride | Tiopronin | 1:2 | Yes | 287 | 1 |
| 56 | Choline iodide | Urea | 1:2 | No | 89 | 4 |
| 57 | Choline dihydrogen citrate | Urea | 1:2 | Yes | 67 | 3 |
| 58 | Choline bitartrate | Urea | 1:2 | No | 58 | 4 |
| 59 | Bromocholine bromide | Urea | 1:2 | No | 134 | 6 |
| 60 | Choline chloride | 1,3-dimethylurea | 1:2 | No | 127 | 6 |
| 61 | Choline chloride | Carbohydrazide | 1:2 | No | 129 | 2 |
| 62 | Choline chloride | 1,3-bis(hydroxymethyl)urea | 1:2 | No | 0 | 0 |
| 63 | Choline chloride | N-Methyltrifluoroacetamide | 1:2 | No | 40 | 7 |
| 64 | Choline chloride | Dimethyltrifluoroacetamide | 1:2 | Yes | 22 | 4 |
| 65 | Choline chloride | Diethyltrifluoroacetamide | 1:2 | Yes | 67 | 3 |
| 66 | Choline chloride | (1-trifluoro) acetylimidazole | 1:2 | Yes | 22 | 1 |

TABLE 1-continued

RNA stabilisation in animal tissue using a two-component DES Mixtures.

| | Component 1 | Component 2 | Ratio mol:mol | Liquid at 24° C. | RNA Yield ng/μl | RNA Quality 0-10 |
|---|---|---|---|---|---|---|
| 67 | Choline chloride | Ethyl trifluoroacetate | 1:2 | Yes | 43 | 0 |
| 68 | Choline chloride | Pentafluoropropionamide | 1:2 | No | 62 | 4 |
| 69 | Choline chloride | Heptafluorobutyramide | 1:2 | No | 10 | 4 |
| 70 | Choline chloride | N-Methylbis(Trifluoroacetamide) | 1:2 | No | 14 | 1 |
| 71 | Choline chloride | Lactamide | 1:2 | Yes | 20 | 7 |
| 72 | Choline chloride | 2-Bromoacetamide | 1:2 | No | 23 | 4 |
| 73 | Beta-methylcholine chloride | Trifluoroacetamide | 1:2 | Yes | 19 | 7 |
| 74 | Betaine | Urea | 2:1 | No | 171 | 3 |
| 75 | Betaine | Urea | 1:1 | Yes | 175 | 6 |
| 76 | Betaine | Urea | 1:1.75 | Yes | 208 | 6 |
| 77 | Betaine | Urea | 1:1.95 | Yes | 30 | 7 |
| 78 | Betaine | Urea | 1:2 | Yes | 229 | 7 |
| 79 | Betaine | Urea | 1:2.14 | Yes | 169 | 7 |
| 80 | Betaine | Urea | 1:2.34 | Yes | 100 | 6 |
| 81 | Betaine | Urea | 1:3 | No | 86 | 4 |
| 82 | Betaine | Urea | 1:4 | No | 63 | 3 |
| 83 | Betaine | ZnCl2 | 2:1 | No | 52 | 4 |
| 84 | Betaine | Water | Sat'd | Yes | 0 | 0 |
| 85 | Betaine | Trifluoroacetamide | 1:2 | Yes | 256 | 8 |
| 86 | Carnitine | Urea | 1:2 | Yes | 217 | 5 |
| 87 | Girards reagent T | Urea | 1:2 | Yes | 72 | 1 |
| 88 | Benzyltrimethylammonium chloride | Urea | 1:2 | No | 136 | 8 |
| 89 | Benzyltrimethylammonium chloride | Trifluoroacetamide | 1:2 | Yes | 35 | 6 |
| 90 | Methyltriphenylphosphonium bromide | Ethylene glycol | 1:3 | Yes | 106 | 5 |
| 91 | Methyltriphenylphosphonium bromide | Trifluoroacetamide | 1:2 | Yes | 207 | 4 |
| 92 | Choline chloride | Trifluoroacetamide | 1:2 | Yes | 74 | 9 |
| 93 | Choline chloride | Trichloroacetamide | 1:2 | No | 29 | 3 |
| 94 | Urea | Guanidine isothiocyanate | 1:2 | No | 10 | 0 |
| 95 | Formaldehyde (4%) | — | — | — | 4 | 0 |

Qualitative RNA quality scale as follows; 0 (highly degraded) to 10 (highest quality). The RNA analysis in Table 1 and 2 was carried out as follows; ethidium bromide stained, 1% agarose 0.5×TAE gel electrophoresis followed by visual analysis of a photograph taken under uv light, of the integrity of the 18S and 28S rRNA bands. An RNA sample with an RNA Quality score of 8 or more has an 18S to 28S rRNA ethidium bromide staining ratio of 1:2, whilst an RNA sample with an RNA Quality score of 5 has an 18S to 28S rRNA staining ratio of approximately 1:1.

TABLE 2

Two-Component DES Mixtures plus additive

| | Component 1 | Component 2 | Ratio (mol:mol) | Additive (mole ratio) relative to Component 1) | RNA Yield (ng/μl) | RNA Quality |
|---|---|---|---|---|---|---|
| 1 | Choline chloride | Urea | 1:2 | — | 168 | 8 |
| 2 | Choline chloride | Urea | 1:2 | Ammonium p-toluenesulphonic acid (0.8) | 246 | 6 |
| 3 | Choline chloride | Urea | 1:2 | Sodium p-toluenesulphonic acid (0.8) | 60 | 7 |
| 4 | Choline chloride | Urea | 1:2 | Dimethylbenzene sulphonic acid (0.8) | 126 | 7 |
| 5 | Choline chloride | Urea | 1:2 | (NH4)2SO4 (0.015) | 295 | 6 |
| 6 | Choline chloride | Urea | 1:2 | Zinc chloride (0.95) | 0 | 0 |
| 7 | Choline chloride | Urea | 1:2 | Zinc chloride (0.1) | 122 | 8 |
| 8 | Choline chloride | Urea | 1:2 | CTAB (0.125) | 144 | 7 |
| 9 | Choline chloride | Urea | 1:2 | Sodium dodecyl sulphate (0.04) | 18 | 9 |
| 10 | Choline chloride | Urea | 1:2 | Sodium benzoate (0.8) | 19 | 9 |
| 11 | Choline chloride | Urea | 1:2 | Methyl p-toluenesulphonate (0.1) | 64 | 6 |
| 12 | Choline chloride | Urea | 1:2 | Guanidine isothiocyanate (0.8) | 19 | 3 |
| 13 | Choline chloride | Urea | 1:2 | Ammonium thiosulphate (0.07) | 99 | 6 |
| 14 | Choline chloride | Urea | 1:2 | Dodecyldimethyl(3-sulphopropyl)ammonium hydroxide (0.01) | 122 | 5 |
| 15 | Choline chloride | Trifluoroacetamide | 1:2 | Sorbitol (5% wt:wt) | 274 | 6 |
| 16 | Choline chloride | Trifluoroacetamide | 1:2 | Sorbitol (10% wt:wt) | 272 | 5 |
| 17 | Choline chloride | Trifluoroacetamide | 1:2 | Sorbitol (15% wt:wt) | 254 | 4 |
| 18 | Choline chloride | Trifluoroacetamide | 1:2 | Sorbitol (20% wt:wt) | 96 | 3 |
| 19 | Choline chloride | Trifluoroacetamide | 1:2 | Sorbitol (25% wt:wt) | 15 | 2 |
| 20 | Choline chloride | Trifluoroacetamide | 1:2 | Xylitol (5% wt:wt) | 107 | 6 |
| 21 | Choline chloride | Trifluoroacetamide | 1:2 | Dithiothreitol (9% wt:wt) | 150 | 7 |
| 22 | Choline chloride | Trifluoroacetamide | 1:2 | Zinc chloride (1% wt:wt) | 381 | 7 |

TABLE 2-continued

Two-Component DES Mixtures plus additive

| | Component 1 | Component 2 | Ratio (mol:mol) | Additive (mole ratio) relative to Component 1) | RNA Yield (ng/µl) | RNA Quality |
|---|---|---|---|---|---|---|
| 23 | Choline chloride | Trifluoroacetamide | 1:2 | Zinc acetate (1% wt:wt) | 370 | 4 |
| 24 | Choline chloride | Trifluoroacetamide | 1:2 | Zinc sulphate•7H2O (0.02% wt:wt) | 432 | 8 |
| 25 | Choline chloride | Trifluoroacetamide | 1:2 | Zinc sulphate•7H2O (0.07% wt:wt) | 367 | 8 |
| 26 | Choline chloride | Trifluoroacetamide | 1:2 | Zinc sulphate•7H2O (0.14% wt:wt) | 433 | 8 |
| 27 | Choline chloride | Trifluoroacetamide | 1:2 | Zinc sulphate•7H2O (0.7% wt:wt) | 214 | 8 |
| 28 | Choline chloride | Trifluoroacetamide | 1:2 | Zinc sulphate•7H2O (1% wt:wt) | 70 | 8 |
| 29 | Choline chloride | Trifluoroacetamide | 1:2 | Zinc sulphate anhydrous (1% wt:wt) | 135 | 8 |
| 30 | Choline chloride | Trifluoroacetamide | 1:2 | Zinc EDTA (1% wt:wt) | 214 | 7 |
| 31 | Choline chloride | Trifluoroacetamide | 1:2 | Zinc gluconate (1% wt:wt) | 250 | 4 |
| 32 | Choline chloride | Trifluoroacetamide | 1:2 | Silica gel (50% vol:vol) | 340 | 7 |
| 34 | Choline chloride | Trifluoroacetamide | 1:2 | Molecular sieves 4A (50% vol:vol) | 450 | 7 |
| 33 | Choline chloride | Trifluoroacetamide | 1:2 | Sodium polyacrylate (50% vol:vol) | 308 | 6 |
| 34 | Choline chloride | Trifluoroacetamide | 1:2 | Healthguards ® (50% vol:vol) | 454 | 7 |
| 35 | Choline chloride | Trifluoroacetamide | 1:2 | Ethanol (0.1) | 293 | 6 |
| 36 | Choline chloride | Trifluoroacetamide | 1:2 | Ethanol (0.25) | 595 | 4 |
| 37 | Choline chloride | Trifluoroacetamide | 1:2 | Ethanol (0.5) | 655 | 3 |
| 38 | Choline chloride | Trifluoroacetamide | 1:2 | Ethanol (1) | 679 | 1 |
| 39 | Trehalose | Citric acid | 1:1 | Water (1) | 169 | 2 |

Qualitative RNA quality scale as follows; 0 (highly degraded) to 10 (highest quality). The RNA analysis in Table 1 and 2 was carried out as follows; ethidium bromide stained, 1% agarose 0.5×TAE gel electrophoresis followed by visual analysis of a photograph taken under uv light, of the integrity of the 18S and 28S rRNA bands. An RNA sample with an RNA Quality score of 8 or more has an 18S to 28S rRNA ethidium bromide staining ratio of 1:2, whilst an RNA sample with an RNA Quality score of 5 has an 18S to 28S rRNA staining ratio of approximately 1:1.

4. Mixed Compositions of DES with a Supporting Matrix

In order to improve the physical separation of a DES liquid mixture from the stored sample such as a tissue or biopsy, the DES was mixed with various supporting matrices. The matrix material is not particularly limited but it should retain structural strength even when mixed with the DES and should therefore not dissolve or react. Preferentially the supporting matrix can be labelled directly with for example a barcode or a shelf-life expiration date by means of a printer or ink pen.

To 3.2 g of PEG (MW8000), agarose, polyacrylate or 3 MM cellulose fibres (Whatmann, UK) was added 10 ml of Choline chloride:Trifluoroacetamide (1:1 mol:mol) and heated with stirring at 100° C. for 30 minutes to homogenise the mixture which was then poured into a suitable container to cool.

Such composite mixtures have the advantage of being easier to handle than liquid DES mixtures and reducing carryover of the DES to the extraction step for example RNA purification. The composite can be poured, molded, shaped, cut, layered or formed into any number of containers such as 96, 24 or 6-well plates, 1.5 ml microcentrifuge tubes, 5, 15 or 50 ml tubes.

5. Stabilisation of RNA in Whole Tissue at Different Temperatures

To either 400 µl of Choline chloride:Urea (1:2 mol:mol) or RNAlater in a standard 2 ml polypropylene microcentrifuge tube was added 10 mg rat liver sample and pre-incubated for 20 minutes at room temperature to allow stabilisation and/or fixation, the intact sample was then incubated in the DES mixture at −20, 4, 37, 50 or 65° C. for 18 hours prior to recovery of the intact tissue sample and RNA purification as set out in the following example.

The sample was then added to a fresh tube containing 350 µl of Lysis buffer RLT, and the RNA extracted from the guanidine homogenised tissue according to manufacturer's instructions (RNeasy Mini Kit, Cat. No. 74106, Qiagen, Germany). 300 µl portions of the guanidine lysate was then used to immediately purify the RNA according to manufacturer's instructions and eluted into 20-50 µl of water. RNA yield and quality was determined as set out in Example 1, for the DES stabilisation mixture the RNA integrity was superior at all temperatures greater than 37° C. and equal at −20 and 4° C. compared with RNAlater. Results are shown in FIG. 3. Lanes 1, 3, 5, 7, 9 Choline chloride:Urea (1:2), Lanes 2, 4, 6, 8, 10 RNAlater.

It will be evident to one skilled in the art that Choline chloride:Urea can be replaced with other DES mixtures such as Choline chloride:Trifluoroacetamide (1:2 mol:mol).

6. Long Term Stabilisation of RNA in Whole Tissue at 24° C.

To either 400 µl of Choline chloride:Urea (1:2 mol:mol) or RNAlater in a standard 2 ml polypropylene microcentrifuge tube was added 10 mg rat liver sample and pre-incubated for 20 minutes at room temperature to allow stabilisation and/or fixation, the intact sample was then incubated in Choline chloride:Urea (1:2 mol:mol) at 24° C. for 0-19 days prior to recovery of the intact tissue sample and RNA purification as set out in the following example.

The sample was added to a fresh tube containing 350 µl of Lysis buffer RLT, and the RNA extracted from the guanidine homogenised tissue according to manufacturer's instructions (RNeasy Mini Kit, Cat. No. 74106, Qiagen, Germany). 300 µl portions of the guanidine lysate was then used to immediately purify the RNA according to manufacturer's instructions and eluted into 20 µl of water. RNA yield and quality was determined as set out in Example 1, for the DES stabilisation mixture the RNA integrity was equal to or superior to RNAlater at all time points. Results are shown in FIG. 4. Lanes 1, 3, 5 Choline chloride:Urea (1:2), Lanes 2, 4, 6 RNAlater treated samples.

7. Purification from Different Tissue Types

To either 400 μl of Choline chloride:Urea (1:2 mol:mol) or RNAlater in a standard 2 ml polypropylene microcentrifuge tube was added 10 mg portions of frozen mouse brain (Lanes 3 and 4) or kidney samples (Lanes 1, 2, 5, 6) and pre-incubated for 20 minutes at room temperature to allow stabilisation and/or fixation, the intact sample was then incubated in Choline chloride:Urea (1:2 mol:mol) at 37° C. for 1-7 days prior to recovery of the intact tissue sample and RNA purification as set out below (FIG. 5A. Lanes 1, 3, 5; Stabilisation with Choline chloride:Urea (1:2), Lanes 2, 4, 6; stabilisation with RNAlater (Qiagen, France) for either 24 hours (Lanes 1-4) or 7 days (Lanes 5 and 6)).

Alternatively, 10 mg portions of previously frozen mouse tissue were added to 400 μl of Choline chloride:Trifluoroacetamide and incubated at 37° C. for 18 hours prior to RNA purification (FIG. 5B. Lanes 1, 3, 5, 7, 9, 11, 13, 15; stabilisation with Choline chloride:Trifluoroacetamide (1:2), Lanes 2, 4, 6, 8, 9, 10, 12, 14, 16; stabilisation with RNAlater (Qiagen, Germany).

The sample was added to a fresh tube containing 350 μl of Lysis buffer RLT, and the RNA extracted from the guanidine homogenised tissue according to manufacturer's instructions (RNeasy Mini Kit, Cat. No. 74106, Qiagen, Germany). 300 μl portions of the guanidine lysate was then used to immediately purify the RNA according to manufacturer's instructions and eluted into 20 μl of water. RNA yield and quality was determined as set out in Example 1, for the DES stabilisation mixture the RNA integrity was equal to or superior to RNAlater.

8. Purification from Different Amounts of Tissue

To either 400 μl of Choline chloride:Urea (1:2 mol:mol) or RNAlater in a standard 2 ml polypropylene microcentrifuge tube was added either 15 mg (Lanes 1 and 2) or 25 mg of rat liver (Lanes 3 and 4) and pre-incubated for 20 minutes at room temperature to allow stabilisation and/or fixation, the intact sample was then incubated in Choline chloride:Urea at 37° C. for 18 hours prior to recovery of the intact tissue sample and RNA purification as set out below.

The sample was added to a fresh tube containing 350 μl of Lysis buffer RLT, and the RNA extracted from the guanidine homogenised tissue according to manufacturer's instructions (RNeasy Mini Kit, Cat. No. 74106, Qiagen, Germany). 300 μl portions of the guanidine lysate was then used to immediately purify the RNA according to manufacturer's instructions and eluted into 20 μl of water.

RNA yield and quality was determined as set out in Example 1, for the DES stabilisation mixture the RNA integrity was equal to or superior to RNAlater at all time points. Results are shown in FIG. 6. Lanes 1 and 3, Choline chloride:Urea (1:2), Lanes 2 and 4, RNAlater treated samples.

It was found that the DES mixture containing Choline chloride:Trifluoroacetamide (1:2 mol:mol) was significantly more effective at stabilising RNA in fresh tissues than Choline chloride:Urea (1:2 mol:mol). However, if the tissue is frozen first at −20° C. or −80° C., Choline chloride:Urea is equally effective as Choline chloride:Trifluoroacetamide. It is not understood why Choline chloride:Urea is less effective at stabilising RNA in fresh tissue but it has been found that the addition of 33 mM $ZnCl2$ or $ZnSO4$ to the Choline chloride:Urea (2:1 mol:mol) significantly reduces the amount of RNA degradation occurring when using fresh tissues.

Usefully, tissues such as liver, kidney and muscle treated for at least one hour with a DES, such as Choline chloride: Trifluoroacetamide (1:2 mol:mol) and then frozen at −80° C. are significantly softer than non-treated tissues allowing the penetration of a biopsy needle. This is particularly useful when the sample should not be completely thawed but only a portion removed for further analysis. It should also be noted that the colour of tissues treated with Choline chloride:Trifluoroacetamide, notably blood does not significantly change or fade, whilst untreated or formol treated samples rapidly lose their colour intensity, with or without freezing and such preservation of colour can be an important advantage for correctly analysing biopsy specimens and cell types in a biopsy specimen.

9. Purification of RNA from DES Stabilised Whole Blood Spiked with HeLa Cells To 400 μl of Choline chloride:Trifluoroacetamide (1:2 mol:mol) was added 50 μl of whole human blood spiked with 50 μl of 150,000 HeLa cells and mixed by gentle pipetting, the sample was left to stabilise for 20 minutes at room temperature prior to RNA extraction. Either 50 μl (Lane 1) or 100 μl (Lane 2) of this stabilised DES—blood/cell mixture was mixed with 300 μl of Lysis buffer RLT (RNeasy Mini Kit, Cat. No. 74106, Qiagen, Germany) to lyse the cells and extract the RNA, purification was carried out as follows.

The guanidine blood lysate was centrifuged for 60 seconds at 14,000 g and the supernatant transferred to a fresh tube containing 300 μl of 70% ethanol, mixed by pipetting and then transferred to a MinElute spin column (RNeasy Micro Kit, Cat. No. 74004, Qiagen, Germany). The MinElute column was washed once with 700 μl of Buffer RW1 then twice with 500 μl of Buffer RPE, centrifuged for 60 seconds to dry the column prior to elution with 20 μl of water according to the manufacturer's instructions. The RNA yield was determined by OD260 nm absorbance using a Nanodrop (ThermoScientific, USA) and loaded and analysed in a 1% agarose, 0.5×TAE gel.

TABLE 3

Yields of RNA derived from HeLa cell spiked blood samples.

| | Sample volume | Total RNA Yield |
|---|---|---|
| 1 | 50 μl | 200 ng |
| 2 | 100 μl | 2400 ng |

Results are shown in FIG. 7. It is notable that the silica MinElute spin column after passage of the guanidine—blood lysate was not visibly contaminated with haem. The Choline chloride:Trifluoroacetamide—guanidine mixture therefore appears to protect the silica membrane from non-specific contamination.

10. Stabilisation of RNA in Whole Blood Spiked with HeLa Cells Using Choline Chloride:Trifluoroacetamide To 1000 μl of Choline chloride:Trifluoroacetamide (1:2 mol:mol) was added 200 μl of whole human blood spiked with 50 µl of 1,000,000 HeLa cells and mixed by gentle pipetting, the sample was incubated for 18 hours at room temperature prior to RNA extraction. Either 100 µl (FIG. 8; Lane 1), 150 µl (Lane 2), 200 µl (Lane 3) or 250 µl (Lane 4) of the stabilised DES—blood/cell mixture was mixed with 250 µl of Lysis buffer RLT (RNeasy Mini Kit, Cat. No. 74106, Qiagen, Germany) in order to lyse the cells and extract the RNA, purification was carried out as follows.

The guanidine blood lysate was centrifuged for 60 seconds at 14,000 g and the supernatant transferred to a fresh tube containing 300 µl of 70% ethanol, mixed by pipetting and then transferred to a MinElute spin column (RNeasy MinElute, Cat. No. 74204, Qiagen, Germany). The MinElute column was washed once with 700 µl of Buffer RW1 then twice with 500 µl of Buffer RPE, centrifuged for 60 seconds to dry the column prior to elution with 20 µl of water according to the manufacturer's instructions. The RNA yield was determined using a Nanodrop (Agilent, USA) and loaded and analysed in a 1% agarose, 0.5×TAE gel. The OD 260/280 nm data demonstrates that the RNA is substantially free of contaminating protein, whilst the RNA yields suggest that the MinElute columns are saturated with RNA and that MinElute columns (RNeasy Mini Kit, Cat. No. 74106, Qiagen, Germany) would provide even better yields.

TABLE 4

RNA yields and quality following storage of blood samples for 18 hours.

| | Sample volume | OD 260/280 nm | Total RNA Yield |
|---|---|---|---|
| 1 | 100 µl | 2.03 | 640 ng |
| 2 | 150 µl | 2.03 | 1500 ng |
| 3 | 200 µl | 2.01 | 1120 ng |
| 4 | 250 µl | 2.09 | 600 ng |

Stabilisation of RNA overnight in whole blood was also demonstrated as follows. 50,000 HeLa cells were mixed with 50 µl of fresh human whole blood and then the cells and blood were added to either 400 µl of Buffer RLT (Qiagen, Germany) or 400 µl of Choline chloride:Trifluoroacetamide (1:2 mol:mol), and incubated overnight at 24° C., RNA was then purified according to manufacturer's instructions (RNeasy Mini, Qiagen, Germany). The RNA was significantly protected in whole blood from degradation by Choline chloride:Trifluoroacetamide (1:2 mol:mol) but degraded when stored overnight in Buffer RLT. Storage of RNA in whole blood, either in a cellular form such as white blood cells or circulating tumour cells, in a sub-cellular form such as exosomes or other microvesicles, or within viral particles can be carried out by adding 1:8 or more preferably, 1:10 of whole blood to Choline chloride:Trifluoroacetamide (1:2 mol:mol). Alternatively 10 mM ZnCl2 or ZnSO4 with or without 20% wt:wt Molecular sieves 4A can be added to the Choline chloride:Trifluoroacetamide to improve RNA stability further.

FIG. 9 shows stabilisation of RNA in whole blood with either Guanidine or Choline chloride:Trifluoroacetamide (1:2 mol:mol). Storage of samples overnight at 24° C. in either Buffer RLT (Qiagen, Germany) (Lane 1) or 400 µl of Choline chloride:Trifluoroacetamide (1:2 mol:mol) (Lane 2), Total RNA becomes significantly degraded in guanidine but not Choline chloride:Trifluoroacetamide.

11. Stabilisation of Whole Blood Using a Vacuum Blood Draw Tube

To a 10 ml polyethylene terephthalate (PET) blood collection tube was added 7 ml of sterile Choline chloride:Trifluoroacetamide (1:2 mol:mol), and the tube closed with a HEMOGARD™ (Becton Dickinson, USA) or other appropriate closure and the air partially removed to create a vacuum. Alternatively, the blood collection tube can contain in addition to the 7 ml of Choline chloride:Trifluoroacetamide (1:2 mol:mol) ZnSO4 to give a final concentration in the diluted blood sample of either 1 mM, 5 mM, 10 mM, 33 mM, 100 mM or 200 mM. As an example of a blood draw tube device see FIG. 1, right. Approximately 2 ml of whole venous blood was drawn into the tube using a blood collection set (PreAnalytix, Germany) or via filling a regular luer-lock syringe and needle, and transferring 2 ml of the contents to the blood-collection tube. Following addition of the blood, the tube was inverted 10 times in order to mix the components and then incubated for 20 minutes at room-temperature to fix and stabilise the RNA in white blood cells such as T- and B-lymphocytes, monocytes, macrophages (e.g. PBMC), neutrophils, basophil and oesonophils (polymorphonuclear cells), thrombocytes and any bacteria or viruses as set out in the description including HPV, HIV, HCV, HBV, Influenza and coronaviruses implicated in SARS. In general erythrocytes do not remain intact in this mixture. Other cell types such as circulating tumour cells can also be stabilised and fixed using this method allowing better capture, analysis and storage of the CTC's.

Following storage in the blood collection tube for up to, for example 24 hours at 37° C., 3 days at room-temperature, 1 week at 4° C. or 3 months at −20° C., the RNA can be extracted from the Choline chloride:Trifluoroacetamide stabilised blood as follows: The blood collection tube was opened and 1 ml of the stabilised sample was removed and mixed with 3 ml of Lysis Buffer RLT, centrifuged for 60 seconds at 14,000 g, the supernatant removed and added to an equal volume of 70% ethanol prior to loading in either a RNeasy MinElute (RNeasy Mini Kit, Cat. No. 74106, Qiagen, Germany) or a RNeasy Midi spin column (RNeasy Midi Kit, Cat. No. 75142, Qiagen, Germany) and then the spin column was washed with Buffers RW1 and RPE and the RNA eluted according to the kit manufacturers instructions.

12. Measuring the Cell Fixation Properties of DES Mixtures

To each well in a 12-well tissue culture plate was added 20,000 freshly trypsinised HeLa cells in 1 ml DMEM/5% FBS and the cells then allowed to attach to the plate surface by incubating in an appropriate tissue culture incubator for at least 6 hours at 37° C. The tissue culture medium was then removed using a vacuum pipette and 400 µl of a DES mixture was added to each well whilst examining any morphological changes of the cells in real-time under a 20× light microscope. The tissue culture plate was then returned to a 37° C. incubator for 90 minutes prior to further microscope examination. Dulbecco's buffered phosphate saline (DPBS) was used a non-toxic control and results shown in the following table. Cell viability was ascertained by standard Trypan Blue staining.

TABLE 5

Effects of Various Fixatives and Additives on Cell Morphology.

| | Fixative (mol:mol) | Effect on cells | Cell viability |
|---|---|---|---|
| 1 | Dulbecco phosphate buffered saline | Unchanged | Yes |
| 2 | Choline chloride:urea (1:2) | Cells contract and cytoplasm translucent | No |
| 3 | Choline chloride:Xylitol (1:1) | Detach, shrink with crenation | No |
| 4 | Choline chloride:Sorbitol (1:1) | Detach, shrink with crenation | No |
| 5 | Choline chloride:Trifluoroacetamide (1:2) | Unchanged | No |
| 6 | Choline chloride:Ethylene glycol (1:2) | Detach | No |
| 7 | Choline chloride:urea:ZnCl2 (1:2:1) | 15% lysis, cells opaque, no shrinkage | No |
| 8 | Choline chloride:urea:ZnCl2 (10:20:1) | Cells opaque and 80% reduced size | No |
| 9 | Choline chloride:urea:CTAB (8:16:1) | Homogenous cytoplasm no shrinkage | No |
| 10 | Choline chloride:urea:SDS (25:50:1) | Reasonable morphology, no cell shrinkage | No |
| 11 | Choline chloride:urea:Methyl p-toluene sulphonate (3:6:1) | Reasonable morphology, opaque, 80% cytoplasmic condensation | No |
| 12 | Choline chloride:urea:Sodium benzoate (36:72:1) | Cytoplasm hypercondensed, opaque | No |
| 13 | Choline chloride:Guanidine isothiocyanate (2:1) | Cells swell and lyse | No |
| 14 | ZnCl2:Ethylene Glycol (1:4) | Cells highly condensed, 50% detached | No |
| 15 | ZnCl2:Ethylene Glycol:Trifluoroacetamide (1:3:1) | Cytoplasm highly condensed, rupture and heterogenous | No |
| 16 | RNAlater | Blebbing of cytoplasm, otherwise intact and opaque | No |

TABLE 6

Effects of Various DES Mixtures with or without additives on Cell Morphology.

| | Component 1 | Component 2 | Ratio (mol:mol) | Additive Final % | Effect on HeLa Morphology |
|---|---|---|---|---|---|
| 1 | Choline chloride | Trifluoroacetamide | 1:1.8 | — | ++++ |
| 2 | Choline chloride | Trifluoroacetamide | 1:2 | — | ++++ |
| 3 | Choline chloride | Trifluoroacetamide | 1:2.25 | — | ++ |
| 4 | Choline chloride | Trifluoroacetamide | 1:2.5 | — | ++++ |
| 5 | Choline chloride | Trifluoroacetamide | 1:2.75 | — | ++++ |
| 6 | Choline chloride | Trifluoroacetamide | 1:3 | — | +++++ |
| 7 | Choline chloride | Trifluoroacetamide | 1:2 | H2O (17%) | +++++ |
| 8 | Choline chloride | Trifluoroacetamide | 1:2 | H2O (13%) | +++ |
| 9 | Choline chloride | Trifluoroacetamide | 1:2 | H2O (10%) | +++ |
| 10 | Choline chloride | Trifluoroacetamide | 1:2 | H2O (5%) | ++++ |
| 11 | Choline chloride | Trifluoroacetamide | 1:2 | H2O (2.5%) | +++ |
| 12 | Choline chloride | Trifluoroacetamide | 1:2 | Ethylene glycol (17%) | ++ |
| 13 | Choline chloride | Trifluoroacetamide | 1:2 | 1,6-Hexanediol (17%) | +++ |
| 14 | Choline chloride | Trifluoroacetamide | 1:2 | Ethanol (17%) | ++++ |
| 15 | Choline chloride | Trifluoroacetamide | 1:2 | Methanol (17%) | +++ |
| 16 | Choline chloride | Trifluoroacetamide | 1:2 | Dimethylformamide (17%) | + |
| 17 | Choline chloride | Trifluoroacetamide | 1:2 | Dimethylsulphoxide (17%) | +++ |
| 18 | Choline chloride | Trifluoroacetamide | 1:2 | N-Methyl pyrrolidone (17%) | +++++ |
| 19 | Choline chloride | Trifluoroacetamide | 1:2 | N-Ethyl pyrrolidone (5%) | +++++ |
| 20 | Choline chloride | Trifluoroacetamide | 1:2 | Ethyleneurea (5%) | ++ |
| 21 | Choline chloride | Trifluoroacetamide | 1:2 | Pivalamide (5%) | +++ |
| 22 | Choline chloride | Trifluoroacetamide | 1:2 | 1,3-Dimethylurea (5%) | ++ |
| 23 | Choline chloride | Trifluoroacetamide | 1:2 | N,N'-Dimethylourea (5%) | ++ |
| 24 | Choline chloride | Trifluoroacetamide | 1:2 | Isopropanol (17%) | ++++ |
| 25 | Choline chloride | Trifluoroacetamide | 1:2 | Butanol (17%) | ++++ |
| 26 | Choline chloride | Trifluoroacetamide | 1:2 | Glycerol (17%) | ++ |
| 27 | Choline chloride | Trifluoroacetamide | 1:2 | 1-Methylimidazole (33%) | +++++ |
| 28 | Choline chloride | Trifluoroacetamide | 1:2 | 1-Methylimidazole (5%) | ++ |
| 29 | Choline chloride | Trifluoroacetamide | 1:2 | 1-Ethylimidazole (5%) | ++ |
| 30 | Choline chloride | Trifluoroacetamide | 1:2 | 1-Benzylimidazole (2.5%) | +++++ |
| 31 | Choline chloride | Trifluoroacetamide | 1:2 | 1-Benzylimidazole (5%) | +++++ |
| 32 | Choline chloride | Trifluoroacetamide | 1:2 | Tetramethylurea (1%) | +++++ |
| 33 | Choline chloride | Trifluoroacetamide | 1:2 | Tetramethylurea (5%) | +++++ |
| 34 | Choline chloride | Trifluoroacetamide | 1:2 | Ethylene carbonate (33%) | ++ |
| 35 | Choline chloride | Trifluoroacetamide | 1:2 | Imidazole 33%) | ++++ |
| 36 | Choline chloride | Trifluoroacetamide | 1:2 | Lithium acetate (33%) | ++ |
| 37 | Choline chloride | Trifluoroacetamide | 1:2 | 4-Formyl morpholine (33%) | +++++ |
| 38 | Choline chloride | Trifluoroacetamide | 1:2 | Acetonyl acetone (20%) | ++ |
| 39 | Choline chloride | Trifluoroacetamide | 1:2 | Guanidine HCl (3.4%) | ++ |
| 40 | Choline chloride | Acrylamide | 1:2 | — | ++ |
| 41 | Choline chloride | 2-Chloroacetamide | 1:2 | — | ++ |
| 42 | Choline chloride | Bistrifluoroacetamide | 1:2 | — | ++++ |
| 43 | Choline chloride | 2,2-Difluoropropanamide | 1:2 | — | +++ |
| 44 | Choline chloride | 2,2,2-Trifluorothioacetamide | 1:2 | — | ++ |
| 45 | Choline chloride | Formamide | 1:2 | — | ++ |
| 46 | Choline chloride | Methanol | 1:2 | — | ++ |

TABLE 6-continued

Effects of Various DES Mixtures with or without additives on Cell Morphology.

| | Component 1 | Component 2 | Ratio (mol:mol) | Additive Final % | Effect on HeLa Morphology |
|---|---|---|---|---|---|
| 47 | Choline chloride | Ethanol | 1:2 | — | ++ |
| 48 | Choline chloride | Trifluoroacetamide | 1:2 | Sorbitol (5%) | ++ |
| 49 | Choline chloride | Trifluoroacetamide | 1:2 | Xylitol (5%) | ++ |
| 50 | Choline chloride | Urea | 1:2 | — | ++ |
| 51 | Choline chloride | Urea | 1:2 | Na cacodylate (10%) | +++ |
| 52 | Choline chloride | Urea | 1:2 | SDS (5%) | ++ |
| 53 | Choline chloride | Urea | 1:2 | Na p-Toluene sulphonic acid (6%) | + |
| 54 | Choline chloride | Urea | 1:2 | Triton TX-45 (12%) | + |
| 55 | Choline chloride | Urea | 1:2 | Na benzoate (8%) | +++ |
| 56 | Choline chloride | Urea | 1:2 | Guanidine isothiocyanate (7%) | + |
| 57 | Choline chloride | Urea | 1:2 | Sulpho salicylic acid (10%) | + |
| 58 | Choline chloride | Urea | 1:2 | CTAB (8%) | ++ |
| 59 | Choline chloride | Urea | 1:2 | Zinc chloride (11%) | +++ |
| 60 | Choline chloride | Urea | 1:2 | Methyl p-toluenesulphonate (25%) | ++ |
| 61 | ZnCl2 | Ethylene glycol | 1:4 | — | + |
| 62 | ZnCl2 | Ethylene glycol:Trifluoroacetamide | 1:3:1 | — | + |
| 63 | ZnCl2 | Urea | 1:3.5 | — | + |
| 64 | ZnCl2 | Trifluoroacetamide | 1:3.5 | — | ++ |
| 65 | Choline chloride | Sorbitol | 1:1 | — | ++++ |
| 66 | Choline chloride | Guanidine isothiocyanate | 2:1 | — | + |
| 67 | Choline chloride | Phenylacetic acid | 1:2 | — | + |
| 68 | Choline chloride | Malonic acid | 1:2 | — | + |
| 69 | Choline chloride | Boric acid | 1:1.5 | — | +++ |
| 70 | Acetylcholine chloride | Urea | 1:2 | — | + |
| 71 | Acetylcholine chloride | Trifluoroacetamide | 1:2 | — | ++ |
| 72 | Choline bromide | Urea | 1:2 | — | + |
| 73 | Choline bromide | Trifluoroacetamide | 1:2 | — | ++++ |
| 74 | Beta-methylcholine chloride | Trifluoroacetamide | 1:2 | — | + |
| 75 | Carnitine | Trifluoroacetamide | 1:2 | — | ++ |
| 76 | Taurine | Trifluoroacetamide | 1:2 | — | + |
| 77 | Methyltriphenylphosphonium bromide | Trifluoroacetamide | 1:3 | — | + |
| 78 | Grignard Reagent T | Trifluoroacetamide | 1:2 | — | +++ |
| 79 | Chloroethyltrimethyl ammonium chloride | Trifluoroacetamide | 1:2 | — | +++ |
| 80 | Cetyltrimethylammonium chloride | Trifluoroacetamide | 1:2 | — | ++ |
| 81 | Tetramethyl ammonium oxide | Trifluoroacetamide | 1:2 | — | + |
| 82 | Choline chloride | Trichloroacetamide | 1:2 | — | ++ |
| 83 | Benzyltrimethylammonium chloride | Trifluoroacetamide | 1:2 | — | +++ |
| 84 | Betaine | Trifluoroacetamide | 1:2 | — | +++ |

Effect on HeLa cell morphology, scale + (worst) to +++++ (best).

13. Cell Fixation with Trifluoroacetamide Containing DES Mixtures

HeLa tissue culture cells were grown under standard tissue culture conditions in a 24 well tissue culture plate to confluence, the 1 ml of DMEM/FBS medium was removed and replaced with 0.2-1.0 ml of (A) Dulbecco's phosphate buffered saline (DPBS) or (B) Choline chloride:Trifluoroacetamide (1:2 mol:mol) and the cells imaged under a 50× standard light microscope. Representative fields of cells are shown in FIG. 10, no substantial changes to the cell morphology were seen between the DPBS or Choline chloride:Trifluoroacetamide treated cells. As one test to demonstrate that the DES treated cells were fixed, the DPBS or Choline chloride:Trifluoroacetamide was removed and the cells washed with 2 ml tap water, it was found that, after one hour at room temperature, only the DPBS treated cells swelled and then ruptured from the osmotic effect of the water, whilst the Choline chloride:Trifluoroacetamide treated cells remained largely unchanged by this additional treatment even after 1 month submersion in water at room temperature demonstrating that they had indeed been fixed. Furthermore, as proof of the fixation of the cells, they were treated with 1 mL of 0.05% Trypsin for one hour at room temperature and it was found that, unlike with DPBS treated cells, there was no effect or visible protease degradation of the cells and they remained intact.

The Choline chloride:Trifluoroacetamide (1:2 mol:mol) can be replaced with Choline chloride:Trifluoroacetamide 1:1, 1:1.5, 1:1.75, 1:2.25, 1:2.5, 1:2.75 or 1:3 (mol:mol). Alternatively the Choline chloride:Trifluoroacetamide can be replaced with Betaine:Trifluoroacetamide (1:2 mol:mol) or Acetylcholine chloride:Trifluoroacetamide (1:2 mol:mol). There is no particular limitation to the DES mixture for cell fixation but Trifluoroacetamide containing mixtures are particularly useful for cell fixation and RNA stabilisation (see Table 1).

Tissue culture cells and tissues can be fixed with Choline chloride:Trifluoroacetamide (1:2 mol:mol) at different temperatures without the cells lysing or becoming distorted. 400 µl portions of Choline chloride:Trifluoroacetamide were preheated at 37° C., 100° C. or 120° C., and with a pre-heated pipette tip added to HeLa cells in a 24-well plate. Immediate microscope observation of the cells after the addition of the hot Choline chloride:Trifluoroacetamide showed that, remarkably, they had a morphology very similar to cells fixed at room temperature. The viscosity of hot Choline chloride:Trifluoroacetamide is significantly less than at room temperature.

Specifically, the cell fixation properties of the deep eutectic solvent were determined and quantified as follows: approximately 2,000 HeLa cells were grown on a 25 mm Cellattice™: Micro-Ruled Cell Culture Surface (Micro-ruled cell culture coverslip surface, Cat. No. CLS5-25D-050 Nexcelom Bioscience, USA) placed in a 24-well tissue culture plate and grown overnight in 2 ml of DMEM/10% FBS, the number of attached cells in a defined area of the grid was counted manually using a 10× objective microscope lens, the tissue culture medium was then removed using an aspirating pipette and replaced with 400 mg of a deep eutectic solvent, incubated for 1 hour at room temperature to allow cell fixation and then the deep eutectic solvent removed with an aspirating pipette and replaced with 2 ml of distilled water, incubated for 1 hour at room temperature and the number of cells in the same defined area of the grid as before treatment counted manually. The percentage of attached cells remaining in the grid compared with the original number was calculated and it was found that at least 75% of the cells were attached following treatment with Choline chloride:Trifluoroacetamide (1:2 mol:mol). Note the cells should not be grown to confluence as large numbers of loosely attached dying cells have been found to detach easily and therefore cause errors in cell counting. It will be evident to one skilled in the art that the cell fixation properties of other deep eutectic solvents can also be determined using this method.

14. Solubility of Salt Mixtures in Choline Chloride:Urea

It was notably found that Zinc chloride (ZnCl2) could be dissolved in Choline chloride:Urea (1:2) to give a DES mixture of Choline chloride:Urea:ZnCl2 of 1:2:2 (mol:mol:mol), Guanidine isothiocyanate can be dissolved in Choline chloride:Urea to give a DES mixture of Choline chloride:Urea:Guanidine isothiocyanate of 1:2:5 (mol:mol:mol) and Ammonium acetate could be dissolved in Choline chloride:Urea (1:2) to give a DES mixture of Choline chloride:Urea:Ammonium acetate of 1:2:3 (mol:mol:mol).

15. RNA Degradation in the Absence of a Stabiliser

In order to determine the rate of RNA degradation in the absence of a DES mixture or other stabiliser, 50 mg pieces of rat liver were incubated at 20° C. for (Lane 1) 0 min, (Lane 2) 1 min, (Lane 3) 2 min, (Lane 4) 5 min, or (Lane 5) 20 min prior to RNA purification according to Example 1. Results are shown in FIG. 10.

It was found that the RNA was noticeably degraded after 5 minutes at room temperature and significantly degraded after 20 minutes. This provides a method to estimate the maximum amount of time that RNA in a tissue can remain intact before it starts to degrade and therefore the rapidity and efficacy that the DES fixative can be compared against. For example the weight of samples from a tissue with a relatively low rate of RNA degradation such as muscle can be larger than from a tissue with a higher rate such as pancreas.

16. DNA Stabilisation in Animal Tissue Samples

To 400 µl of Choline chloride:Trifluoroacetamide (1:2 mol:mol) in a standard 1.5 ml polypropylene microcentrifuge tube was added 2-25 mg rat liver sample and pre-incubated for 20 minutes at room temperature to allow stabilisation and/or fixation, the sample can then be incubated at −80, −20, 4, 20 or 37, 42 or 55° C. for one hour to several weeks prior to recovery of the tissue sample with forceps followed by RNA and then DNA purification as set out below.

Briefly, the sample is mechanically lysed in 400 µl of Lysis buffer RLT and the RNA eluted in at least 40 µl of water according to manufacturer's instructions (RNeasy Mini Kit, Cat. No. 74106, Qiagen, Germany), the silica membrane is then washed with 100 µl of water, centrifuged for 60 seconds at 10,000×g and the flow through discarded, then 100 µl of 10 mM NaOH is added, incubated at 70° C. for 15 minutes to destroy residual RNA and then centrifuged for 60 seconds at 10,000×g and the flow through containing the DNA collected and analysed using a 1% agarose gel.

Commercialised DNA purification kits such as the PureLink® (Cat. No. 12183018A, Life Technologies, USA) and DNeasy Mini Kit, (DNeasy Mini Kit, Cat. No. 69504, Qiagen, Germany) can also be used and there is no particular limitation to the type of kit or type of tissue that can be used for DNA purification.

The liver sample can be replaced with other tissue and cell types such as liver, spleen, brain, muscle, heart, oesophagus, testis, ovaries, thymus, kidneys, skin, intestine, pancreas, adrenal glands, lungs, bone marrow or cells such as COS-7, NIH/3T3, HeLa, 293, and CHO cells or even liquid samples such as serum, plasma or blood.

It was found that DNA extracted from rat liver samples that had been fixed and stabilised in 400 µl of Choline chloride:Trifluoroacetamide (1:2) compared with 400 µl of RNAlater at room-temperature had significantly more intact DNA demonstrating the superior stabilisation of DES mixture compared with RNAlater, a product that has been recommended to preserve DNA as well as RNA. 1-33 mM ZnSO4 can also be added to improve DNA stabilisation.

Results are shown in FIG. 12. HeLa cell pellets stabilised in; Choline chloride:Trifluoroacetamide (1:2 mol:mol) (Lane 1 and 3), RNAlater (Lanes 2 and 3), for either 9 (Lanes 1 and 2) or 15 days (Lanes 3 and 4) at 24° C. The DNA in RNAlater stabilised samples is significantly more degraded than with Choline chloride:Trifluoroacetamide.

17. Protein Stabilisation in Animal Tissue Samples

To 400 µl of Choline chloride:Trifluoroacetamide (1:2 mol:mol), 10 mM ZnSO4.7H2O and 40 mg Molecular sieves 4A in a standard 1.5 ml polypropylene microcentrifuge tube was added 10 mg of frozen-thawed mouse liver and incubated for either 4, 7 or 18 days at 24° C. Control mouse liver samples were incubated in 400 µl of PBS for either 0 minutes, 36 hours, 6 days or 13 days at 24° C. prior to protein extraction.

Proteins were extracted by adding 10 volumes of 1× Sample buffer (125 mM Tris-HCl pH 6.8, 2% SDS, 10% glycerol, 5% β-mercaptoethanol, 0.001% bromophenol blue) to the liver sample, grinding with a Pellet pestle for 30 seconds and then immediately heating the sample for 10 minutes at 70° C., placing the tube on ice for 5 minutes and then centrifuging for 5 minutes at 10,000×g prior to protein dosing by the Bradford method (Bio-Rad, France). 30 µg of each protein were mixed with Laemlli buffer and loaded in a standard SDS-7.5% acrylamide gel and electrophoresed for 3 hours at 110V. The proteins were then transferred to a Western blotting PVDF/ECL+ membrane and incubated overnight in TBS (0.1% Tween-20), 5% milk powder at 4° C. with a 1:500 dilution of the primary antibody anti-α-actin, the membrane was washed three times with TBS (0.1% Tween-20, 5% milk powder) and incubated for 60 minutes at 24° C. with a 1:100 dilution of a HRP labelled mouse anti-IgG secondary antibody, washing and development with Supersignal West pico chemiluminescent kit (Pierce, France).

Results are shown in FIG. 13. Mouse liver stabilised in; PBS (Lanes 2-4) or Choline chloride:Trifluoroacetamide (1:2 mol:mol) (Lanes 5-7), for either 0 minutes (Lane 1), 36 hours (Lane 2), 6 days (Lane 3), 13 days (Lane 4), 4 days (Lane 5), 7 days (Lane 6) or 18 days (Lane 7) at 24° C. The IgG and actin proteins in PBS stored samples are significantly more degraded than with Choline chloride:Trifluoroacetamide.

18. Cell Fixation with Choline Chloride:Trifluoroacetamide (1:2 mol:mol) for Immunohistochemistry (IHC)

HeLa cells were grown to 20% cell density on 13 mm glass coverslips in a 24-well tissue culture plate, the DMEM growth media was removed with a vacuum pipette, the edge dabbed dry with a tissue and the coverslip transferred to a 12 well plate and 600 μl of Choline chloride:Trifluoroacetamide (1:2 mol:mol) added directly onto the cover slip and left for 60 minutes on a rocking platform at room temperature to allow fixation. The coverslip and cells were then removed from the fixative, excess fixative removed with a vacuum pipette and dabbing with a paper tissue, and washed for 4×5 minutes with 2 ml of PBS. The cells were blocked with 2 ml of PBS/1% BSA on a rocking platform, then a suitable dilution, such as 1:100, of the primary antibody was added and left over night at 4° C. The cells were then washed in 3×2 ml of PBS/1% BSA for 5 minutes each, and a suitable dilution, such as 1:1000 of Alexafluor 488 goat anti-mouse IgG1 (Life Technologies, UK), of the secondary labelled antibody was added and incubated in the dark for 30 minutes at room temperature. The cells were washed in 3×2 ml of PBS/1% BSA and then 3×2 ml of PBS and then briefly rinsed in water prior to mounting with Vectashield/DAPI (Vector Labs, UK) and observation with a suitable microscope.

Alternatively, the addition of 10 mM ZnSO4, ZnCl2, 5% (vol:vol) N-Ethylpyrrolidone, 5-10% of an aqueous solution such as water, PBS or DMEM, 2.5% (vol:vol) 1-Benzylimidazole or 1% (vol:vol) Tetramethylurea into the Choline chloride:Trifluoroacetamide (1:2 mol:mol) can be made prior to cell fixation to improve the immunohistochemistry results.

19. Mammalian Tissue Fixation with Choline Chloride:Trifluoroacetamide (1:2 mol:mol) for Staining or Immunohistochemistry (IHC)

Freshly dissected mouse tissue pieces such as liver, kidney, lung, brain, smooth, skeletal or cardiac muscle, spleen, thymus, salivary gland, uterus, testis, skin, eye, tongue, oesophagus, stomach, intestine, pancreas, adrenal glands, gall bladder, were added to 10 volumes of Choline chloride:Trifluoroacetamide (1:2 mol:mol) and incubated between 4° C. or room temperature for at least one hour to allow penetration and tissue fixation to occur. Longer incubation periods of greater than one hour are also compatible, for example 4, 8, 15, 24 or 72 hours. The tissue sample can also be frozen and stored in the Choline chloride:Trifluoroacetamide (1:2 mol:mol) mixture until needed. The required time for tissue fixation will depend on a number of factors including the tissue type, size, density, fat content, shape, surface area and the fixative type. Determining the minimum time necessary for fixation for a particular tissue can be carried out most simply by incubating the tissue for different lengths of time and then observing how the tissue performs during microtome sectioning; insufficient fixation time would be detected by the tissue tearing during the passage of the microtome blade. Sufficient fixation time leads to a robust sample for microtome sectioning but also RNA stabilisation.

Following fixation in Choline chloride:Trifluoroacetamide (1:2 mol:mol) the tissue is rinsed once briefly in 10 volumes of PBS prior to dehydration in 70% ethanol for 45 minutes, 80% ethanol for 45 minutes, twice in 100% ethanol for 30 minutes, twice in toluene for 30 minutes prior to embedding in paraffin (melting point 56-58° C.) at 65° C. and 100° C. for 1 hour each. The paraffin block containing the fixed tissue is allowed to cool to room temperature prior to microtoming according to standard protocols identical to those used for formaldehyde fixed tissues. Detailed methods are set out in Al-Mulla and Gohlmann (2011) Formalin-Fixed Paraffin-Embedded Tissues: Methods and Protocols (Methods in Molecular Biology). Toluene can be replaced with xylene or Histosol if required.

The addition of 1-33 mM, preferably 10-33 mM of Zinc salts such as Zinc chloride, Zinc sulphate or Zinc citrate to the Choline chloride:Trifluoroacetamide improves the rate of penetration and fixation of the tissue by the fixative, whilst the additional presence of Molecular sieves Type 4A improves RNA stabilisation in the sample.

Tissue section staining with Haemotoxylin and Eosin was according to standard and well known methods.

20. HeLa Cell RNA and DNA Stabilisation with Choline Chloride:Trifluoroacetamide Following Paraffin Embedding HeLa cell pellets (one million cells) were added to 400 mg of Choline chloride:Trifluoroacetamide (1:2 mol:mol) containing 10 mM ZnCl2 and fixed for 60 minutes at room temperature. The fixed cells were either processed immediately or a standard paraffin embedding protocol was followed; (i) 30 minutes immersion in 1 ml of 100% ethanol, (ii) 15 minutes with 1 ml Toluene, then either a (iii) 15 or (iv) 60 minute infiltration with 1 ml paraffin at 55° C. RNA and DNA was subsequently purified (RNeasy, Qiagen, Germany) and the RIN determined (Agilent Bioanalyser 2100). The RIN of the HeLa cell RNA decreased from 9.6 (Lane 1, positive control) with no fixation, to 8.6 (Lane 6) following fixation, dehydration and paraffin embedding, demonstrating that although some RNA degradation did occur during processing, the overall amount was very acceptable. It was also found that Choline chloride:Trifluoroacetamide fixation resulted in far less RNA degradation than with formaldehyde treated samples (data not shown). The integrity of the DNA samples did not visibly change demonstrating that DNA is also stabilised during fixation. Results shown in FIG. 14.

21. Mouse Liver and Kidney Tissue RNA and DNA Stabilisation with Choline Chloride:Trifluoroacetamide Following Paraffin Embedding 10 mg pieces of mouse liver or kidney were added to either 400 μl of Choline chloride:Trifluoroacetamide (1:2 mol:mol) containing both 10 mM ZnSO4 and Molecular sieves 4A (3% (wt:wt), or to 400 µl of PBS and incubated for 64 hours at either 4° C. or 24° C. The tissue samples were then processed at as follows; 60 min in 70% ethanol, 60 min in 80% ethanol, 60 min in 95% ethanol, two times 30 min in 100% ethanol, 60 min in 100% ethanol, two times 30 min in toluene, 60 min in 100% toluene, 2 hours in paraffin at 55° C., 5 hours in paraffin at 55° C., the sample embedded in the paraffin was then frozen for approximately 2 weeks at –80° C. RNA and DNA was subsequently purified by first removing the embedded tissue from the paraffin block using a scalpel, and then direct lysis in 400 µl of buffer RLT using an RNeasy mini kit (Qiagen, Germany) and the RIN determined using an RNA 6000 Nano total RNA kit (Agilent Bioanalyser 2100, USA).

Results are shown in FIG. 15. It was found that for both the liver (Lanes 1-4) and kidney (Lanes 5-8) samples, RNA integrity was significantly better following Choline chloride:Trifluoroacetamide, ZnSO4 and Molecular sieves treatment (Lanes 1, 2, 5, 6) compared with PBS (Lanes 3, 4, 7, 8). As an example, the RIN values are shown in FIG. 14 and were found to decrease from 7.5 to 2.4 comparing Choline chloride:Trifluoroacetamide, ZnSO4 and Molecular sieves (Lane 1) with PBS (Lane 3) at 24° C., the DNA quality was also found to be significantly better following Choline chloride:Trifluoroacetamide, ZnSO4 and Molecular sieves treatment.

and RNA Integrity Number (RIN) determination using an Agilent Bioanalyser 2100 according to manufacturer's instructions. Whilst the addition of water to the HeLa cell pellet/Choline chloride:Trifluoroacetamide markedly reduces the integrity of the RNA, the addition of Zinc sulphate, or more preferably Zinc sulphate and Molecular sieves Type 4A can substantially reduce the amount of RNA degradation when water is present as indicated by an increase in the RIN number. This is particularly useful means to improve sample analyte quality when substantial amounts of water (for example more than 10% final concentration in the stabilising solution) are present such as with larger tissue samples, blood, serum, plasma or plant material. Some improvement may also be obtained with samples containing less than 10% water when extended sample storage is necessary.

It has been found that Zinc sulphate at 1-33 mM, preferably 10 mM (final concentration) is slightly more effective at reducing RNA degradation than Zinc chloride or Zinc EDTA, but significantly more effective than Zinc gluconate, Zinc acetate or Zinc p-Toluene sulphonate (Table 2).

TABLE 7

RIN Scores for RNA extracted from HeLa cell pellets.

| | DES Mixture (mol:mol) | Additive | RIN Score |
|---|---|---|---|
| 1 | Choline chloride:Trifluoroacetamide (1:2) | — | 8.4 |
| 2 | Choline chloride:Trifluoroacetamide (1:2) | 10% water | 6.2 |
| 3 | Choline chloride:Trifluoroacetamide (1:2) | 10% water + 33 mM ZnSO4 | 7.3 |
| 4 | Choline chloride:Trifluoroacetamide (1:2) | 10% water + 33 mM ZnSO4 + 33% Molecular sieves | 8.2 |
| 5 | Choline chloride:Trifluoroacetamide (1:2) | 15% water | 2.9 |
| 6 | Choline chloride:Trifluoroacetamide (1:2) | 15% water + 33 mM ZnSO4 | 5.3 |

22. HeLa Cell RNA Stabilisation with Choline Chloride:Trifluoroacetamide, Zinc Sulphate and Molecular Sieves A comparison was made of the RNA stabilisation effect of adding various Zinc salts and Molecular sieves to Choline chloride:Trifluoroacetamide (1:2 mol:mol) in stored biological samples with or without added water. A freshly centrifuged pellet of one million HeLa cells was used as a source of RNA, and 400 µl of Choline chloride:Trifluoroacetamide (1:2 mol:mol) was added to each pellet, then water at either a final concentration of 10 or 15% (vol:vol) was added in the presence or absence of 33 mM Zinc sulphate and 33% (wt:wt) Molecular sieves Type 4A as set out in the table. The samples were stored for 18 hours at 37° C. prior to RNA purification using silica spin columns (Invitek, Germany)

23. HeLa Cell RNA Stabilisation with Choline Chloride:Trifluoroacetamide with Organic Additives A comparison was made of the RNA stabilisation effect of adding N-Ethylpyrrolidone or Tetramethylurea to Choline chloride:Trifluoroacetamide (1:2 mol:mol) in stored biological samples with or without added water. A freshly centrifuged pellet of one million HeLa cells was used as a source of RNA, and 400 µl of Choline chloride:Trifluoroacetamide (1:2 mol:mol) was added to each pellet, in the presence or absence of 2.5, 5%, 10% or 20% (vol:vol) N-Ethylpyrrolidone, 5% or 20% (vol:vol) Tetramethylurea as set out in the table. The samples were stored for 20 days at 24° C. prior to RNA purification using silica spin columns (InviTrap Spin Universal RNA Mini Kit Cat. No. 1060100200 Stratec Molecular, Germany) and RNA Integrity Number (RIN) determination using an Agilent Bioanalyser 2100 according to manufacturer's instructions. It was found that both N-Ethylpyrrolidone and Tetramethyurea improved RNA quality in the HeLa cell pellet following prolonged storage compared with Choline chloride:Trifluoroacetamide alone.

TABLE 8

RNA Yields and Quality with N-Ethylpyrrolidone and Tetramethylurea.

| DES Mixture | Additive | RNA Yield ng/ul | RNA Quality |
|---|---|---|---|
| Choline chloride:Trifluoroacetamide (1:2) | — | 219 | 7 |
| Choline chloride:Trifluoroacetamide (1:2) | 2.5% N-Ethylpyrrolidone | 92 | 7 |

TABLE 8-continued

RNA Yields and Quality with N-Ethylpyrrolidone and Tetramethylurea.

| DES Mixture | Additive | RNA Yield ng/ul | RNA Quality |
|---|---|---|---|
| Choline chloride:Trifluoroacetamide (1:2) | 5% N-Ethylpyrrolidone | 87 | 8 |
| Choline chloride:Trifluoroacetamide (1:2) | 10% N-Ethylpyrrolidone | 54 | 9 |
| Choline chloride:Trifluoroacetamide (1:2) | 20% N-Ethylpyrrolidone | 139 | 9 |
| Choline chloride:Trifluoroacetamide (1:2) | 5% Tetramethylurea | 194 | 8 |
| Choline chloride:Trifluoroacetamide (1:2) | 20% Tetramethylurea | 211 | 7 |

Qualitative RNA quality scale as follows; 0 (highly degraded) to 10 (highest quality). The RNA analysis in Table 1 and 2 was carried out as follows; ethidium bromide stained, 1% agarose 0.5×TAE gel electrophoresis followed by visual analysis of a photograph taken under uv light, of the integrity of the 18S and 28S rRNA bands. An RNA sample with an RNA Quality score of 8 or more has an 18S to 28S rRNA ethidium bromide staining ratio of 1:2, whilst an RNA sample with an RNA Quality score of 5 has an 18S to 28S rRNA staining ratio of approximately 1:1.

24. Using Various Quaternary Ammonium Salts and Hydrogen Bond Donors

A room temperature (24° C.) DES liquid could not be prepared from mixing Choline chloride with any of Proline, Oxamide, Pivalamide, 1-Ethyl-2-pyrrol, 4-Formyl morpholine, Acetonyl acetone, Ethylene carbonate, Tetramethyl urea, N-Ethylimidazole, 1-Benzylimidazole and/or 1,3-Dimethyl-2-imidazolidone, in a 1:2 mol:mol proportion. The following ammonium salts were also not capable of forming room temperature DES liquids; Ammonium phosphate and Ammonium acetate. Both Ammonium sulphate and Ammonium chloride could partially form, at 100° C. but not at 24° C., a liquid in a 1:2 mol:mol ratio with Guanidine isothiocyanate, Sorbitol and/or Xylitol.

Choline chloride:Trifluoroacetamide stabilised RNA was significantly better than that of RNAlater.

26. Stabilisation of RNA in *Allium cepa* Leaf Shoots 10 mg of *A. cepa* leaf shoots were mixed with either 400 μl of Choline chloride:Trifluoroacetamide (1:2 mol:mol) (Lanes 1-3) or RNAlater (Qiagen, Germany) (Lanes 4-6) and incubated at 22° C. for either 18 hours (Lanes 1, 4), 3 days (Lanes 2, 5) or 9 days (Lanes 3, 6) prior to RNA purification (RNeasy Mini Kit, Cat. No. 74106, Germany). The quality of RNA is shown in FIG. 17, the Choline chloride:Trifluoroacetamide stabilised RNA was significantly better than that of RNAlater.

27. In Situ Hybridisation Applications Following DES Stabilisation

Tissue samples were prepared and paraffin embedded as set out in Example 21 using Choline chloride:Trifluoroacetamide (1:2 mol:mol) and 10 mM ZnSO4 with a fixation time of 1-24 hour at 4° C. The tissue samples were then processed at as follows; 60 min in 70% ethanol, 60 min in 80% ethanol, 60 min in 95% ethanol, two times 30 min in 100% ethanol, 60 min in 100% ethanol, two times 30 min in

TABLE 9

Two component mixtures using a variety of quaternary ammonium salts.

| | Component 1 | Component 2 | Ratio (mol:mol) | Liquid at 100° C. | Liquid at 24° C. |
|---|---|---|---|---|---|
| 1 | Choline bromide | Trifluoroacetamide | 1:2 | Yes | Partial |
| 2 | Choline chloride | Trifluoroacetamide | 1:2 | Yes | Yes |
| 3 | Choline iodide | Trifluoroacetamide | 1:2 | Yes | No |
| 4 | Choline dihydrogen citrate | Trifluoroacetamide | 1:2 | Yes | No |
| 5 | Choline bitartrate | Trifluoroacetamide | 1:2 | Yes | No |
| 6 | Betaine | Trifluoroacetamide | 1:2 | Yes | Yes |
| 7 | Ammonium sulphate | Trifluoroacetamide | 1:2 | No | No |
| 8 | Ammonium sulphate | Guanidine isothiocyanate | 2:1 | No | No |
| 9 | Ammonium sulphate | Guanidine isothiocyanate | 1:2 | Partial | No |
| 10 | Ammonium sulphate | Xylitol | 1:2 | Partial | No |
| 11 | Ammonium sulphate | Sorbitol | 1:2 | Partial | No |
| 12 | Ammonium chloride | Guanidine isothiocyanate | 1:2 | Partial | No |
| 13 | Ammonium chloride | Xylitol | 1:2 | Yes | No |
| 14 | Ammonium chloride | Sorbitol | 1:2 | Yes | No |
| 15 | Ammonium sulphate | Trifluoroacetamide | 1:2 | No | No |

25. Stabilisation of RNA in *Drosophila melanogaster* Embryos 10 mg of *D. melanogaster* embryos (0-24 hours) were mixed with either 400 μl of Choline chloride:Trifluoroacetamide (1:2 mol:mol) (Lanes 1-3) or RNAlater (Lanes 4-6) and incubated at 37° C. for either 12 hours (Lanes 1, 4), 2 days (Lanes 2, 5) or 45 days (Lanes 3, 6) prior to RNA purification (RNeasy Mini Kit, Cat. No. 74106, Qiagen, Germany). The quality of RNA is shown in FIG. 16, the toluene, 60 min in 100% toluene, 2 hours in paraffin at 55° C. then 5 hours in paraffin at 55° C. Following microtome preparation of the paraffin-tissue slices (3-12 μm thick), the paraffin was removed using xylene for 10 minutes at room temperature, the tissue slices were then hydrated by incubating in 100% ethanol, 70% ethanol, 50% ethanol, 25% ethanol and then water for 5 minutes each. The tissue sections can then be proteinase K (10 μg/ml) treated for 5 minutes at room temperature before rinsing in PBS and pre-hybridisation in 1 ml of buffer containing 500 μl ultrapure 50% formamide, 250 µl of 20×SSC, 50 µl of 10 µg/µl yeast t-RNA and 20 µl of 50×Denhardt's solution and then hybridization with an appropriate chromogenic or fluorescently labelled probe. Protocols for in situ hybridisation are well known and described by J. M. Bridger and K Morris (2010), in Fluorescence in situ Hybridization (FISH): Protocols and Applications (Methods in Molecular Biology) and Summersgill et al., (2007) Nature Protoc. 3:220-234.

28. Preparation of Cells for Flow Cytometry

Approximately 500,000 tissue culture cells such as HeLa, MCF-7, NC160, PC3, Vero, GH3, MC3T3, ZF4 or IMR-90, if growing on a solid surface were first lightly trypsinised to detach them, mixed with 10 ml of EMEM/10% FBS and centrifuged in a 15 ml tube for 10 minutes at 900×g (24° C.). The cell pellet was then resuspended in 100 µl of DPBS buffer and immediately mixed with 1 ml of Choline chloride:Trifluoroacetamide (1:2 mol:mol) and gently pipetted with a 10 ml pipette to thoroughly mix. The cells were left to fix for 1-24 hours at either 4° C. or 24° C., then 14 ml of DPBS was added, the tube contents mixed by gentle inversion and centrifuged for 10 minutes at 900×g and the cell pellet gently resuspended in 100 µl of DPBS and the nuclei stained by adding 1 ml DAPI (3 µM) in staining buffer (100 mM Tris, pH 7.4, 150 mM NaCl, 1 mM $CaCl_2$, 0.5 mM $MgCl_2$, 0.1% Nonidet P-40) for 15 minutes (24° C.). The stained and fixed cells can then be used for flow cytometry. It was found that the Choline chloride:Trifluoroacetamide fixed cells were mono-dispersed and could be sorted into the various stages of the cell cycle according to their fluorescence.

29. Two-step Treatment of Biological Samples 10 mg pieces of mouse tissue were added to either 400 µl of Choline chloride:Trifluoroacetamide (1:2 mol:mol) containing both 10 mM ZnSO4 and Molecular sieves 4A (3% (wt:wt), were incubated at 24° C. for 1 hour, the tissue was then removed, briefly dabbed with a paper towel to remove excess stabilizer before subsequent immersion in, for example, 400 µl of either Choline chloride: Trifluoroacetamide (1:2 mol:mol), Choline chloride:Urea (1:2 mol:mol), Choline chloride:Sorbitol (1:2 mol:mol), Betaine chloride:Trifluoacetamide (1:2 mol:mol) or 4% paraformaldehyde and then incubated and stored for at least one hour but preferably overnight. Alternatively, any one of a number of DES mixtures as set out in this application can serve as the first stabilising or fixation solution followed by a second stabilising or fixation solution. As one more example, tissue fixation can first be carried out with for example 4% paraformaldehyde for one hour at room temperature and then the tissue transferred to 400 µl of Choline chloride:Trifluoroacetamide (1:2 mol:mol) containing both 10 mM ZnSO4 and Molecular sieves 4A (3% (wt:wt). This two-step procedure provides a means by which, for example, the optimum stabilizer for cell morphology can subsequently be combined with the optimum stabilizer for RNA, DNA and proteins. It also provides a means by which the water content originating from the biological sample can be reduced by changing the original stabilising mixture. It will be evident to one skilled in the art that there are many combinations of the first and second mixtures and that the most appropriate choices will have to be determined at least in part by empirical means such as quality of H&E stained tissue sections and RNA quality. It should also be noted that the stabilization and fixation mixtures used can either be liquids or solids.

30. Compatibility of DES Mixtures with Guanidine and Phenol Purification Reagents Advantageously, Choline chloride:Trifluoroacetamide (1:2 mol:mol) is completely soluble and compatible with both guanidine thiocyanate or HCl based virus, cell and tissue lysis buffers such as those found in these RNA purification kits; RNeasy Mini, (Qiagen, Germany), PureLink™ (Life Technologies, USA), MagNA Pure LC RNA Isolation Kit III, High Pure RNA Tissue Kit and RNA Micro Kit Amplicor HCV (Roche Applied Science, USA), NucleoSpin® Multi-8 Virus RAV (Macherey Nagel, Germany), TEMPUS™ Blood RNA Tube (Applied Biosystems, USA), SV RNA Kit and PureYield™ Kit (Promega, USA), ToTALLY RNA™ Kit (Ambion, USA), GenElute™ Mammalian Total RNA Purification (Sigma-Aldrich, USA), PAXgene™ Blood RNA Kit (PreAnalytix, Germany) and phenol based purification reagents such as TRIzol (Life Technologies, USA) allowing Choline chloride:Trifluoroacetamide (1:2 mol:mol) stabilized samples to be directly mixed with guanidine or phenol purification reagents without needing to separate the sample from the Choline chloride:Trifluoroacetamide. This can be advantageous when, for example, it is not practical to separate a tissue sample that has penetrated by the fixative, or when individual cells such as tissue culture cells, blood or CTC's are mixed with a much larger volume of fixative and can be difficult or impossible to separate by centrifugation. As a point of reference, mammalian cells in RNAlater (Qiagen, Germany) cannot be pelleted by centrifugation or the RNA purified by mixing the cell plus RNAlater with guanidine lysis buffers as the RNA yields drop dramatically.

As one example, it has been found that RNA containing samples containing as little as 6% (Sample 5, Table 10) or less of Buffer RLT in Choline chloride:Trifluoroacetamide (1:2 mol:mol), can, on mixing with one volume of 70% ethanol be used to effectively bind RNA to a silica spin column membrane (RNeasy mini, Qiagen, Germany) with excellent yield and purity as set out in Table 10. A mouse liver lysate was prepared by lysing 100 mg of liver in 1 ml of Buffer RLT, then 20 µl portions of the lysate were added to Buffer RLT and then the Choline chloride:Trifluoroacetamide, before mixing with 70% ethanol as shown in Table 10 and binding to a RNeasy mini spin column. The RNA was then purified according to manufacturer's instructions (RNeasy mini, Qiagen, Germany) with an elution volume of 50 µl water. The RNA yields and purity were determined using a Nanodrop ND-1000. It was surprisingly found that not only did Choline chloride:Trifluoroacetamide allow the chaotropic activity of guandine to function to lyse the sample, but it had no effect on the RNA binding to the silica spin column membrane so that yields were either not effected or slightly increased.

Furthermore, Choline chloride:Trifluoroacetamide can replace the otherwise essential RNA binding function of 70% ethanol when added to the guanidine lysate (20 µl), the standard manufacturer's protocol (RNeasy Mini, Qiagen, Germany), and as shown in Table 11, requires the addition of one volume of 70% ethanol to the lysate to allow the RNA to bind to the silica membrane. If 70% ethanol is not added to the lysate then RNA cannot bind to the silica membrane, however, and if the sample contains Choline chloride:Trifluoroacetamide then the RNA can bind even in the absence of ethanol, this provides a means to reduce the number of steps and improve the RNA purification procedure of, for example the RNeasy kit without the need to use flammable liquids. It should be noted that neither Choline chloride nor Choline chloride:Urea dissolved in Buffer RLT (1:1 wt:wt) have this property, whilst Trifluoroacetamide alone dissolved in Buffer RLT (1:1 wt:wt) led to only 15% of the RNA yield compared with Choline chloride:Trifluoroacetamide dissolved in Buffer RLT (1:1 wt:wt). It was also discovered that a 1:1 mixture of Buffer RLT:(Choline chloride:Trifluoroacetamide (1:2 mol:mol) had very good HeLa cell lysis activity and could be used as a standalone lysis and silica membrane binding buffer, in the absence of 70% ethanol, RNA yields with this novel mixture were significantly better than with Buffer RLT alone.

Surprisingly it was found that a HeLa cell lysate prepared in 200 µl of a 1:1 mixture of Buffer RLT:(Choline chloride:Trifluoroacetamide (1:2 mol:mol), when heated at 65° C. for 10 minutes followed by the addition of 1 volume of 70% ethanol and binding to a silica spin column (RNeasy Mini, Qiagen, Germany) according to manufacturer's instructions resulted in the exclusive purification of small RNA (miRNA, tRNA and 5S rRNA). If the heating step was omitted total RNA was purified including the 18 and 28S rRNA species, heating therefore offers a novel method to selectively purify small RNA from a cell lysate. Replacing Trifluoroacetamide with Urea in the Lysis mixture and then heating resulted in extreme RNA degradation, as did heating the lysate in the absence of Choline chloride:Trifluoroacetamide.

continued using a RNeasy Mini kit according to manufacturer's instructions (Qiagen, Germany). It was found that the integrity of the 16 and 23S rRNA was unchanged compared with RNA extracted from a fresh bacterial pellet. Alternatively ZnSO4 can be added to the Choline chloride:Trifluoroacetamide (1:2 mol:mol) to give a final concentration of 1-33 mM, preferably 33 mM and 10% (wt:wt) Molecular sieves can also be optionally added to improve stabilisation.

32. Multi-Component DES Mixtures

It has been found that a RNA stabilising DES mixture can be simply prepared by mixing more than two components together such as Betaine:Choline chloride:Trifluoroacetamide (0.5:0.5:2 mol:mol:mol) instead of either Betaine:Trifluoroacetamide (1:2 mol:mol) or Choline chloride:Trifluoroacetamide (1:2 mol:mol). Alternatively, novel DES mixtures can be made from, for example Choline chloride:Urea:Trifluoroacetamide (1:1:1 mol:mol:mol) or Betaine:Urea:Trifluoroacetamide (1:1:1 mol:mol:mol) or even Betaine:Choline chloride:Urea:Trifluoroacetamide (0.5:0.5:1:1 mol:mol:mol:mol). Such three or more component DES mixtures can have interesting novel properties such as reduced viscosity, improved shelf-life, improved nucleic acid stability or cell fixation properties based on the interactions and properties of all the components together in a single DES mixture.

As one example, to a HeLa pellet (500,000 cells) was added 400 mg of either Choline chloride; Trifluoroacetamide (1:2 mol:mol), Betaine:Choline chloride:Trifluoroacetamide (0.5:0.5:2 mol:mol:mol) or Betaine:Trifluoroacetamide (1:2 mol:mol) each containing 10 mM ZnSO4 and incubated overnight at 37° C. followed by RNA and DNA purification

TABLE 10

RNA yields from guanidine/Choline chloride:Trifluoroacetamide mixtures.

| | Volume RLT (guanidine) | Volume Choline chloride:Trifluoroacetamide | Volume 70% Ethanol | OD 260/280 nm | RNA yield ng/µl |
|---|---|---|---|---|---|
| 1 | 350 µl | 0 µl | 350 µl | 2.05 | 171 |
| 2 | 150 µl | 170 µl | 350 µl | 2.25 | 192 |
| 3 | 100 µl | 220 µl | 350 µl | 2.22 | 203 |
| 4 | 50 µl | 270 µl | 350 µl | 2.2 | 198 |
| 5 | 0 µl | 330 µl | 350 µl | 1.53 | 200 |
| 6 | 170 µl | 170 µl | 0 µl | 2.21 | 52 |

TABLE 11

RNA yields from Guanidine/Choline chloride:Trifluoroacetamide mixtures in the absence of ethanol for binding.

| | Volume RLT (guanidine) | Volume and DES Type | Volume 70% Ethanol | OD 260/280 nm | RNA yield ng/µl |
|---|---|---|---|---|---|
| 1 | 330 µl | 0 µl Choline chloride:Trifluoroacetamide | 0 µl | 1.98 | 3 |
| 2 | 230 µl | 90 µl Choline chloride:Trifluoroacetamide | 0 µl | 1.84 | 6.5 |
| 3 | 150 µl | 170 µl Choline chloride:Trifluoroacetamide | 0 µl | 2.04 | 143 |
| 4 | 100 µl | 220 µl Choline chloride:Trifluoroacetamide | 0 µl | 2.04 | 132 |
| 5 | 50 µl | 270 µl Choline chloride:Trifluoroacetamide | 0 µl | 2.05 | 192 |
| 6 | 0 µl | 330 µl Choline chloride:Trifluoroacetamide | 0 µl | 2.03 | 247 |
| 7 | 150 µl | 170 µl Choline chloride:Urea | 0 µl | 2.14 | 9 |

31. Stabilisation of Total RNA in Bacteria

300 µl of Choline chloride:Trifluoroacetamide (1:2 mol:mol) was added to a 10 mg pellet of *Escherischia coli* DH5α and incubated at 22° C. for 18 hours, then either the DES liquid was removed and 400 µl of Buffer RLT added to the pellet, or 400 µl of Buffer RLT was added directly to the pellet and DES liquid, the tube vortexed for 20 seconds, then briefly sonicated to rupture the cells and RNA purification using a RNeasy Mini kit (Qiagen, Germany) and determination of the RIN (Agilent Bioanalyser 2100, USA).

It will be evident to one skilled in the art that many such DES mixtures are possible, with variable components and molar concentrations and the most appropriate mixture for the application will need to be determined empirically.

TABLE 12

Comparison of RNA, DNA yields and RNA Integrity Number (RIN) of three different DES mixtures on HeLa cells incubated overnight at 37° C.

| | DES Mixture (including 10 mM ZnSO4) | RNA ng/ul | DNA ng/ul | RIN |
|---|---|---|---|---|
| 1 | Choline chloride:Trifluoroacetamide (1:2 mol:mol), | 251 | 36 | 9.3 |
| 2 | Betaine:Choline chloride:Trifluoroacetamide (0.5:0.5:2 mol:mol:mol) | 229 | 42 | 9.5 |
| 3 | Betaine:Trifluoroacetamide (1:2 mol:mol) | 182 | 30 | 9.4 |

33. Aqueous Mixtures of DES for Cell Fixation

It has been found that aqueous dilutions of Choline chloride:Trifluoroacetamide (1:2 mol:mol) are capable of fixing tissue culture cells and tissues. DMEM tissue culture medium (Life Technologies, France) was added to a solution of Choline chloride:Trifluoroacetamide to give a final concentration of 0, 6, 12, 21 or 50% DMEM, 400 µl portions of the mixture was then added to HeLa tissue culture cells in a 24-well plate and observed with a microscope. It was discovered that whilst all the mixtures could fix the cells without hypo- or hyper-tonic effects on the cells, Choline chloride:Trifluoroacetamide containing 6% DMEM led to the best quality cell morphology, superior even to pure Choline chloride:Trifluoroacetamide. It should be noted that dilutions of Choline chloride:Trifluoroacetamide with greater than 15% water can cause the cell membrane to form microdroplets and then be lost from the cell, the cytoplasm of which remains intact. Aqueous dilutions of a DES provides a simple means to reduce the viscosity and cost as well as potentially improving the cell fixation properties, however the presence of water has a deleterious effect on RNA stability. It will be apparent to one skilled in the art that a large number of different aqueous solutions such as water, PBS, DPBS, sugar solutions or DMEM with different DES's are capable of being mixed and that the effect on cell fixation and biomolecule stability may have to be tested empirically.

34. Anti-bacterial Activity of DES Mixtures

Pellets of $1\times10^9$ E. coli DH5a cells were treated with 90 µl of an aqueous dilution of Choline chloride:Trifluoroacetamide (1:2 mol:mol) to give a final concentration of either 90%, 9% or 0.9%, for 25 minutes at room temperature and then plated onto an agar plate and incubated overnight at 37° C. to allow colony growth. It was found the 90% Choline chloride:Trifluoroacetamide but not the 9% or 0.9% dilutions stopped all bacterial growth and colony formation. Choline chloride:Trifluoroacetamide therefore appears to be a have a powerful anti-bacterial activity, and it will be evident to one skilled in the art that longer treatment periods or different DES mixtures may lead to an even stronger anti-effect. Advantageously bacterial growth would be expected to be inhibited in tissue samples stored in Choline chloride:Trifluoroacetamide stopping spoilage.

35. In Situ Preparation of a DES Liquid

Whilst it is usually convenient to prepare a DES mixture in advance of its use for fixation and stabilisation, an alternative is to add the two or more components of the DES together as solids and at the same time as the sample. For example, in a single tube, 1.28 g of Choline chloride solid was added to 2 g of Trifluoroacetamide solid and then 50-100 µl of whole blood or 25 mg of tissue sample added and the solids allowed to freely mix and form a eutectic mixture of (1:2 mol:mol) in the presence of the biological sample. Alternatively, the two solids can be added as two preloaded layers in a suitable vessel such as a blood collection tube, but separated by a membrane which ruptures or dissolves on contact with the sample thereby allowing the components to mix and form the DES liquid only in the presence of sample. Another possibility is to have two open compartments in a suitably closed top vessel each compartment being preloaded with an appropriate amount of, for example, Choline chloride and the other Trifluoroacetamide. On shaking or inversion the two components can freely mix and form a DES liquid, if needed in the presence of the sample.

36. RNA Stabilisation with Adherent Tissue Culture Cells

Human Embryonic Fibroblast cells (HEF) were grown to 80% confluence (approximately 200,000 cells) in a 24-well tissue culture plate, the growth medium removed and replaced with 400 µl of either Choline chloride:Trifluoroacetamide (1:2 mol:mol) or RNAlater and incubated at 37° C. for 0, 32 hours or 9 days prior to RNA purification and RIN analysis (Agilent Bioanalyser). Table 13 shows that adherent tissue culture cell RNA can be extremely well preserved using either Choline chloride:Trifluoroacetamide (1:2 mol:mol).

TABLE 13

RIN Scores for RNA extracted from Human Embryonic Fibroblast (HEF) adherent cells stored at 37° C.

| | Treatment | Time | RIN |
|---|---|---|---|
| 1 | Control | 0 | 9.1 |
| 2 | Choline chloride:Trifluoroacetamide (1:2 mol:mol) | 32 hours | 9.1 |
| 3 | Choline chloride:Trifluoroacetamide (1:2 mol:mol) | 9 days | 8 |
| 4 | Control | 0 | 8.8 |
| 5 | RNAlater ® | 32 hours | 9.4 |
| 6 | RNAlater ® | 9 days | 7.6 |

The invention claimed is:

1. A composition comprising a eutectic solvent, wherein said eutectic solvent comprises a first component and a second component; wherein said first component is trimethylglycine and said second component is trifluoroacetamide; wherein said first component and said second component are in a molar ratio of between about 1:1.5 and about 1:2.5; and wherein said first component and said second component together comprise at least about 88% by weight of the composition, wherein said composition further comprises a sample comprising one or more of a biomolecule, RNA, DNA, protein, phosphoprotein, virus, cell, tissue, solid tissue, plasma, serum, brain, cerebrospinal fluid, whole blood, or whole blood comprising a circulating tumor cell.

2. The composition of claim 1, wherein said sample comprises RNA.

3. The composition of claim 1, wherein said sample comprises one or more of viruses, influenza, human papillomavirus, human immunodeficiency virus, hepatitis A virus, hepatitis C virus, hepatitis E virus, foot and mouth disease virus, severe acute respiratory syndrome virus, West Nile virus, Ebola virus, yellow fever virus, dengue fever virus, bacteria, *Escherichia coli*, *Staphylococcus* spp., *Streptococcus* spp., *Mycobacterium* spp., *Pseudomonas* spp., bacteria that cause shigella, diphtheria, tetanus, syphilis, chlamydia, legionella, listeria, or leprosy, parasites, *Leishmania* spp., *Trypanosoma* spp., or *Plasmodium* spp.

4. The composition of claim 1, wherein said sample comprises a biomolecule and said eutectic solvent prevents degradation of said biomolecule in said sample.

5. The composition of claim 1, wherein the molar ratio of said first component to said second component is about 1:2.

6. The composition of claim 1, wherein the eutectic solvent has a pH between 5 and 7.5.

7. The composition of claim 1, wherein the eutectic solvent further comprises zinc sulfate, a desiccant, sodium dodecyl sulfate, sodium benzoate, N-methyl pyrrolidone, N-ethyl pyrrolidone, 1-methylimidazole, 1-benzylimidazole, tetramethylurea, 4-Formyl morpholine, water, and/or acetic acid.

8. The composition of claim 7, wherein said desiccant comprises a silica gel and/or a molecular sieve.

9. The composition of claim 7, wherein said zinc sulfate is present in the eutectic solvent in an amount in the range 0.01% to 1.5% by weight of the eutectic solvent.

10. A composition comprising a eutectic solvent, wherein said eutectic solvent comprises a first component and a second component; wherein said first component is trimethylglycine and said second component is trifluoroacetamide; wherein said first component and said second component are in a molar ratio of between about 1:1.8 and about 1:2.2; and wherein said first component and said second component together comprise at least about 88% by weight of the composition, wherein said composition further comprises a sample comprising one or more of a biomolecule, RNA, DNA, protein, phosphoprotein, virus, cell, tissue, solid tissue, plasma, serum, brain, cerebrospinal fluid, whole blood, or whole blood comprising a circulating tumor cell.

11. The composition of claim 10, wherein said sample comprises RNA.

12. The composition of claim 10, wherein said sample comprises one or more of viruses, influenza, human papillomavirus, human immunodeficiency virus, hepatitis A virus, hepatitis C virus, hepatitis E virus, foot and mouth disease virus, severe acute respiratory syndrome virus, West Nile virus, Ebola virus, yellow fever virus, dengue fever virus, bacteria, *Escherichia coli*, *Staphylococcus* spp., *Streptococcus* spp., *Mycobacterium* spp., *Pseudomonas* spp., bacteria that cause shigella, diphtheria, tetanus, syphilis, chlamydia, legionella, listeria, or leprosy, parasites, *Leishmania* spp., *Trypanosoma* spp., or *Plasmodium* spp.

13. The composition of claim 10, wherein said sample comprises a biomolecule and said eutectic solvent prevents degradation of said biomolecule in said sample.

14. The composition of claim 10, wherein the molar ratio of said first component to said second component is 1:2.

15. The composition of claim 10, wherein the eutectic solvent has a pH between 5 and 7.5.

16. The composition of claim 10, wherein the eutectic solvent further comprises zinc sulfate, a desiccant, sodium dodecyl sulfate, sodium benzoate, N-methyl pyrrolidone, N-ethyl pyrrolidone, 1-methylimidazole, 1-benzylimidazole, tetramethylurea, 4-Formyl morpholine, water, and/or acetic acid.

17. The composition of claim 16, wherein said desiccant comprises a silica gel and/or a molecular sieve.

18. The composition of claim 16, wherein said zinc sulfate is present in the eutectic solvent in an amount in the range 0.01% to 1.5% by weight of the eutectic solvent.

\* \* \* \* \*